(12) United States Patent
Sanchez et al.

(10) Patent No.: US 11,376,152 B2
(45) Date of Patent: *Jul. 5, 2022

(54) APPARATUS AND METHODS FOR RECEIVING DISCHARGED URINE

(71) Applicant: PUREWICK CORPORATION, El Cajon, CA (US)

(72) Inventors: Robert A. Sanchez, Riverton, UT (US); Camille R. Newton, Bonsall, CA (US); Joseph M. Forehand, La Mesa, CA (US); Raymond J. Newton, Bonsall, CA (US)

(73) Assignee: PureWick Corporation, El Cajon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/088,272

(22) Filed: Nov. 3, 2020

(65) Prior Publication Data

US 2021/0069005 A1 Mar. 11, 2021

Related U.S. Application Data

(63) Continuation of application No. 16/245,726, filed on Jan. 11, 2019, which is a continuation of application
(Continued)

(51) Int. Cl.
*A61F 5/00* (2006.01)
*A61F 5/44* (2006.01)
(Continued)

(52) U.S. Cl.
CPC ............ *A61F 5/4404* (2013.01); *A61D 99/00* (2013.01); *A61F 5/443* (2013.01); *A61F 5/4405* (2013.01);
(Continued)

(58) Field of Classification Search
CPC ...... A61F 5/4404; A61F 5/4405; A61F 5/443; A61F 5/453; A61F 5/455; A61F 5/4407;
(Continued)

(56) References Cited

U.S. PATENT DOCUMENTS

| 1,032,841 A | 7/1912 | Koenig |
| 1,742,080 A | 12/1929 | Jones |

(Continued)

FOREIGN PATENT DOCUMENTS

| CA | 3098571 A1 | 11/2019 |
| CN | 2269203 Y | 12/1997 |

(Continued)

OTHER PUBLICATIONS

US 9,908,683 B2, 03/2018, Sandhausen et al. (withdrawn)
(Continued)

*Primary Examiner* — Andrew J Mensh
(74) *Attorney, Agent, or Firm* — Dorsey & Whitney LLP

(57) ABSTRACT

A system suitable for collecting and transporting urine away from the body of a person or animal may include an assembly having a fluid impermeable casing having a fluid reservoir at a first end, a fluid outlet at a second end, and a longitudinally extending fluid impermeable layer coupled to the fluid reservoir and the fluid outlet and defining a longitudinally elongated opening between the reservoir and the outlet. The assembly can further include a fluid permeable support disposed within the casing with a portion extending across the elongated opening, and a fluid permeable membrane disposed on the support and covering at least the portion of the support that extends across the elongated opening, so that the membrane is supported on the support and disposed across the elongated opening. The assembly can further include a tube having a first end disposed in the reservoir and a second, fluid discharge end.

21 Claims, 35 Drawing Sheets

Related U.S. Application Data

No. 15/611,587, filed on Jun. 1, 2017, now Pat. No. 10,226,376, which is a continuation-in-part of application No. 15/260,103, filed on Sep. 8, 2016, now Pat. No. 10,390,989, which is a continuation of application No. PCT/US2016/049274, filed on Aug. 29, 2016, which is a continuation-in-part of application No. 15/171,968, filed on Jun. 2, 2016, now Pat. No. 10,952,889, said application No. 15/260,103 is a continuation-in-part of application No. 14/952,591, filed on Nov. 25, 2015, now Pat. No. 11,090,183, and a continuation-in-part of application No. 14/947,759, filed on Nov. 20, 2014, now abandoned, said application No. 15/260,103 is a continuation-in-part of application No. 14/625,469, filed on Feb. 18, 2015, now abandoned.

(60) Provisional application No. 62/485,578, filed on Apr. 14, 2017, provisional application No. 62/414,963, filed on Oct. 31, 2016, provisional application No. 62/084,078, filed on Nov. 25, 2014, provisional application No. 62/082,279, filed on Nov. 20, 2014, provisional application No. 61/955,537, filed on Mar. 19, 2014.

(51) Int. Cl.
| | |
|---|---|
| *A61F 5/453* | (2006.01) |
| *A61F 5/455* | (2006.01) |
| *A61D 99/00* | (2006.01) |
| *A61F 5/443* | (2006.01) |
| *A61M 1/00* | (2006.01) |
| *A61F 5/451* | (2006.01) |
| *A61B 10/00* | (2006.01) |
| *A01K 23/00* | (2006.01) |
| *A61G 9/00* | (2006.01) |

(52) U.S. Cl.
CPC .............. *A61F 5/453* (2013.01); *A61F 5/455* (2013.01); *A01K 23/00* (2013.01); *A61B 10/007* (2013.01); *A61F 5/4407* (2013.01); *A61F 5/451* (2013.01); *A61G 9/006* (2013.01); *A61M 1/69* (2021.05)

(58) Field of Classification Search
CPC ...... A61F 5/451; A61M 1/0019; A61D 99/00; A01K 23/00; A61B 10/007; A61G 9/006
USPC ........................................................ 604/319
See application file for complete search history.

(56) References Cited

U.S. PATENT DOCUMENTS

| | | | |
|---|---|---|---|
| 1,979,899 A | 11/1934 | Obrien et al. | |
| 2,326,881 A | 8/1943 | Packer | |
| 2,613,670 A | 10/1952 | Edward | |
| 2,644,234 A | 7/1953 | Earl | |
| 2,859,786 A | 11/1958 | Tupper | |
| 2,968,046 A | 1/1961 | Duke | |
| 2,971,512 A | 2/1961 | Reinhardt | |
| 3,087,938 A | 4/1963 | Hans et al. | |
| 3,198,994 A | 8/1965 | Hildebrandt et al. | |
| 3,221,742 A | 12/1965 | Egon | |
| 3,312,981 A | 4/1967 | Mcguire et al. | |
| 3,349,768 A | 10/1967 | Keane | |
| 3,362,590 A | 1/1968 | Gene | |
| 3,366,116 A | 1/1968 | Huck | |
| 3,398,848 A | 8/1968 | Donovan | |
| 3,400,717 A | 9/1968 | Bruce et al. | |
| 3,406,688 A | 10/1968 | Bruce | |
| 3,425,471 A | 2/1969 | Yates | |
| 3,511,241 A | 5/1970 | Lee | |
| 3,512,185 A | 5/1970 | Ellis | |
| 3,520,300 A * | 7/1970 | Guiles, Jr. | A61M 1/008 604/269 |
| 3,528,423 A | 9/1970 | Lee | |
| 3,613,123 A | 10/1971 | Langstrom | |
| 3,651,810 A | 3/1972 | Ormerod | |
| 3,699,815 A | 10/1972 | Holbrook | |
| 3,726,277 A | 4/1973 | Hirschman | |
| 3,843,016 A | 10/1974 | Bornhorst et al. | |
| 3,863,798 A | 2/1975 | Kurihara et al. | |
| 3,915,189 A | 10/1975 | Holbrook et al. | |
| 3,998,228 A | 12/1976 | Poidomani | |
| 3,999,550 A | 12/1976 | Martin | |
| 4,015,604 A | 4/1977 | Csillag | |
| 4,020,843 A | 5/1977 | Kanall | |
| 4,022,213 A | 5/1977 | Stein | |
| 4,027,776 A | 6/1977 | Douglas | |
| 4,180,178 A | 12/1979 | Turner | |
| 4,187,953 A | 2/1980 | Turner | |
| 4,194,508 A | 3/1980 | Anderson | |
| 4,200,102 A | 4/1980 | Duhamel et al. | |
| 4,202,058 A | 5/1980 | Anderson | |
| 4,233,025 A * | 11/1980 | Larson | A61F 13/2071 433/136 |
| 4,233,978 A | 11/1980 | Hickey | |
| 4,246,901 A | 1/1981 | Frosch et al. | |
| 4,257,418 A | 3/1981 | Hessner | |
| 4,270,539 A | 6/1981 | Frosch et al. | |
| 4,352,356 A | 10/1982 | Tong | |
| 4,360,933 A | 11/1982 | Kimura et al. | |
| 4,365,363 A | 12/1982 | Windauer | |
| 4,387,726 A | 6/1983 | Denard | |
| 4,425,130 A | 1/1984 | Desmarais | |
| 4,446,986 A | 5/1984 | Bowen et al. | |
| 4,453,938 A | 6/1984 | Brendling | |
| 4,457,314 A | 7/1984 | Knowles | |
| 4,476,879 A | 10/1984 | Jackson | |
| 4,526,688 A | 7/1985 | Schmidt, Jr. et al. | |
| 4,528,703 A | 7/1985 | Kraus | |
| D280,438 S | 9/1985 | Wendt | |
| 4,553,968 A | 11/1985 | Komis | |
| 4,581,026 A | 4/1986 | Schneider | |
| 4,610,675 A | 9/1986 | Triunfol | |
| 4,626,250 A | 12/1986 | Schneider | |
| 4,627,846 A | 12/1986 | Ternstroem | |
| 4,631,061 A | 12/1986 | Martin | |
| 4,650,477 A | 3/1987 | Johnson | |
| 4,692,160 A | 9/1987 | Nussbaumer | |
| 4,707,864 A | 11/1987 | Ikematsu et al. | |
| 4,713,066 A | 12/1987 | Komis | |
| 4,747,166 A * | 5/1988 | Kuntz | A61F 5/455 4/144.1 |
| 4,752,944 A | 6/1988 | Conrads et al. | |
| 4,769,215 A | 9/1988 | Ehrenkranz | |
| 4,772,280 A | 9/1988 | Rooyakkers | |
| 4,790,835 A | 12/1988 | Elias | |
| 4,791,686 A | 12/1988 | Taniguchi et al. | |
| 4,795,449 A | 1/1989 | Schneider et al. | |
| 4,799,928 A | 1/1989 | Crowley | |
| 4,804,377 A | 2/1989 | Hanifl et al. | |
| 4,820,297 A | 4/1989 | Kaufman et al. | |
| 4,846,818 A | 7/1989 | Keldahl et al. | |
| 4,846,909 A | 7/1989 | Klug et al. | |
| 4,882,794 A | 11/1989 | Stewart, III | |
| 4,883,465 A | 11/1989 | Brennan | |
| 4,886,508 A | 12/1989 | Washington | |
| 4,886,509 A | 12/1989 | Mattsson | |
| 4,889,533 A | 12/1989 | Beecher | |
| 4,905,692 A | 3/1990 | More | |
| 4,955,922 A | 9/1990 | Terauchi | |
| 4,965,460 A | 10/1990 | Tanaka et al. | |
| 5,002,541 A | 3/1991 | Conkling et al. | |
| 5,004,463 A | 4/1991 | Nigay | |
| 5,031,248 A * | 7/1991 | Kemper | A41B 9/008 2/406 |
| 5,045,077 A | 9/1991 | Blake | |
| 5,049,144 A | 9/1991 | Payton | |
| 5,071,347 A | 12/1991 | Mcguire | |

(56) References Cited

U.S. PATENT DOCUMENTS

| | | |
|---|---|---|
| 5,084,037 A | 1/1992 | Barnett |
| 5,100,396 A | 3/1992 | Zamierowski |
| 5,147,301 A | 9/1992 | Ruvio |
| 5,195,997 A | 3/1993 | Carns |
| 5,203,699 A | 4/1993 | Mcguire |
| 5,244,458 A | 9/1993 | Takasu |
| 5,267,988 A | 12/1993 | Farkas |
| 5,275,307 A | 1/1994 | Freese |
| 5,294,983 A | 3/1994 | Ersoz et al. |
| 5,295,983 A | 3/1994 | Kubo |
| 5,300,052 A | 4/1994 | Kubo |
| 5,382,244 A | 1/1995 | Telang |
| 5,423,784 A | 6/1995 | Metz |
| 5,466,229 A | 11/1995 | Elson et al. |
| 5,478,334 A | 12/1995 | Bernstein |
| 5,499,977 A | 3/1996 | Marx |
| 5,543,042 A | 8/1996 | Filan et al. |
| D373,928 S | 9/1996 | Green |
| 5,618,277 A | 4/1997 | Goulter |
| 5,628,735 A | 5/1997 | Skow |
| 5,636,643 A | 6/1997 | Argenta et al. |
| 5,637,104 A | 6/1997 | Ball et al. |
| 5,674,212 A | 10/1997 | Osborn, III et al. |
| 5,678,564 A * | 10/1997 | Lawrence ............... A61F 5/455 |
| | | 600/574 |
| 5,678,654 A | 10/1997 | Uzawa |
| 5,687,429 A | 11/1997 | Rahlff |
| 5,695,485 A | 12/1997 | Duperret et al. |
| 5,752,944 A | 5/1998 | Dann et al. |
| 5,772,644 A | 6/1998 | Bark et al. |
| 5,827,247 A | 10/1998 | Kay |
| 5,827,250 A | 10/1998 | Fujioka et al. |
| 5,827,257 A | 10/1998 | Fujioka et al. |
| D401,699 S | 11/1998 | Herchenbach et al. |
| 5,865,378 A | 2/1999 | Hollinshead et al. |
| 5,887,291 A | 3/1999 | Bellizzi |
| 5,894,608 A | 4/1999 | Birbara |
| D409,303 S | 5/1999 | Oepping |
| 5,911,222 A | 6/1999 | Lawrence et al. |
| 5,957,904 A | 9/1999 | Holland |
| 5,972,505 A | 10/1999 | Phillips et al. |
| 6,059,762 A | 5/2000 | Boyer et al. |
| 6,063,064 A | 5/2000 | Tuckey et al. |
| 6,105,174 A | 8/2000 | Karlsten et al. |
| 6,113,582 A | 9/2000 | Dwork |
| 6,117,163 A | 9/2000 | Bierman |
| 6,123,398 A | 9/2000 | Arai et al. |
| 6,129,718 A | 10/2000 | Wada et al. |
| 6,131,964 A | 10/2000 | Sareshwala |
| 6,152,902 A | 11/2000 | Christian et al. |
| 6,164,569 A | 12/2000 | Hollinshead et al. |
| 6,177,606 B1 | 1/2001 | Etheredge et al. |
| 6,209,142 B1 | 4/2001 | Mattsson et al. |
| 6,248,096 B1 | 6/2001 | Dwork et al. |
| 6,311,339 B1 | 11/2001 | Kraus |
| 6,336,919 B1 | 1/2002 | Davis et al. |
| 6,338,729 B1 | 1/2002 | Wada et al. |
| 6,409,712 B1 | 6/2002 | Dutari et al. |
| 6,416,500 B1 | 7/2002 | Wada et al. |
| 6,428,521 B1 | 8/2002 | Droll |
| 6,475,198 B1 | 11/2002 | Lipman et al. |
| 6,479,726 B1 | 11/2002 | Cole et al. |
| 6,491,673 B1 | 12/2002 | Palumbo et al. |
| 6,508,794 B1 | 1/2003 | Palumbo et al. |
| 6,540,729 B1 | 4/2003 | Wada et al. |
| 6,547,771 B2 | 4/2003 | Robertson et al. |
| 6,569,133 B2 | 5/2003 | Cheng et al. |
| D476,518 S | 7/2003 | Doppelt |
| 6,592,560 B2 | 7/2003 | Snyder et al. |
| 6,618,868 B2 | 9/2003 | Minnick |
| 6,620,142 B1 | 9/2003 | Flueckiger |
| 6,629,651 B1 | 10/2003 | Male et al. |
| 6,635,038 B2 | 10/2003 | Scovel |
| 6,652,495 B1 | 11/2003 | Walker |
| 6,685,684 B1 | 2/2004 | Falconer |
| 6,702,793 B1 | 3/2004 | Sweetser et al. |
| 6,706,027 B2 | 3/2004 | Harvie et al. |
| 6,732,384 B2 | 5/2004 | Scott |
| 6,740,066 B2 | 5/2004 | Wolff et al. |
| 6,764,477 B1 | 7/2004 | Chen et al. |
| 6,783,519 B2 | 8/2004 | Samuelsson |
| 6,796,974 B2 | 9/2004 | Palumbo et al. |
| 6,814,547 B2 | 11/2004 | Childers et al. |
| 6,849,065 B2 | 2/2005 | Schmidt et al. |
| 6,857,137 B2 | 2/2005 | Otto |
| 6,885,690 B2 | 4/2005 | Aggerstam et al. |
| 6,888,044 B2 | 5/2005 | Fell et al. |
| 6,912,737 B2 | 7/2005 | Ernest et al. |
| 6,918,899 B2 | 7/2005 | Harvie |
| 6,979,324 B2 | 12/2005 | Bybordi et al. |
| 7,018,366 B2 | 3/2006 | Easter |
| 7,066,411 B2 | 6/2006 | Male et al. |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| D533,972 S | 12/2006 | La |
| 7,171,699 B2 | 2/2007 | Ernest et al. |
| 7,171,871 B2 | 2/2007 | Kozak |
| 7,179,951 B2 | 2/2007 | Krishnaswamy-mirle et al. |
| 7,181,781 B1 | 2/2007 | Trabold et al. |
| 7,186,245 B1 | 3/2007 | Cheng et al. |
| 7,192,424 B2 | 3/2007 | Cooper |
| 7,220,250 B2 | 5/2007 | Suzuki et al. |
| D562,975 S | 2/2008 | Otto |
| 7,335,189 B2 | 2/2008 | Harvie |
| 7,358,282 B2 | 4/2008 | Krueger et al. |
| 7,390,320 B2 | 6/2008 | Machida et al. |
| 7,488,310 B2 | 2/2009 | Yang |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,588,560 B1 | 9/2009 | Dunlop |
| 7,665,359 B2 | 2/2010 | Barber |
| 7,682,347 B2 | 3/2010 | Parks et al. |
| 7,687,004 B2 | 3/2010 | Allen |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 | 7/2010 | Tazoe et al. |
| 7,755,497 B2 | 7/2010 | Wada et al. |
| 7,766,887 B2 | 8/2010 | Burns, Jr. et al. |
| D625,407 S | 10/2010 | Koizumi et al. |
| 7,806,879 B2 | 10/2010 | Brooks et al. |
| 7,815,067 B2 | 10/2010 | Matsumoto et al. |
| 7,833,169 B2 | 11/2010 | Hannon |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 * | 3/2011 | Mombrinie ............ A61M 1/008 |
| | | 604/317 |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,993,318 B2 | 8/2011 | Olsson et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |

(56) References Cited

U.S. PATENT DOCUMENTS

| | | |
|---|---|---|
| 8,241,262 B2 | 8/2012 | Mahnensmith |
| 8,277,426 B2 | 10/2012 | Wilcox et al. |
| 8,287,508 B1 * | 10/2012 | Sanchez ............... A61F 5/4404 604/319 |
| 8,303,554 B2 * | 11/2012 | Tsai ....................... A61F 5/453 604/319 |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |
| 8,353,074 B2 | 1/2013 | Krebs |
| 8,353,886 B2 | 1/2013 | Bester et al. |
| D676,241 S | 2/2013 | Merrill |
| 8,388,588 B2 | 3/2013 | Wada et al. |
| D679,807 S | 4/2013 | Burgess et al. |
| 8,425,482 B2 | 4/2013 | Khoubnazar |
| 8,449,510 B2 | 5/2013 | Martini et al. |
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,546,639 B2 | 10/2013 | Wada et al. |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,652,112 B2 | 2/2014 | Johannison et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,864,730 B2 | 10/2014 | Conway et al. |
| 8,881,923 B2 | 11/2014 | Higginson |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,173,602 B2 | 11/2015 | Gilbert |
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,382,047 B2 | 7/2016 | Schmidtner et al. |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |
| 9,555,930 B2 | 1/2017 | Campbell et al. |
| D789,522 S | 6/2017 | Burgess et al. |
| 9,687,849 B2 | 6/2017 | Bruno et al. |
| 9,694,949 B2 | 7/2017 | Hendricks et al. |
| 9,788,992 B2 | 10/2017 | Harvie |
| D804,907 S | 12/2017 | Sandoval |
| 9,868,564 B2 | 1/2018 | Mcgirr et al. |
| D814,239 S | 4/2018 | Arora |
| D817,484 S | 5/2018 | Lafond |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Perez Martinez |
| 10,226,376 B2 | 3/2019 | Sanchez et al. |
| D848,612 S | 5/2019 | Mozzicato et al. |
| 10,335,121 B2 | 7/2019 | Desai |
| D856,512 S | 8/2019 | Cowart et al. |
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Villarreal |
| 10,407,222 B2 | 9/2019 | Allen |
| 10,478,356 B2 | 11/2019 | Griffin |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| D901,214 S | 11/2020 | Hu |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |
| 10,973,678 B2 | 4/2021 | Newton et al. |
| 10,974,874 B2 | 4/2021 | Ragias et al. |
| D923,365 S | 6/2021 | Wang |
| 11,027,900 B2 | 6/2021 | Liu |
| 11,045,346 B2 | 6/2021 | Argent et al. |
| D928,946 S | 8/2021 | Sanchez et al. |
| 2001/0054426 A1 | 12/2001 | Knudson et al. |
| 2002/0019614 A1 | 2/2002 | Woon |
| 2002/0026161 A1 | 2/2002 | Grundke |
| 2002/0087131 A1 | 7/2002 | Wolff et al. |
| 2002/0189992 A1 | 12/2002 | Schmidt et al. |
| 2003/0004436 A1 | 1/2003 | Schmidt et al. |
| 2003/0120178 A1 | 6/2003 | Heki |
| 2003/0157859 A1 | 8/2003 | Ishikawa |
| 2003/0181880 A1 | 9/2003 | Schwartz |
| 2003/0195484 A1 * | 10/2003 | Harvie ................... A61F 5/453 604/355 |
| 2003/0233079 A1 | 12/2003 | Parks et al. |
| 2004/0006321 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 | 7/2004 | Easter |
| 2004/0176731 A1 | 9/2004 | Cheng et al. |
| 2004/0191919 A1 | 9/2004 | Unger et al. |
| 2004/0207530 A1 | 10/2004 | Nielsen |
| 2004/0236292 A1 | 11/2004 | Tazoe et al. |
| 2004/0254547 A1 | 12/2004 | Okabe et al. |
| 2005/0010182 A1 | 1/2005 | Parks et al. |
| 2005/0033248 A1 | 2/2005 | Machida et al. |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0137557 A1 | 6/2005 | Swiecicki et al. |
| 2005/0177070 A1 | 8/2005 | Levinson et al. |
| 2005/0197639 A1 | 9/2005 | Mombrinie |
| 2005/0277904 A1 | 12/2005 | Chase et al. |
| 2005/0279359 A1 | 12/2005 | LeBlanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0111648 A1 | 5/2006 | Vermaak |
| 2006/0155214 A1 | 7/2006 | Wightman |
| 2006/0200102 A1 | 9/2006 | Cooper |
| 2006/0229576 A1 | 10/2006 | Conway et al. |
| 2006/0231648 A1 | 10/2006 | Male et al. |
| 2006/0235359 A1 | 10/2006 | Marland |
| 2007/0006368 A1 | 1/2007 | Key et al. |

(56) References Cited

U.S. PATENT DOCUMENTS

| | | |
|---|---|---|
| 2007/0038194 A1 | 2/2007 | Wada et al. |
| 2007/0117880 A1 | 5/2007 | Elson et al. |
| 2007/0135786 A1 | 6/2007 | Schmidt et al. |
| 2007/0149935 A1 | 6/2007 | Dirico |
| 2007/0191804 A1 | 8/2007 | Coley |
| 2007/0214553 A1 | 9/2007 | Carromba et al. |
| 2007/0266486 A1 | 11/2007 | Ramirez |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0091153 A1 | 4/2008 | Harvie |
| 2008/0091158 A1 | 4/2008 | Yang |
| 2008/0234642 A1 | 9/2008 | Patterson et al. |
| 2008/0281282 A1 | 11/2008 | Finger et al. |
| 2008/0287894 A1 | 11/2008 | Van Den Heuvel et al. |
| 2009/0025717 A1 | 1/2009 | Pinel |
| 2009/0056003 A1 | 3/2009 | Ivie et al. |
| 2009/0192482 A1 | 7/2009 | Dodge et al. |
| 2009/0234312 A1 | 9/2009 | Otoole et al. |
| 2009/0251510 A1 | 10/2009 | Noro et al. |
| 2009/0264840 A1 | 10/2009 | Virginio |
| 2009/0270822 A1 | 10/2009 | Medeiros |
| 2009/0281510 A1 | 11/2009 | Fisher |
| 2010/0004612 A1 | 1/2010 | Thevenin |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060300 A1 | 3/2011 | Weig et al. |
| 2011/0077495 A1 | 3/2011 | Gilbert |
| 2011/0137273 A1 | 6/2011 | Muellejans et al. |
| 2011/0172620 A1 | 7/2011 | Khambatta |
| 2011/0172625 A1 | 7/2011 | Wada et al. |
| 2011/0202024 A1 | 8/2011 | Cozzens |
| 2011/0240648 A1 | 10/2011 | Tucker |
| 2012/0035577 A1 | 2/2012 | Tomes et al. |
| 2012/0103347 A1 | 5/2012 | Wheaton et al. |
| 2012/0165768 A1 | 6/2012 | Sekiyama et al. |
| 2012/0165786 A1 | 6/2012 | Chappa et al. |
| 2012/0210503 A1 | 8/2012 | Anzivino et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0330256 A1 | 12/2012 | Wilcox et al. |
| 2013/0006206 A1 | 1/2013 | Wada et al. |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0292537 A1 | 11/2013 | Dirico |
| 2014/0031774 A1 | 1/2014 | Bengtson |
| 2014/0157499 A1 | 6/2014 | Suzuki et al. |
| 2014/0182051 A1 | 7/2014 | Tanimoto et al. |
| 2014/0196189 A1 | 7/2014 | Lee et al. |
| 2014/0276501 A1 | 9/2014 | Cisko |
| 2014/0316381 A1 | 10/2014 | Reglin |
| 2014/0325746 A1 | 11/2014 | Block |
| 2014/0348139 A1 | 11/2014 | Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209194 A1 | 7/2015 | Heyman |
| 2015/0329255 A1 | 11/2015 | Rzepecki |
| 2015/0359660 A1 | 12/2015 | Harvie |
| 2015/0366699 A1 | 12/2015 | Nelson |
| 2016/0029998 A1 | 2/2016 | Brister et al. |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0278662 A1 | 9/2016 | Brister et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0374848 A1 | 12/2016 | Sanchez et al. |
| 2017/0007438 A1 | 1/2017 | Harvie |
| 2017/0143534 A1 | 5/2017 | Sanchez |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1 | 9/2017 | Sanchez et al. |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0042748 A1 | 12/2017 | Griffin |
| 2017/0348139 A1 | 12/2017 | Newton et al. |
| 2017/0354532 A1 | 12/2017 | Holt |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0127187 A1 | 5/2018 | Sewell |
| 2018/0200101 A1 | 7/2018 | Su |
| 2018/0228642 A1 | 8/2018 | Davis et al. |
| 2019/0021899 A1 | 1/2019 | Vlet |
| 2019/0038451 A1 | 2/2019 | Harvie |
| 2019/0100362 A1 | 4/2019 | Meyers et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0247222 A1 | 8/2019 | Ecklund et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085610 A1 | 3/2020 | Cohn et al. |
| 2020/0229964 A1 | 7/2020 | Staali et al. |
| 2020/0231343 A1 | 7/2020 | Freedman et al. |
| 2020/0255189 A1 | 8/2020 | Liu |
| 2020/0331672 A1 | 10/2020 | Bertram et al. |
| 2020/0367677 A1 | 11/2020 | Silsby et al. |
| 2020/0369444 A1 | 11/2020 | Silsby et al. |
| 2020/0385179 A1 | 12/2020 | Mccourt |
| 2020/0390592 A1 | 12/2020 | Merrill |
| 2021/0008771 A1 | 1/2021 | Huber et al. |
| 2021/0009323 A1 | 1/2021 | Markarian et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0121318 A1 | 4/2021 | Pinlac |
| 2021/0154055 A1 | 5/2021 | Villarreal |

(56) References Cited

U.S. PATENT DOCUMENTS

| | | | |
|---|---|---|---|
| 2021/0220162 A1 | 7/2021 | Jamison | |
| 2021/0220163 A1 | 7/2021 | Mayrand | |
| 2021/0229877 A1 | 7/2021 | Ragias et al. | |

FOREIGN PATENT DOCUMENTS

| | | | |
|---|---|---|---|
| CN | 1332620 | A | 1/2002 |
| CN | 1533755 | A | 10/2004 |
| CN | 1602825 | A | 4/2005 |
| CN | 1720888 | A | 1/2006 |
| CN | 101262836 | A | 9/2008 |
| CN | 202184840 | U | 4/2012 |
| CN | 103717180 | A | 4/2014 |
| CN | 107847384 | A | 3/2018 |
| DE | 79818 | C | 10/1893 |
| DE | 1516466 | A1 | 6/1969 |
| DE | 9407554.9 | U1 | 5/1995 |
| DE | 4443710 | A1 | 6/1995 |
| DE | 19619597 | A1 | 11/1997 |
| DE | 102011103783 | A1 | 12/2012 |
| DK | 9600118 | | 11/1996 |
| EP | 0032138 | A2 | 7/1981 |
| EP | 0066070 | B1 | 12/1982 |
| EP | 0119143 | B1 | 11/1988 |
| EP | 0610638 | A1 | 8/1994 |
| EP | 0613355 | A1 | 9/1994 |
| EP | 0613355 | B1 | 1/1997 |
| EP | 1332738 | A1 | 8/2003 |
| EP | 1382318 | A1 | 1/2004 |
| EP | 1382318 | B1 | 5/2006 |
| EP | 2180907 | A1 | 5/2010 |
| EP | 2380532 | A1 | 10/2011 |
| EP | 2879534 | B1 | 3/2017 |
| EP | 3424471 | A1 | 1/2019 |
| EP | 3169292 | B1 | 11/2019 |
| GB | 1011517 | A | 12/1965 |
| GB | 1467144 | A | 3/1977 |
| GB | 2106395 | A | 4/1983 |
| GB | 2171315 | A | 8/1986 |
| GB | 2148126 | B | 7/1987 |
| GB | 2191095 | A | 12/1987 |
| GB | 2199750 | A | 7/1988 |
| GB | 2260907 | A | 5/1993 |
| GB | 2462267 | A | 2/2010 |
| GB | 2469496 | A | 10/2010 |
| JP | S5410596 | A | 1/1979 |
| JP | S5410596 | Y2 | 5/1979 |
| JP | S5888596 | U | 6/1983 |
| JP | S63107780 | U | 7/1988 |
| JP | H0267530 | A | 3/1990 |
| JP | H02103871 | A | 4/1990 |
| JP | H0460220 | A | 2/1992 |
| JP | H04060220 | U | 2/1992 |
| JP | H05123349 | A | 5/1993 |
| JP | H1040141 | A | 2/1998 |
| JP | H11113946 | A | 4/1999 |
| JP | H11290365 | A | 10/1999 |
| JP | 2000185068 | A | 7/2000 |
| JP | 3087938 | B2 | 9/2000 |
| JP | 2001054531 | A | 2/2001 |
| JP | 2001276107 | A | 10/2001 |
| JP | 2001276108 | A | 10/2001 |
| JP | 2004130056 | A | 4/2004 |
| JP | 2004267530 | A | 9/2004 |
| JP | 2005066325 | A | 3/2005 |
| JP | 2006026108 | A | 2/2006 |
| JP | 3123547 | B2 | 6/2006 |
| JP | 2006204868 | A | 8/2006 |
| JP | 3132659 | B2 | 5/2007 |
| JP | 4039641 | B2 | 11/2007 |
| JP | 4747166 | B2 | 5/2011 |
| JP | 2011224070 | A | 11/2011 |
| JP | 2012523869 | A | 10/2012 |
| JP | 2015092945 | A | 5/2015 |
| JP | 3198994 | B2 | 7/2015 |
| KR | 101432639 | B1 | 8/2014 |
| WO | 8101957 | A1 | 7/1981 |
| WO | 8804558 | A1 | 6/1988 |
| WO | 9104714 | A2 | 4/1991 |
| WO | 9104714 | A3 | 6/1991 |
| WO | 9220299 | A3 | 2/1993 |
| WO | 9309736 | A2 | 5/1993 |
| WO | 9309736 | A3 | 6/1993 |
| WO | 9600096 | A1 | 1/1996 |
| WO | 9634636 | A1 | 11/1996 |
| WO | 9817211 | A1 | 4/1998 |
| WO | 9830336 | A1 | 7/1998 |
| WO | 0000112 | A1 | 1/2000 |
| WO | 0000113 | A1 | 1/2000 |
| WO | 0033773 | A1 | 6/2000 |
| WO | 0057784 | A1 | 10/2000 |
| WO | 0145618 | A1 | 6/2001 |
| WO | 0145621 | A1 | 6/2001 |
| WO | 02094160 | A1 | 11/2002 |
| WO | 03013967 | A1 | 2/2003 |
| WO | 03024824 | A1 | 3/2003 |
| WO | 03071931 | A2 | 9/2003 |
| WO | 03079942 | A1 | 10/2003 |
| WO | 03071931 | A3 | 2/2004 |
| WO | 2004019836 | A1 | 3/2004 |
| WO | 2005074571 | A3 | 9/2005 |
| WO | 2005089687 | A2 | 9/2005 |
| WO | 2005107661 | A2 | 11/2005 |
| WO | 2007007845 | A1 | 1/2007 |
| WO | 2007042823 | A2 | 4/2007 |
| WO | 2007055651 | A1 | 5/2007 |
| WO | 2006098950 | A3 | 11/2007 |
| WO | 2007134608 | A2 | 11/2007 |
| WO | 2007128156 | A3 | 2/2008 |
| WO | 2008078117 | A1 | 7/2008 |
| WO | 2008104019 | A1 | 9/2008 |
| WO | 2008141471 | A1 | 11/2008 |
| WO | 2009004368 | A1 | 1/2009 |
| WO | 2009004369 | A1 | 1/2009 |
| WO | 2009052496 | A1 | 4/2009 |
| WO | 2009007702 | A4 | 7/2009 |
| WO | 2009101738 | A1 | 8/2009 |
| WO | 2010058192 | A1 | 5/2010 |
| WO | 2010030122 | A3 | 7/2010 |
| WO | 2010101915 | A3 | 1/2011 |
| WO | 2011018132 | A1 | 2/2011 |
| WO | 2011018133 | A1 | 2/2011 |
| WO | 2011024864 | A1 | 3/2011 |
| WO | 2011054118 | A1 | 5/2011 |
| WO | 2011107972 | A1 | 9/2011 |
| WO | 2011108972 | A1 | 9/2011 |
| WO | 2011117292 | A1 | 9/2011 |
| WO | 2011123219 | A1 | 10/2011 |
| WO | 2011132043 | A1 | 10/2011 |
| WO | 2012012908 | A1 | 2/2012 |
| WO | 2012065274 | A1 | 5/2012 |
| WO | 2012097462 | A1 | 7/2012 |
| WO | 2012098796 | A1 | 7/2012 |
| WO | 2012101288 | A1 | 8/2012 |
| WO | 2012175916 | A1 | 12/2012 |
| WO | 2013018435 | A1 | 2/2013 |
| WO | 2013033429 | A1 | 3/2013 |
| WO | 2013055434 | A1 | 4/2013 |
| WO | 2013103291 | A2 | 7/2013 |
| WO | 2013131109 | A1 | 9/2013 |
| WO | 2013167478 | A1 | 11/2013 |
| WO | 2013177716 | A1 | 12/2013 |
| WO | 2014041534 | A1 | 3/2014 |
| WO | 2014046420 | A1 | 3/2014 |
| WO | 2014118518 | A1 | 8/2014 |
| WO | 2014160852 | A1 | 10/2014 |
| WO | 2015023599 | A1 | 2/2015 |
| WO | 2015052348 | A1 | 4/2015 |
| WO | 2015068384 | A1 | 5/2015 |
| WO | 2015169403 | A1 | 11/2015 |
| WO | 2015170307 | A1 | 11/2015 |
| WO | 2015197462 | A1 | 12/2015 |
| WO | 2016051385 | A1 | 4/2016 |
| WO | 2016055989 | A1 | 4/2016 |

(56) References Cited

FOREIGN PATENT DOCUMENTS

| WO | 2016071894 A1 | 5/2016 |
| --- | --- | --- |
| WO | 2016103242 A1 | 6/2016 |
| WO | 2016116915 A1 | 7/2016 |
| WO | 2016124203 A1 | 8/2016 |
| WO | 2016139448 A1 | 9/2016 |
| WO | 2016166562 A1 | 10/2016 |
| WO | 2016167535 A1 | 10/2016 |
| WO | 2016191574 A1 | 12/2016 |
| WO | 2016200088 A1 | 12/2016 |
| WO | 2016200361 A1 | 12/2016 |
| WO | 2016204731 A1 | 12/2016 |
| WO | 2017001846 A1 | 1/2017 |
| WO | 2017152198 A1 | 9/2017 |
| WO | 2017162559 A1 | 9/2017 |
| WO | 2017205446 A1 | 11/2017 |
| WO | 2017209779 A1 | 12/2017 |
| WO | 2017210524 A1 | 12/2017 |
| WO | 2018022414 A1 | 2/2018 |
| WO | 2018044781 A1 | 3/2018 |
| WO | 2018056953 A1 | 3/2018 |
| WO | 2018090550 A1 | 5/2018 |
| WO | 2018138513 A1 | 8/2018 |
| WO | 2018144463 A1 | 8/2018 |
| WO | 2018152156 A1 | 8/2018 |
| WO | 2018183791 A1 | 10/2018 |
| WO | 2018235026 A1 | 12/2018 |
| WO | 2018235065 A1 | 12/2018 |
| WO | 2019096845 A1 | 5/2019 |
| WO | 2019190593 A1 | 10/2019 |
| WO | 2019212949 A1 | 11/2019 |
| WO | 2019212950 A1 | 11/2019 |
| WO | 2019212951 A1 | 11/2019 |
| WO | 2019212952 A1 | 11/2019 |
| WO | 2019212954 A1 | 11/2019 |
| WO | 2019212955 A1 | 11/2019 |
| WO | 2019212956 A1 | 11/2019 |
| WO | 2019214788 A1 | 11/2019 |
| WO | 2020000994 A1 | 1/2020 |
| WO | 2020020618 A1 | 1/2020 |
| WO | 2020038822 A1 | 2/2020 |
| WO | 2020088409 A1 | 5/2020 |
| WO | 2020049394 A3 | 6/2020 |
| WO | 2020120657 A1 | 6/2020 |
| WO | 2020152575 A1 | 7/2020 |
| WO | 2020182923 A1 | 9/2020 |
| WO | 2021007144 A1 | 1/2021 |
| WO | 2021007345 A1 | 1/2021 |
| WO | 2021010844 A1 | 1/2021 |
| WO | 2021016026 A1 | 1/2021 |
| WO | 2021016300 A1 | 1/2021 |
| WO | 2021034886 A1 | 2/2021 |
| WO | 2021041123 A1 | 3/2021 |
| WO | 2021094352 A1 | 5/2021 |
| WO | 2021155206 A1 | 8/2021 |
| WO | 2021257202 A1 | 12/2021 |
| WO | 2022006256 A1 | 1/2022 |

OTHER PUBLICATIONS

Advisory Action for U.S. Appl. No. 14/722,613 dated Mar. 4, 2019.
Advisory Action for U.S. Appl. No. 14/952,591 dated Jun. 1, 2018.
Advisory Action for U.S. Appl. No. 15/238,427 dated Apr. 10, 2019.
Corrected International Search Report and Written Opinion for International Application No. PCT/US2017/043025 dated Jan. 11, 2018.
Corrected Notice of Allowability for U.S. Appl. No. 15/221,106 dated Jul. 2, 2019.
Final Office Action for U.S. Appl. No. 14/722,613 dated Nov. 29, 2018.
Final Office Action for U.S. Appl. No. 14/947,759 dated Apr. 8, 2016.
Final Office Action for U.S. Appl. No. 14/952,591 dated Feb. 23, 2018.
Final Office Action for U.S. Appl. No. 14/952,591 dated Nov. 1, 2019.
Final Office Action for U.S. Appl. No. 15/171,968 dated Feb. 14, 2020.
Final Office Action for U.S. Appl. No. 15/171,968 dated Mar. 19, 2019.
Final Office Action for U.S. Appl. No. 15/221,106 dated Jan. 23, 2019.
Final Office Action for U.S. Appl. No. 15/238,427 dated Jan. 2, 2019.
Final Office Action for U.S. Appl. No. 15/260,103 dated Feb. 14, 2019.
Final Office Action for U.S. Appl. No. 15/612,325 dated Sep. 17, 2020.
Final Office Action for U.S. Appl. No. 29/624,661 dated Feb. 18, 2020.
International Search Report and Written Opinion from International Application No. PCT/US2016/049274 dated Dec. 1, 2016.
International Search Report and Written Opinion from International Application No. PCT/US2017/035625 dated Aug. 15, 2017.
International Search Report and Written Opinion from International Application No. PCT/US2017/043025 dated Oct. 18, 2017.
International Search Report and Written Opinion from International Application No. PCT/US2018/015968 dated Apr. 6, 2018.
International Search Report and Written Opinion from International Application No. PCT/US2019/029608 dated Sep. 3, 2019.
International Search Report and Written Opinion from International Application No. PCT/US2019/029609 dated Sep. 3, 2019.
International Search Report and Written Opinion from International Application No. PCT/US2019/029610 dated Sep. 3, 2019.
International Search Report and Written Opinion from International Application No. PCT/US2019/029611 dated Jul. 3, 2019.
International Search Report and Written Opinion from International Application No. PCT/US2019/029613 dated Jul. 3, 2019.
International Search Report and Written Opinion from International Application No. PCT/US2019/029614 dated Sep. 26, 2019.
International Search Report and Written Opinion from International Application No. PCT/US2019/029616 dated Aug. 30, 2019.
International Search Report and Written Opinion from International Application No. PCT/US2020/023572 dated Jul. 6, 2020.
Issue Notification for U.S. Appl. No. 15/221,106 dated Jul. 24, 2019.
Issue Notification for U.S. Appl. No. 15/238,427 dated Jul. 24, 2019.
Issue Notification for U.S. Appl. No. 15/260,103 dated Aug. 7, 2019.
Issue Notification for U.S. Appl. No. 15/611,587 dated Feb. 20, 2019.
Non-Final Office Action for U.S. Appl. No. 14/722,613 dated Jun. 13, 2019.
Non-Final Office Action for U.S. Appl. No. 14/947,759, dated Mar. 17, 2016.
Non-Final Office Action for U.S. Appl. No. 14/952,591 dated Aug. 1, 2017.
Non-Final Office Action for U.S. Appl. No. 14/952,591 dated Mar. 20, 2020.
Non-Final Office Action for U.S. Appl. No. 14/952,591 dated Mar. 21, 2019.
Non-Final Office Action for U.S. Appl. No. 14/952,591 dated Sep. 28, 2018.
Non-Final Office Action for U.S. Appl. No. 15/171,968 dated May 11, 2020.
Non-Final Office Action for U.S. Appl. No. 15/171,968 dated Aug. 20, 2019.
Non-Final Office Action for U.S. Appl. No. 15/171,968 dated Jun. 12, 2018.
Non-Final Office Action for U.S. Appl. No. 15/221,106 dated Jun. 5, 2018.
Non-Final Office Action for U.S. Appl. No. 15/238,427 dated Aug. 8, 2018.
Non-Final Office Action for U.S. Appl. No. 15/260,103 dated Sep. 26, 2018.

(56) References Cited

OTHER PUBLICATIONS

Non-Final Office Action for U.S. Appl. No. 15/611,587 dated Dec. 29, 2017.
Non-Final Office Action for U.S. Appl. No. 15/611,587 dated Jul. 13, 2018.
Non-Final Office Action for U.S. Appl. No. 15/612,325 dated Mar. 19, 2020.
Non-Final Office Action for U.S. Appl. No. 16/899,956 dated Oct. 16, 2020.
Non-Final Office Action for U.S. Appl. No. 29/624,661 dated Jul. 18, 2019.
Non-Final Office Action for U.S. Appl. No. 29/694,002 dated Jun. 24, 2020.
Notice of Allowance for U.S. Appl. No. 15/221,106 dated May 1, 2019.
Notice of Allowance for U.S. Appl. No. 15/238,427 dated May 23, 2019.
Notice of Allowance for U.S. Appl. No. 15/260,103 dated Jun. 7, 2019.
Notice of Allowance for U.S. Appl. No. 15/611,587 dated Dec. 21, 2018.
Notice of Allowance for U.S. Appl. No. 29/624,661 dated Jul. 10, 2020.
Notice of Allowance for U.S. Appl. No. 29/624,661 dated May 14, 2020.
Notice of Allowance for U.S. Appl. No. 29/624,661 dated Sep. 29, 2020.
Notice of Allowance for U.S. Appl. No. 29/694,002 dated Oct. 16, 2020.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/611,587, filed Jun. 1, 2017.
U.S. Appl. No. 15/612,325, filed Jun. 2, 2017.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 29/741,751, filed Jul. 15, 2020.
U.S. Appl. No. 62/452,437, filed Jan. 31, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,889, filed May 29, 2019.
U.S. Appl. No. 62/873,045, filed Jul. 11, 2019.
U.S. Appl. No. 62/873,048, filed Jul. 11, 2019.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/071,438, filed Aug. 28, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
Defendant and Counterclaim Plaintiff Sage Products, LLC's Answer, Defenses, and Counterclaims to Plaintiff's Amended Complaint, Nov. 1, 2019.
Sage's Initial Invalidity Contentions Regarding U.S. Pat. No. 8,287,508; U.S. Pat. No. 10,226,375; and U.S. Pat. No. 10,390,989, May 29, 2020, 193 pages.
Sage's Supplemental and Initial Invalidity Contentions Regarding U.S. Pat. No. 8,287,508; U.S. Pat. No. 10,226,375; U.S. Pat. No. 10,390,989 and Initial Invalidity Contentions Regarding U.S. Pat. No. 10,376,407, Aug. 21, 2020, 277 pages.
Excerpts from the 508 (U.S. Pat. No. 8,278,508) Patent's Prosecution History, 2020, 99 pages.
Plaintiff's Opening Claim Construction Brief, Case No. 19-1508-MN, Oct. 16, 2020, 26 pages.
Plaintiff's Identification of Claim Terms and Proposed Constructions, Case No. 19-1508-MN, 3 pages.
PureWick's Response to Interrogatory No. 9 in *PureWick, LLC* v. *Sage Products, LLC*, Case No. 19-1508-MN, Mar. 23, 2020, 6 pages.
Sage's Preliminary Identification of Claim Elements and Proposed Constructions for U.S. Pat. No. 8,287,508, U.S. Pat. No. 10,226,376, U.S. Pat. No. 10,390,989 and U.S. Pat. No. 10,376,407, Case No. 19-1508-MN, 7 pages.
Corrected Certificate of Service, Case No. IPR2020-01426, U.S. Pat. No. 8,287,508, 2020, 2 pages.
Declaration of Diane K. Newman Curriculum Vitae, Petition for Interparties Review, 2020, pp. 1-199.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXDmax In-Flight Bladder Relief", Omni Medical; Omni Medical Systems, Inc., 2015.
"AMXDX—Advanced Mission Extender Device Brochure", Omni Medical, Omni Brochure—http://www.omnimedicalsys.com/uploads/AMXDFixedWing.pdf, 2 pages.
"How Period Panties Work", www.shethinx.com/pages/thinx-itworks, 2020, 10 pages.
"In Flight Bladder Relief", Omni Medical, Omni Presentation https://www.omnimedicalsys.com/uploads/AMXDmax_HSD.pdf, 14 pages.
"Research and Development Work Relating to Assistive Technology 2005-06", British Department of Health, Nov. 2006, 40 pages.
"Step by Step How Ur24 WorksHome", http://medicalpatentur24.com, last accessed Dec. 6, 2017, Aug. 30, 2017, 4 pages.
"Underwear that absorbs your period", Thinx!, https://www.shethinx.com/pages/thinx-it-works last accessed Jun. 24, 2020, 7 pages.
Hollister, Female Urinary and Pouch and Male Urinary Pouch Brochure, 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device, last accessed Feb. 8, 2018.
Hollister, "Retracted Penis Pouch by Hollister", Vitality Medical.com, https://www.vitalitymedical.com/hollister-retracted-penis-pouch.html last accessed Jun. 24, 2020, 6 pages.
Macaulay, et al., "A Noninvasive Continence Management System: Development and Evaluation of a Novel Toileting Device for Women", The Wound, Ostomy and Continence Nurses Society, vol. 34 No. 6, 2007, pp. 641-648.
Newman, et al., "The Urinary Incontinence Sourcebook", Petition for Interparties Review, 1997, 23 pages.
Parmar, "10 Finalists Chosen for Dare-to-Dream Medtech Design Challenge (PureWick)", Design Services, Nov. 10, 2014, 3 pages.

(56) References Cited

OTHER PUBLICATIONS

Purewick, "Incontinence Relief for Women", Presentation, Sep. 23, 2015, 7 pages.
Pytlik, "Super Absorbent Polymers", University of Buffalo, http://www.courses.sens.buffalo.edu/ce435/Diapers/Diapers.html, accessed on Feb. 17, 2017.
Sachtman, Noah, "New Relief for Pilots? It Depends", Wired, https://www.wired.com/2008/05/pilot-relief/, 2008, 2 pages.
Corrected Notice of Allowability for U.S. Appl. No. 15/612,325 dated Mar. 17, 2021.
Final Office Action for U.S. Appl. No. 14/952,591 dated Nov. 27, 2020.
Final Office Action for U.S. Appl. No. 16/899,956 dated Apr. 19, 2021.
Final Office Action for U.S. Appl. No. 16/904,868 dated Mar. 26, 2021.
Final Office Action for U.S. Appl. No. 16/905,400 dated Apr. 6, 2021.
Issue Notification for U.S. Appl. No. 15/171,968 dated Mar. 3, 2021.
Issue Notification for U.S. Appl. No. 15/612,325 dated Mar. 24, 2021.
Non-Final Office Action for U.S. Appl. No. 16/904,868 dated Nov. 25, 2020.
Non-Final Office Action for U.S. Appl. No. 16/905,400 dated Dec. 2, 2020.
Notice of Allowance for U.S. Appl. No. 14/952,591 dated Apr. 5, 2021.
Notice of Allowance for U.S. Appl. No. 15/171,968 dated Feb. 16, 2021.
Notice of Allowance for U.S. Appl. No. 15/171,968 dated Nov. 6, 2020.
Notice of Allowance for U.S. Appl. No. 15/612,325 dated Feb. 19, 2021.
Notice of Allowance for U.S. Appl. No. 15/612,325 dated Jan. 21, 2021.
Notice of Allowance for U.S. Appl. No. 29/694,002 dated Jan. 29, 2021.
Notice to File Missing Parts for U.S. Appl. No. 17/179,116 dated Mar. 3, 2021.
U.S. Appl. No. 17/179,116, filed Feb. 18, 2021.
U.S. Appl. No. 63/134,287, filed Jan. 6, 2021.
U.S. Appl. No. 63/134,632, filed Jan. 7, 2021.
U.S. Appl. No. 63/148,723, filed Feb. 12, 2021.
Memorandum Order, Feb. 2021, 14 pgs.
Sage's Second Supplemental Invalidity Contentions Regarding U.S. Pat. No. 8,287,508, U.S. Pat. No. 10,226,375, U.S. Pat. No. 10,390,989, and U.S. Pat. No. 10,376,407, 292 pages.
Boehringer CareDry System—Second Generation for Non-Invasive Urinary Management for Females, Mar. 2021, 3 pgs.
Decision Granting Institution of Inter Partes Review for U.S. Pat. No. 8,287,508, Case No. 2020-01426, Feb. 17, 2021, 39 pages.
"AMXD Control Starter Kit Brochure", https://www.omnimedicalsys.com/index.php?page=products, Omni Medical, 8 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, MD&DI, 2014, 4 pages.
Newton, et al., "Measuring Safety, Effectiveness and Ease of Use of PureWick in the Management of Urinary Incontinence in Bedbound Women: Case Studies", Jan. 8, 2016, 11 pages.
Advisory Action for U.S. Appl. No. 16/899,956 dated Jul. 9, 2021.
Advisory Action for U.S. Appl. No. 16/904,868 dated Jul. 2, 2021.
Advisory Action for U.S. Appl. No. 16/905,400 dated Jun. 9, 2021.
International Search Report and Written Opinion from International Application No. PCT/US2020/033064 dated Aug. 31, 2020.
International Search Report and Written Opinion from International Application No. PCT/US2020/033122 dated Aug. 31, 2020.
International Search Report and Written Opinion from International Application No. PCT/US2020/040860 dated Oct. 2, 2020.
International Search Report and Written Opinion from International Application No. PCT/US2020/041242 dated Nov. 17, 2020.
International Search Report and Written Opinion from International Application No. PCT/US2020/041249 dated Oct. 2, 2020.
International Search Report and Written Opinion from International Application No. PCT/US2020/042262 dated Oct. 14, 2020.
International Search Report and Written Opinion from International Application No. PCT/US2020/043059 dated Oct. 6, 2020.
International Search Report and Written Opinion from International Application No. PCT/US2020/044024 dated Nov. 12, 2020.
International Search Report and Written Opinion from International Application No. PCT/US2020/046914 dated Dec. 1, 2020.
International Search Report and Written Opinion from International Application No. PCT/US2020/055680 dated Dec. 15, 2020.
International Search Report and Written Opinion from International Application No. PCT/US2020/061563 dated Feb. 19, 2021.
International Search Report and Written Opinion from International Application No. PCT/US2020/065234 dated Apr. 12, 2021.
International Search Report and Written Opinion from International Application No. PCT/US2020/067451 dated Mar. 25, 2021.
International Search Report and Written Opinion from International Application No. PCT/US2020/067454 dated Mar. 29, 2021.
International Search Report and Written Opinion from International Application No. PCT/US2020/067455 dated Mar. 26, 2021.
International Search Report and Written Opinion from International Application No. PCT/US2021/015024 dated May 18, 2021.
International Search Report and Written Opinion from International Application No. PCT/US2021/015787 dated May 27, 2021.
International Search Report and Written Opinion from International Application No. PCT/US2021/023001 dated Jun. 21, 2021.
International Search Report and Written Opinion from International Application No. PCT/US2021/024162 dated Jul. 8, 2021.
Search Report and Written Opinion from International Application No. PCT/US2021/027061 dated Jul. 19, 2021.
International Search Report and Written Opinion from International Application No. PCT/US2021/027104 dated Jul. 6, 2021.
International Search Report and Written Opinion from International Application No. PCT/US2021/027314 dated Jul. 6, 2021.
International Search Report and Written Opinion from International Application No. PCT/US2021/027422 dated Aug. 12, 2021.
International Search Report and Written Opinion from International Application No. PCT/US2021/027425 dated Aug. 11, 2021.
International Search Report and Written Opinion from International Application No. PCT/US2021/027913 dated Jul. 12, 2021.
International Search Report and Written Opinion from International Application No. PCT/US2021/027917 dated Aug. 19, 2021.
International Search Report and Written Opinion from International Application No. PCT/US2021/035181 dated Sep. 16, 2021.
Issue Notification for U.S. Appl. No. 14/952,591 dated Jul. 28, 2021.
Issue Notification for U.S. Appl. No. 29/624,661 dated Aug. 4, 2021.
Non-Final Office Action for U.S. Appl. No. 14/592,591 dated Mar. 20, 2020.
Non-Final Office Action for U.S. Appl. No. 16/452,145 dated Sep. 28, 2021.

(56) References Cited

OTHER PUBLICATIONS

Non-Final Office Action for U.S. Appl. No. 16/452,258 dated Sep. 28, 2021.
Non-Final Office Action for U.S. Appl. No. 16/478,180 dated Oct. 22, 2021.
Non-Final Office Action for U.S. Appl. No. 16/899,956 dated Sep. 2, 2021.
Non-Final Office Action for U.S. Appl. No. 16/904,868 dated Oct. 5, 2021.
Non-Final Office Action for U.S. Appl. No. 16/905,400 dated Jul. 22, 2021.
Non-Final Office Action for U.S. Appl. No. 17/330,657 dated Aug. 11, 2021.
Notice of Allowance for U.S. Appl. No. 14/952,591 dated Jul. 8, 2021.
Notice of Allowance for U.S. Appl. No. 29/624,661 dated Apr. 28, 2021.
Notice of Allowance for U.S. Appl. No. 29/694,002 dated Apr. 29, 2021.
Restriction Requirement for U.S. Appl. No. 16/478,180 dated May 25, 2021.
U.S. Appl. No. 14/625,469, filed Feb. 28, 2015,.
U.S. Appl. No. 14/947,759, filed Nov. 20, 2015.
U.S. Appl. No. 14/952,591, filed Nov. 25, 2015.
U.S. Appl. No. 16/245,726, filed Jan. 11, 2019.
U.S. Appl. No. 17/330,657, filed May 26, 2021.
U.S. Appl. No. 17/378,015, filed Jul. 16, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/461,036 dated Aug. 30, 2021.
U.S. Appl. No. 17/494,578, filed Oct. 5, 2021.
U.S. Appl. No. 17/501,591, filed Oct. 14, 2021.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/485,578, filed Apr. 14, 2017.
U.S. Appl. No. 62/853,279, filed May 28, 2019.
U.S. Appl. No. 62/864,656, filed Jun. 21, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/067,542, filed Aug. 19, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/109,066, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/134,450, filed Jan. 6, 2021.
U.S. Appl. No. 63/134,631, filed Jan. 7, 2021.
U.S. Appl. No. 63/134,754, filed Jan. 7, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
Exhibit A to PureWick's Fourth Supplemental Response to Interrogatory No. 3, Mar. 2021, 21 pages.
PureWick's Supplemental Response to Interrogatory No. 6 Exhibit C: U.S. Pat. No. 6,287,508, Sep. 2020, 21 pages.
Exhibit B to PureWick's Supplemental Response to Interrogatory No. 6: U.S. Pat. No. 8,287,508, 25 pages.
Exhibit B to PureWick's Supplemental Response to Interrogatory No. 6: U.S. Pat. No. 10,390,989, 26 pages.
Exhibit B to PureWick's Supplemental Response to Interrogatory No. 6: U.S. Pat. No. 10,226,376, 38 pages.
Sage's Second Notice of Deposition of PureWick Corporation, C.A. No. 19-1508-MN, Feb. 2021, 10 pages.
Sage's First Notice of Deposition of PureWick Corporation, C.A. No. 19-1508-MN, Feb. 2021, 14 pages.
Supplemental Statement Regarding References and Combinations, C.A. No. 19-1508-MN, 3 pages.
Sixth Supplemental Responses to Sage Products' First Set of Interrogatories (No. 1-11) to PureWick Corporation, C.A. No. 19-1508-MN, Apr. 2021, 39 pages.
Seventh Supplemental Responses to Sage Products' First Set of Interrogatories (No. 1-11) to PureWick Corporation, C.A. No. 19-1508-MN, Apr. 2021, 41 pages.
"External Urine Management for Female Anatomy", https://www.stryker.com/us/en/sage/products/sage-primafit.html, Jul. 2020, 4 pages.
Jennewein, "Connect Graduates 7 Startups in Tech, Life Sciences", https://timesofsandiego.com/business/2015/08/16/connect-graduates-7-startups-in-tech-life-sciences/, Aug. 2015, 2 pages.
Corrected Notice of Allowability for U.S. Appl. No. 17/330,657 dated Dec. 9, 2021.
Final Office Action for U.S. Appl. No. 16/905,400 dated Dec. 9, 2021.
International Search Report and Written Opinion from International Application No. PCT/US2021/043893 dated Nov. 22, 2021.

(56) References Cited

OTHER PUBLICATIONS

International Search Report and Written Opinion from International Application No. PCT/US2021/044699 dated Nov. 22, 2021.
International Search Report and Written Opinion from International Application No. PCT/US2021/047536 dated Dec. 23, 2021.
International Search Report and Written Opinion from International Application No. PCT/US2021/048211 dated Dec. 22, 2021.
Non-Final Office Action for U.S. Appl. No. 16/245,726 dated Jan. 21, 2022.
Non-Final Office Action for U.S. Appl. No. 16/449,039 dated Dec. 8, 2021.
Non-Final Office Action for U.S. Appl. No. 29/741,751 dated Jan. 18, 2022.
Notice of Allowance for U.S. Appl. No. 16/899,956 dated Dec. 29, 2021.
Notice of Allowance for U.S. Appl. No. 17/330,657 dated Nov. 26, 2021.
Restriction Requirement for U.S. Appl. No. 16/433,773 dated Dec. 7, 2021.
U.S. Appl. No. 17/394,055, filed Aug. 4, 2021.
U.S. Appl. No. 17/453,260, filed Nov. 2, 2021.
U.S. Appl. No. 17/453,560, filed Nov. 4, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 62/935,337, filed Nov. 14, 2019.
U.S. Application No. 62/967,977, filed Jan. 30, 2020.
U.S. Appl. No. 63/109,084, filed Nov. 3, 2020.
U.S. Appl. No. 63/133,892, filed Jan. 5, 2021.
U.S. Appl. No. 63/138,878, filed Jan. 19, 2021.
U.S. Appl. No. 63/299,208, filed Jan. 13, 2022.
"Rising Warrior Insulated Gallon Jug Cover", https://www.amazon.com/Rising-Warrior-Insulated-Sleeve, 2021, 2 pages.
"Urine Bag Cover—Catheter Bag Cover 2000 ml Volume—Medline Style—Multiple Sclerosis—Spine Injury—Suprapublic Catheter—Bladder Incontinence", https://www.etsy.com/listing/1142934658/urine-bag-cover-caatheter-bag-cover-2000, 2022, 1 page.
"Vinyl Dust Cover, Janome #741811000, Janome, Sewing Parts Online", https://www.sewingpartsonline.com/vinyl-dust-cover-janome-74181000,2020, 2 pages.
Ali, "Sustainability Assessment: Seventh Generation Diapers versus gDiapers", The University of Vermont, Dec. 5, 2011, pp. 1-31.
Autumn, et al., "Frictional adhesion: a new angle on gecko attachment", The Journal of Experimental Biology, 2006, pp. 3569-3579.
Cañas, et al., "Effect of nano- and micro-roughness on adhesion of bioinspired micropatterned surfaces", Acta Biomaterialia 8, 2012, pp. 282-288.
Chaudhary, et al., "Bioinspired dry adhesive: Poly(dimethylsiloxane) grafted with poly(2-ethylhexyl acrylate) brushes", European Polymer Journal, 2015, pp. 432-440.
Dai, et al., "Non-sticky and Non-slippery Biomimetic Patterned Surfaces", Journal of Bionic Engineering, Mar. 2020, pp. 326-334.
Espinoza-Ramirez, "Nanobiodiversity and Biomimetic Adhesives Development: From Nature to Production and Application", Journal of Biomaterials and Nanobiotechnology, pp. 78-101, 2019.
Hwang, et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong, et al., "A nontransferring dry adhesive with hierarchical polymer nanohairs", PNAS, Apr. 7, 2009, pp. 5639-5644.
Jeong, et al., "Nanohairs and nanotubes: Efficient structural elements for gecko-inspired artificial dry adhesives", Science Direct, 2009, pp. 335-346.
Karp, et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Parness, et al., "A microfabricated wedge-shaped adhesive array displaying gecko-like dynamic adhesion, directionality", J.R. Soc. Interface, 2009, pp. 1223-1232.
Tsipenyuk, et al., "Use of biomimetic hexagonal surface texture in friction against lubricated skin", Journal of The Royal Society—Interface, 2014, pp. 1-6.

* cited by examiner

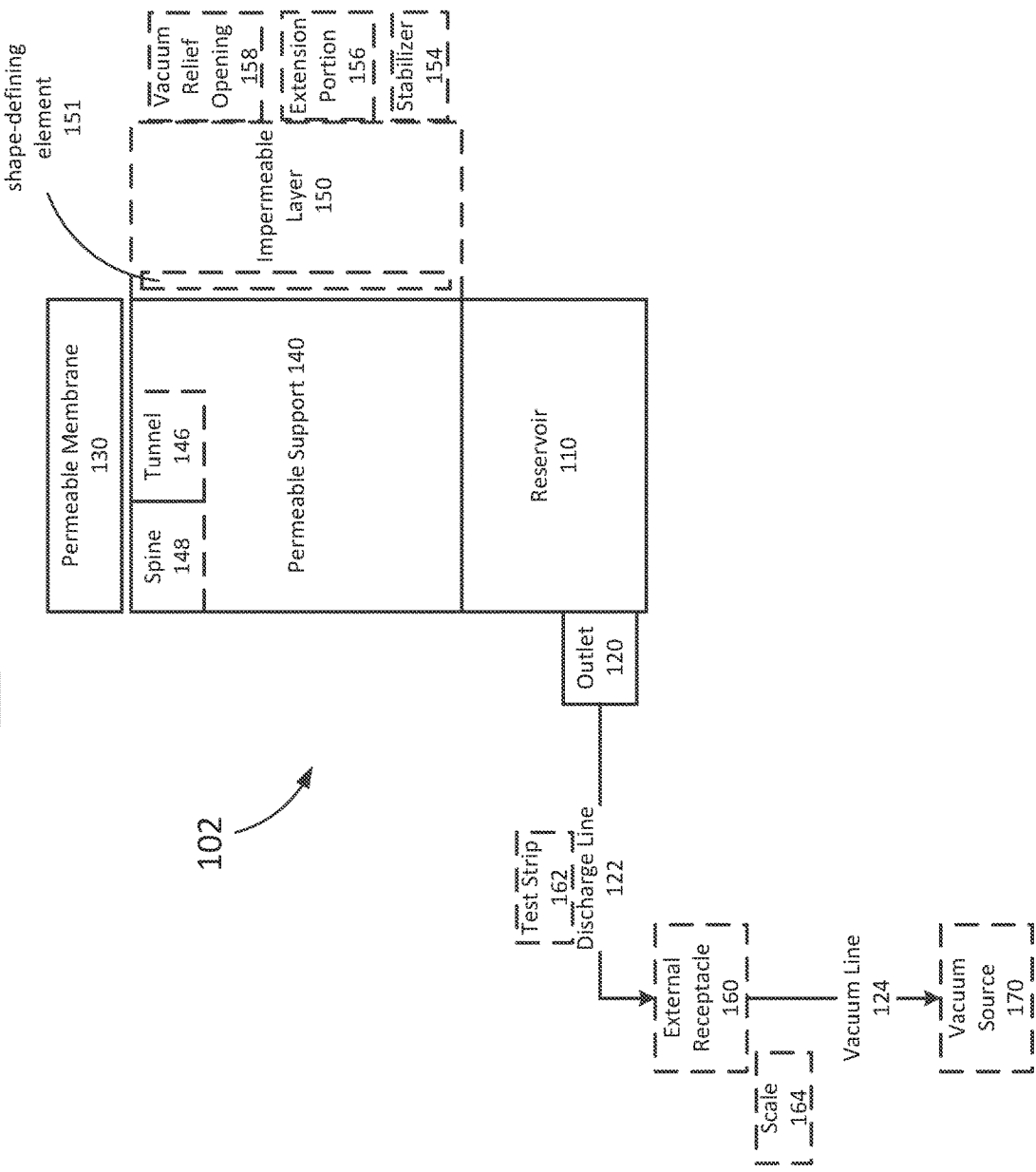

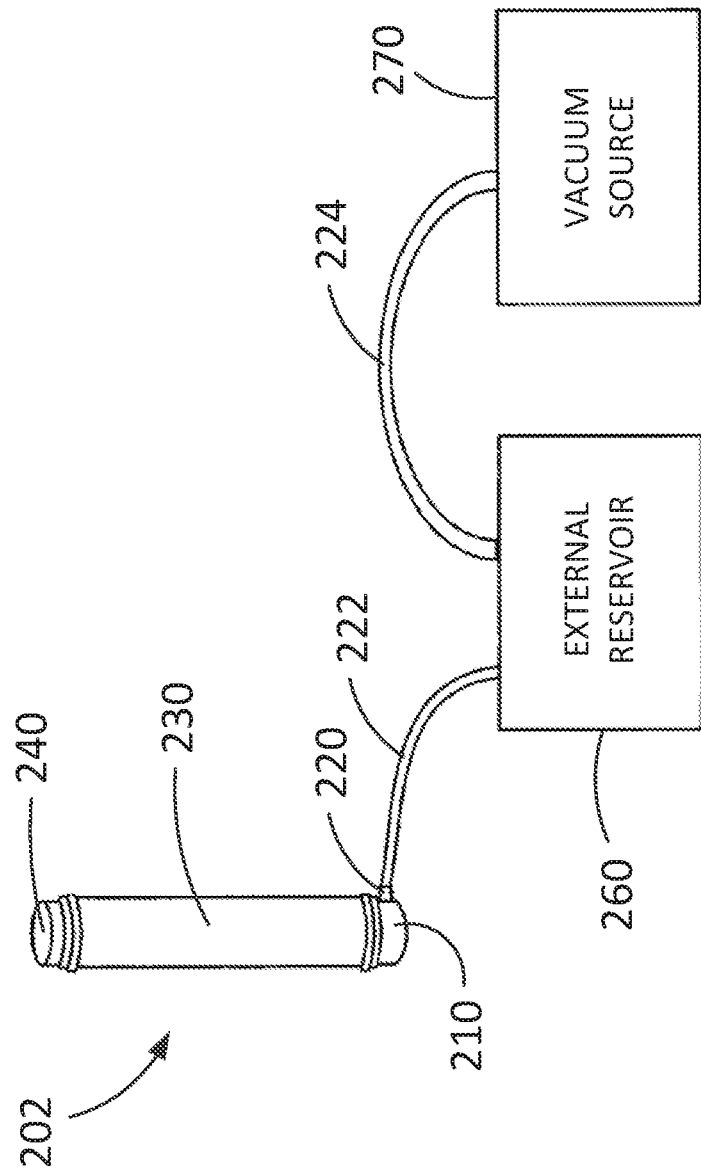

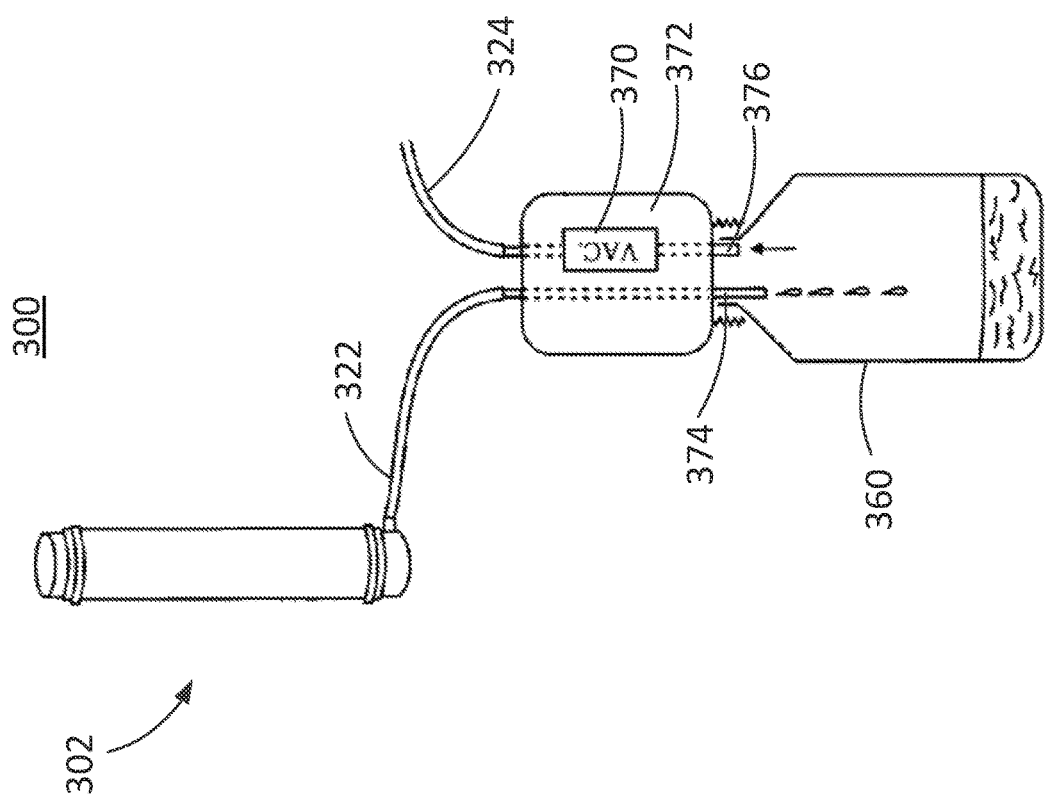

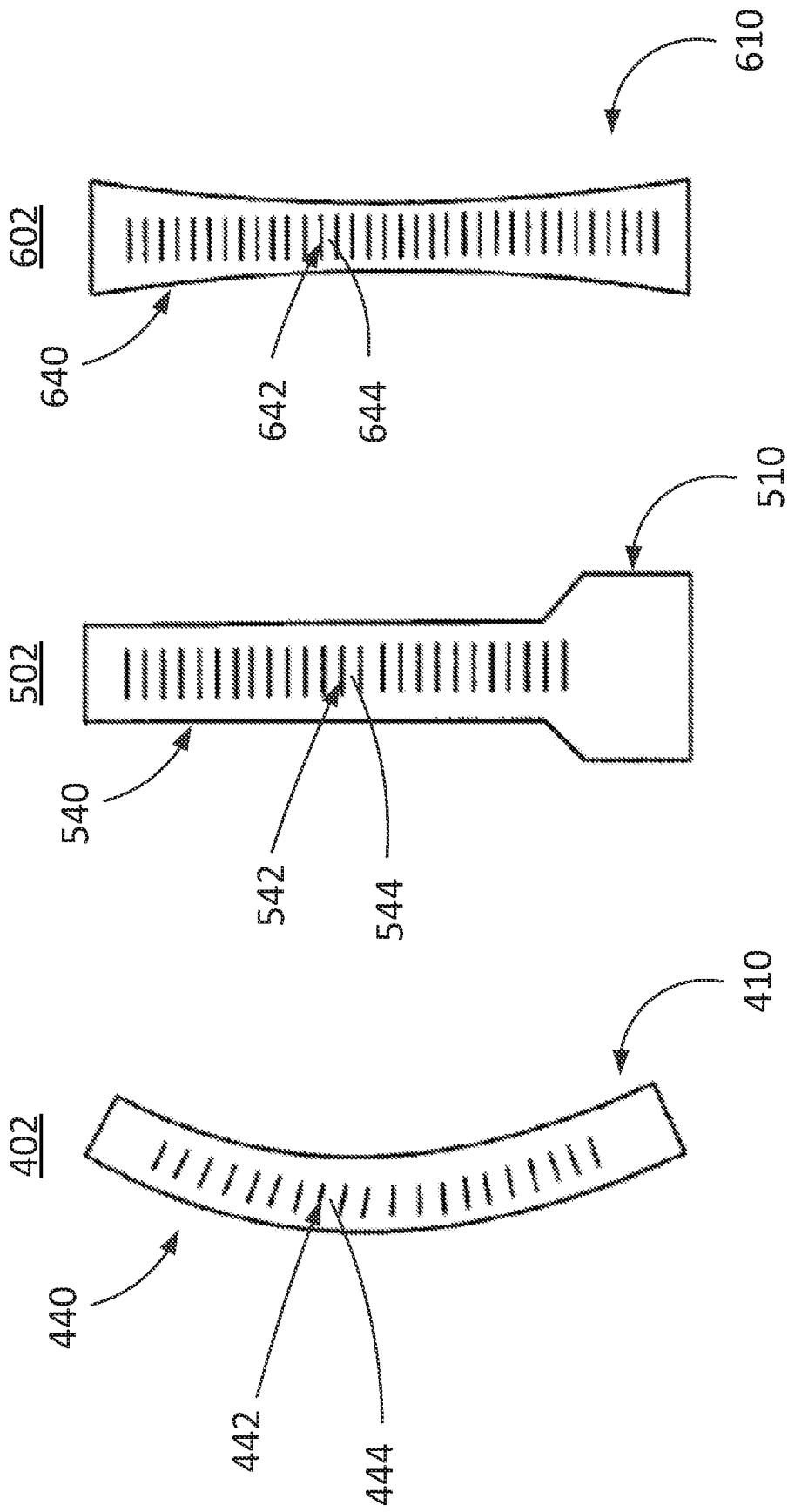

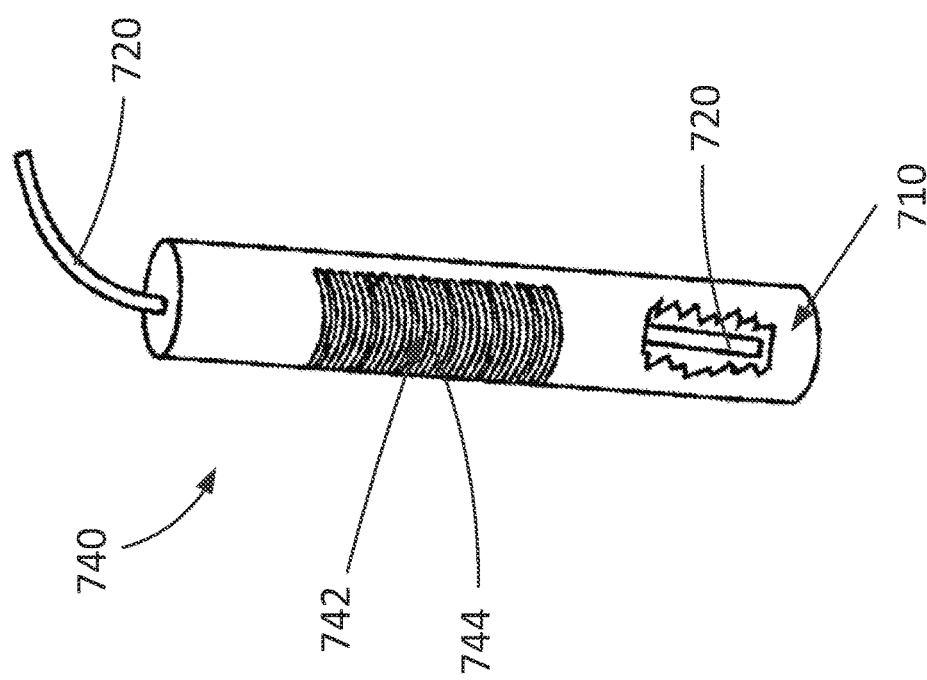

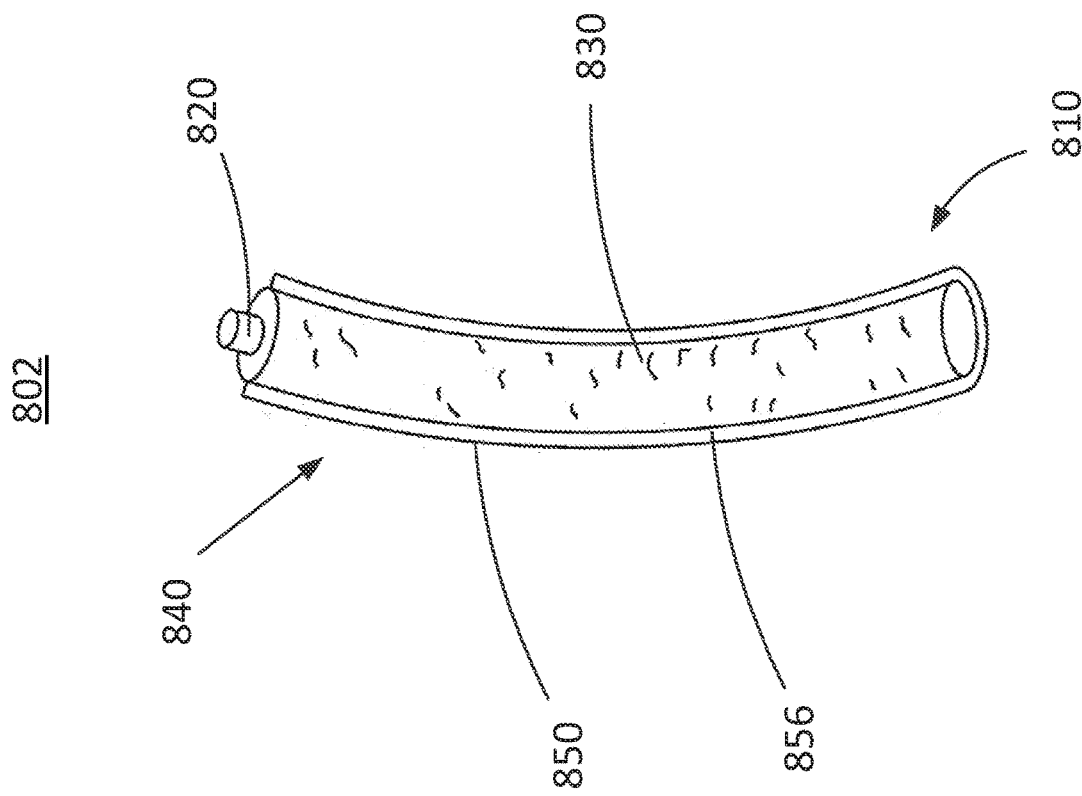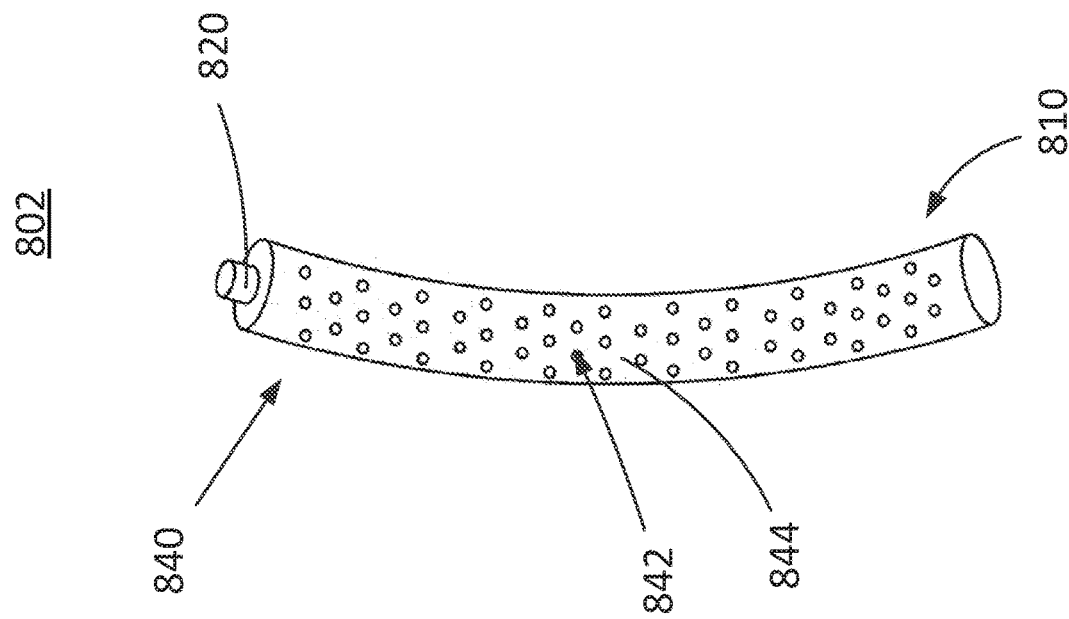

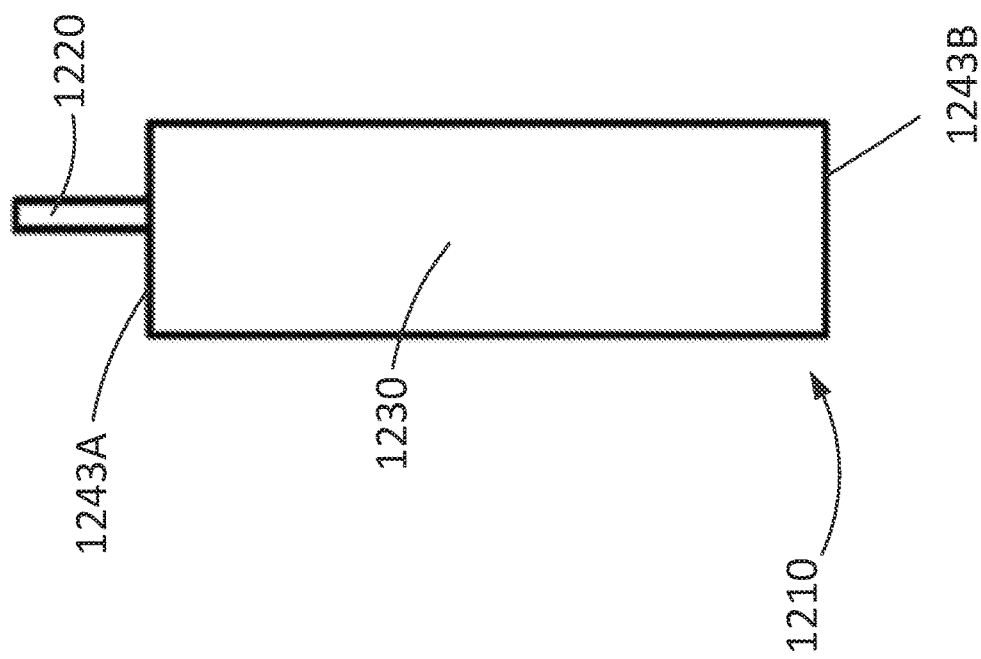
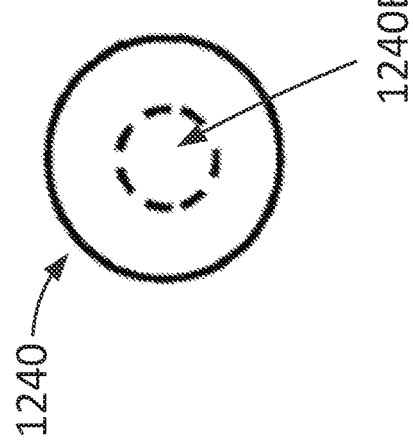
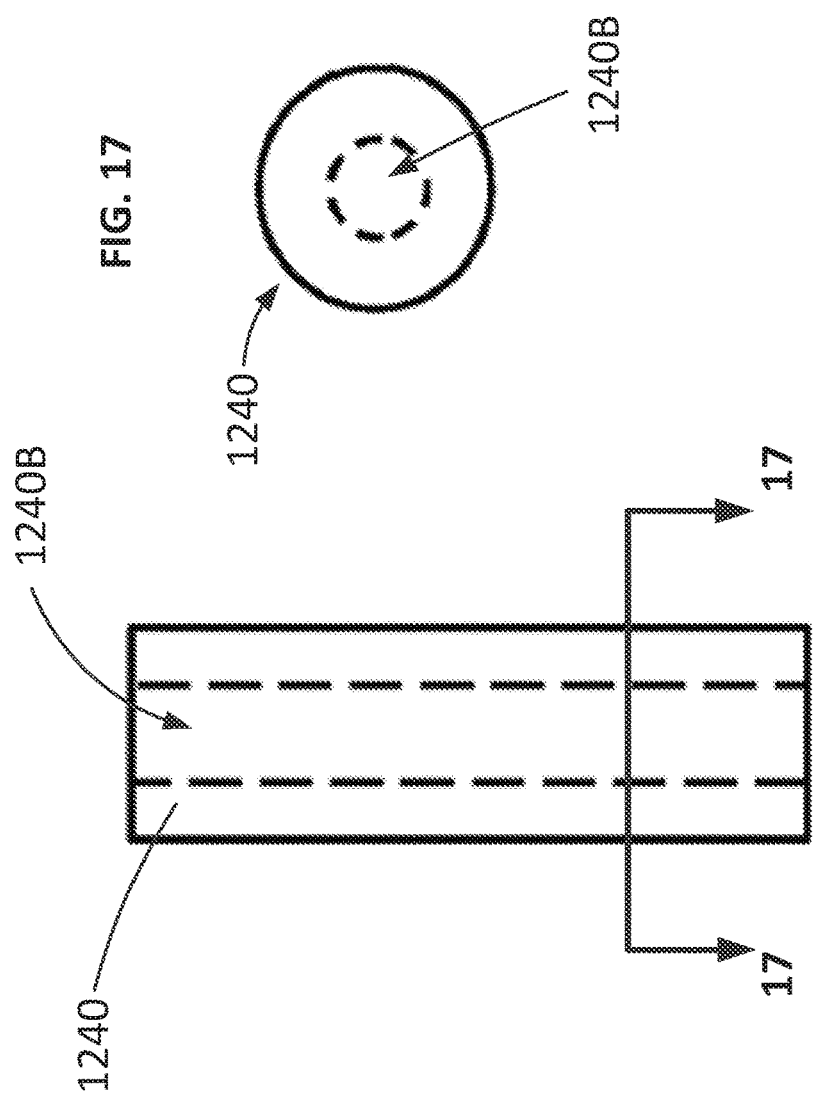

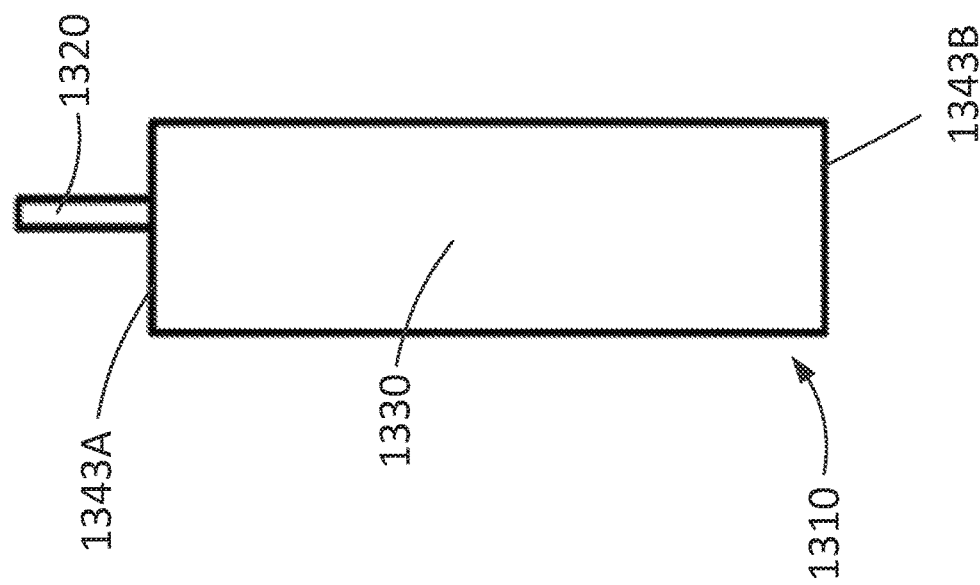
FIG. 21
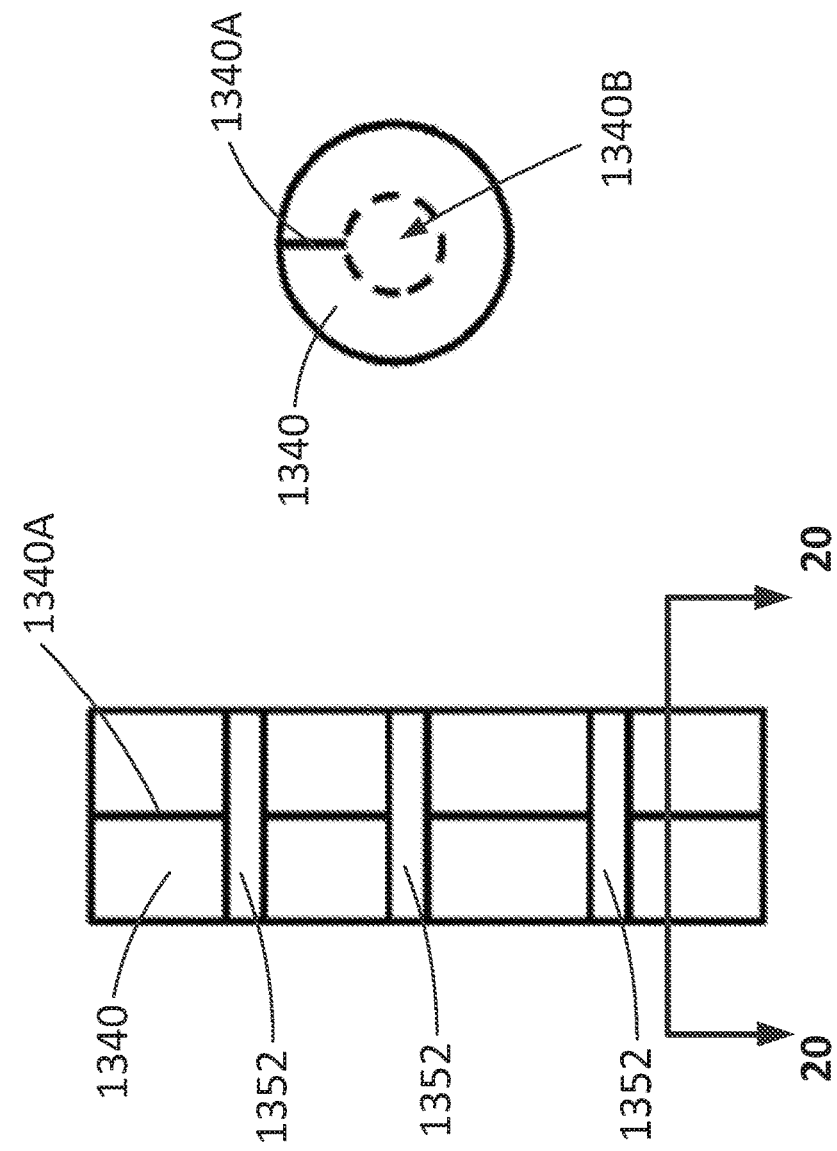
FIG. 20
FIG. 19

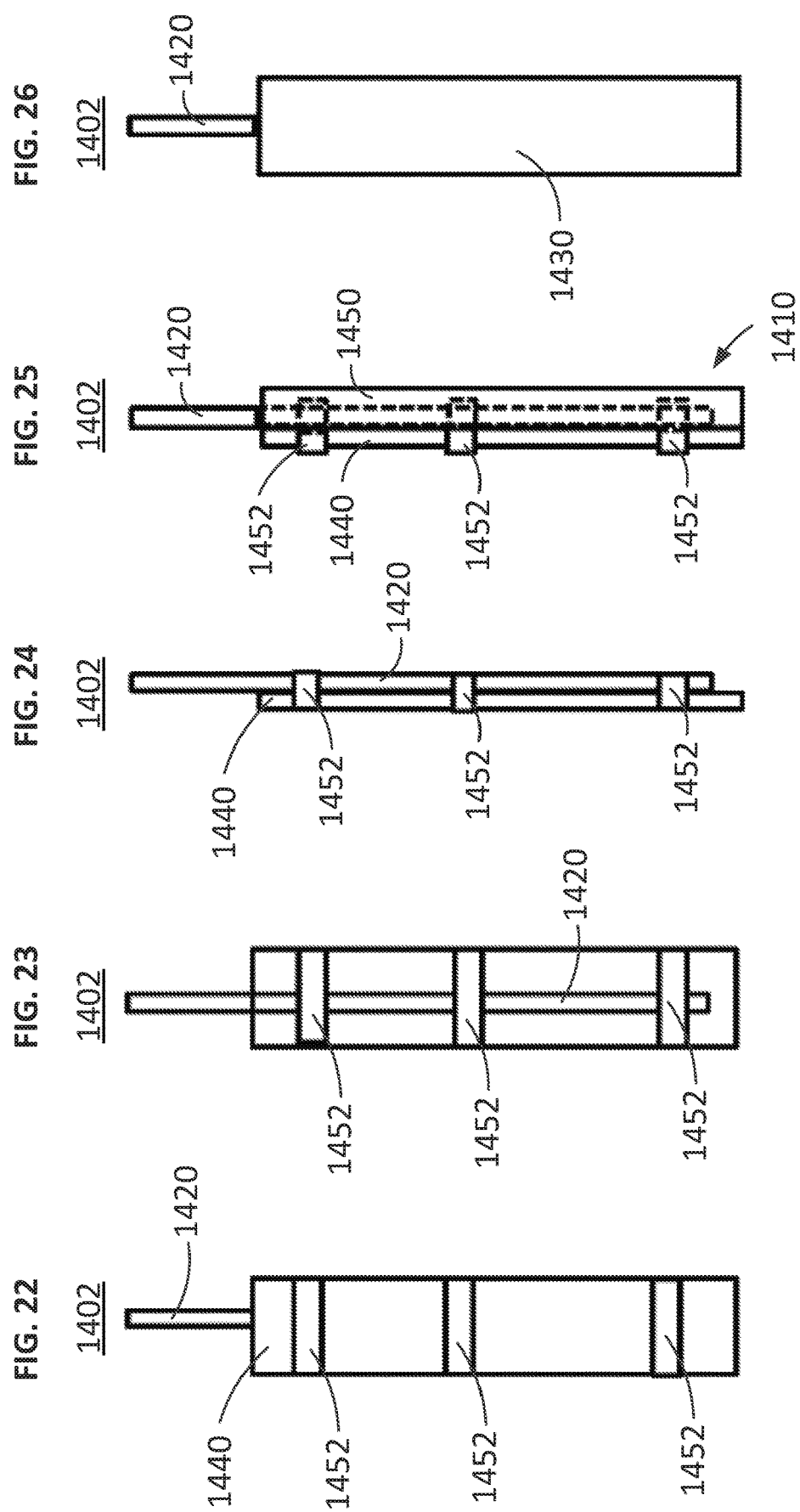

1902
Fluidically couple fluid discharge end of tube of a urine collecting apparatus to fluid receptacle 1904
Fluidically couple a fluid discharge end of tube to a source of vacuum to assist in withdrawing urine via the tube from a reservoir of the urine collecting apparatus 1906
Dispose urine collecting apparatus with fluid permeable membrane exposed through opening in fluid impermeable casing in operative relationship with the urethral opening of a female user 1908
Allow urine discharged from the urethral opening to be received through the opening of the fluid impermeable layer into reservoir of urine collecting apparatus 1910
Allow urine to be withdrawn from reservoir via tube, out of a fluid discharge end of the tube 1912
Allow urine to be collected in fluid receptacle 1916
Remove urine collecting apparatus from operative relationship with urethral opening of user 1918
Dispose a second urine collecting apparatus in operative relationship with urethral opening of user

APPARATUS AND METHODS FOR RECEIVING DISCHARGED URINE

CROSS-REFERENCE TO RELATED APPLICATIONS

This application is a continuation of U.S. patent application Ser. No. 16/245,726 filed on Jan. 11, 2019; U.S. patent application Ser. No. 16/245,726 is a continuation of U.S. patent application Ser. No. 15/611,587 (now issued as U.S. Pat. No. 10,226,376) filed on Jun. 1, 2017; U.S. patent application Ser. No. 15/611,587 claims the benefit of U.S. Provisional Application Nos. 62/485,578 filed on Apr. 14, 2017 and 62/414,963 filed on Oct. 31, 2016 and is a continuation in part of U.S. patent application Ser. No. 15/260,103 (now issued as U.S. Pat. No. 10,390,989) filed on Sep. 8, 2016; U.S. patent application Ser. No. 15/260,103 is a continuation of International Application No. PCT/US2016/049274 filed on Aug. 29, 2016, a continuation in part of U.S. patent application Ser. No. 14/952,591 filed on Nov. 25, 2015, a continuation in part of U.S. patent application Ser. No. 14/947,759 filed on Nov. 20, 2015, and a continuation in part of U.S. patent application Ser. No. 14/625,469 filed on Feb. 28, 2015; International Application No. PCT/US2016/049274 is a continuation in part of U.S. patent application Ser. No. 15/171,968 filed on Jun. 2, 2016; U.S. patent application Ser. No. 14/952,591 claims the benefit of U.S. Provisional Patent Application 62/084,078 filed on Nov. 25, 2014; U.S. patent application Ser. No. 14/947,759 claims the benefit of U.S. Provisional Patent Application No. 62/082,279 filed on Nov. 20, 2014; and U.S. patent application Ser. No. 14/625,469 claims benefit of U.S. Provisional Patent Application No. 61/955,537 filed on Mar. 19, 2014; the disclosure of each of the foregoing applications are incorporated herein, in its entirety, by this reference.

TECHNICAL FIELD

The present disclosure relates generally to systems, apparatus, and methods for collecting and transporting urine away from the body of a person or animal.

BACKGROUND

The embodiments described herein relate generally to collecting and transporting urine away from the body of a person or animal. In various circumstances, a person or animal may have limited or impaired mobility such that typical urination processes are challenging or impossible. For example, a person may experience or have a disability that impairs mobility. A person may have restricted travel conditions such as those experienced by pilots, drivers, and workers in hazardous areas. Additionally, sometimes urine collection is needed for monitoring purposes or clinical testing.

Urinary catheters, such as a Foley catheter, can be used to address some of these circumstances, such as incontinence. Unfortunately, however, urinary catheters can be uncomfortable, painful, and can lead to complications, such as infections. Additionally, bed pans, which are receptacles used for the toileting of bedridden patients, such as those in a health care facility, are sometimes used. Bed pans, however, can be prone to discomfort, spills, and other hygiene issues.

Thus, there is a need for a device capable of collecting urine from a person or animal comfortably and with minimal contamination of the user and/or the surrounding area.

SUMMARY

A system is disclosed that is suitable for collecting and transporting urine away from the body of a person or animal. The disclosed system includes an assembly that may include a fluid impermeable casing having a fluid reservoir at a first end, a fluid outlet at a second end, and a longitudinally extending fluid impermeable layer coupled to the fluid reservoir and the fluid outlet and defining a longitudinally elongated opening between the fluid reservoir and the fluid outlet. The assembly can further include a fluid permeable support disposed within the casing with a portion extending across the elongated opening, and a fluid permeable membrane disposed on the support and covering at least the portion of the support that extends across the elongated opening, so that the membrane is supported on the support and disposed across the elongated opening. The assembly can further include a tube having a first end disposed in the reservoir and extending behind at least the portion of the support and the portion of the membrane disposed across the elongated opening and extending through the fluid outlet to a second, fluid discharge end. The assembly can be configured to be disposed with the opening adjacent to a urethral opening of a user, to receive urine discharged from the urethral opening through the opening of the fluid impermeable layer, the membrane, the support, and into the reservoir, and to have the received urine withdrawn from the reservoir via the tube and out of the fluid discharge end of the tube.

BRIEF DESCRIPTION OF THE DRAWINGS

FIG. 1 is a schematic block diagram of a system, according to an embodiment.

FIG. 4 is a schematic illustration of the assembly of FIG. 2 as part of a system.

FIG. 5 is a schematic illustration of a system, according to an embodiment.

FIG. 6A is front view of an assembly, according to an embodiment.

FIG. 6B is front view of an assembly, according to an embodiment.

FIG. 6C is front view of an assembly, according to an embodiment.

FIG. 7 is a perspective view of an assembly with a portion of the assembly shown in cut away, according to an embodiment.

FIG. 8 is a perspective view of an assembly, according to an embodiment.

FIG. 9 is a perspective view of the assembly of FIG. 8 including a permeable membrane, according to an embodiment.

FIG. 16 is a perspective view of a permeable support, according to an embodiment.

FIG. 17 is a cross-sectional view of the permeable support of FIG. 16 taken along line 17-17.

FIG. 18 is a side view of an assembly including the permeable support of FIG. 16, according to an embodiment.

FIG. 19 is a perspective view of a permeable support, according to an embodiment.

FIG. 20 is a cross-sectional view of the permeable support of FIG. 19 taken along line 20-20.

FIG. 21 is a side view of an assembly including the permeable support of FIG. 19, according to an embodiment.

FIGS. 22-24 are front, back, and side views of an assembly, respectively, according to an embodiment.

FIG. 25 is a side view of the assembly of FIG. 22 including an impermeable backing.

FIG. 26 is a front view of the assembly of FIG. 22 including a permeable membrane.

FIG. 39 is a flowchart illustrating a method of using an assembly to collect urine from a user, according to an embodiment.

DETAILED DESCRIPTION

Figure 3:
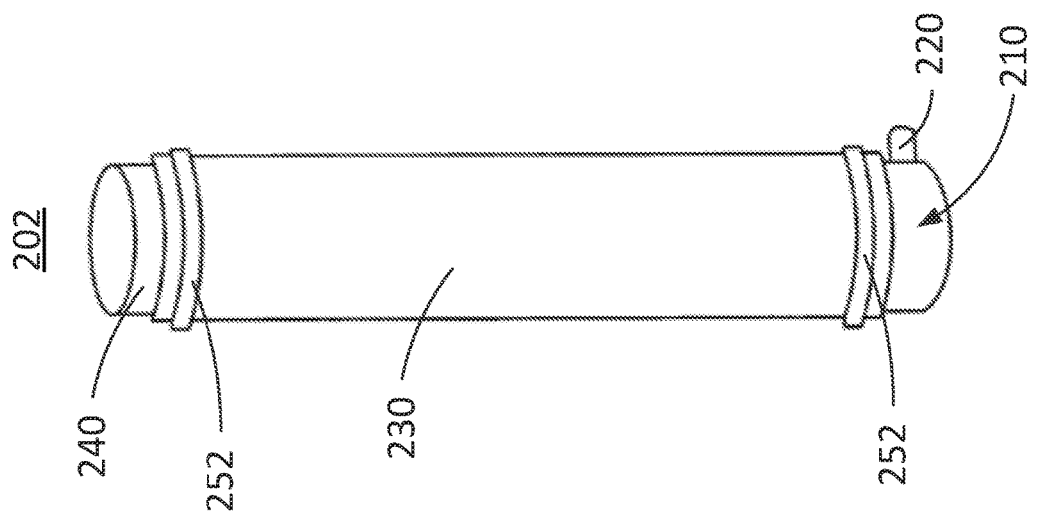
FIG. 3 is a perspective view of the assembly of FIG. 2 including a permeable membrane.

A system is disclosed that is suitable for collecting and transporting urine away from the body of a person or animal. The disclosed system includes an assembly that may include a fluid impermeable casing having a fluid reservoir at a first end, a fluid outlet at a second end, and a longitudinally extending fluid impermeable layer coupled to the fluid reservoir and the fluid outlet and defining a longitudinally elongated opening between the fluid reservoir and the fluid outlet. The assembly can further include a fluid permeable support disposed within the casing with a portion extending across the elongated opening, and a fluid permeable membrane disposed on the support and covering at least the portion of the support that extends across the elongated opening, so that the membrane is supported on the support and disposed across the elongated opening. The assembly can further include a tube having a first end disposed in the reservoir and extending behind at least the portion of the support and the portion of the membrane disposed across the elongated opening and extending through the fluid outlet to a second, fluid discharge end. The assembly can be configured to be disposed with the opening adjacent to a urethral opening of a user, to receive urine discharged from the urethral opening through the opening of the fluid impermeable layer, the membrane, the support, and into the reservoir, and to have the received urine withdrawn from the reservoir via the tube and out of the fluid discharge end of the tube.

In some embodiments, a method includes disposing in operative relationship with the urethral opening of a female user, a urine collecting apparatus. The urine collecting apparatus can include a fluid impermeable casing having a fluid reservoir at a first end, a fluid outlet at a second end, and a longitudinally extending fluid impermeable layer coupled to the fluid reservoir and the fluid outlet and defining a longitudinally elongated opening between the fluid reservoir and the fluid outlet. The urine collecting apparatus can also include a fluid permeable support disposed within the casing with a portion extending across the elongated opening, a fluid permeable membrane disposed on the support and covering at least the portion of the support that extends across the elongated opening, so that the membrane is supported on the support and disposed across the elongated opening, and a tube having a first end disposed in the reservoir and extending behind at least the portion of the support and the portion of the membrane disposed across the elongated opening and extending through the fluid outlet to a second, fluid discharge end. The operative relationship can include the opening being adjacent to the urethral opening. The method can further include allowing urine discharged from the urethral opening to be received through the opening of the fluid impermeable layer, the membrane, the support, and into the reservoir; and allowing the received urine to be withdrawn from the reservoir via the tube and out of the fluid discharge end of the tube.

In some embodiments, an apparatus includes a fluid permeable support disposed between a fluid permeable membrane and a fluid reservoir, and a fluid outlet. The apparatus can be configured to be disposed with a portion of the fluid permeable membrane adjacent to a urethral opening of a user, to receive urine discharged from the urethral opening through the fluid permeable membrane, the fluid permeable support, and into the reservoir, and to have the received urine withdrawn from the reservoir via the outlet.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

The embodiments described herein can be formed or constructed of one or more biocompatible materials. Examples of suitable biocompatible materials include metals, ceramics, or polymers. Examples of suitable metals include pharmaceutical grade stainless steel, gold, titanium, nickel, iron, platinum, tin, chromium, copper, and/or alloys thereof. Examples of polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, polyethylene terephthalate (PET), polytetrafluoroethylene (PTFE), and/or blends and copolymers thereof.

FIG. 1 is a schematic block diagram of a system 100. The system 100 includes an assembly 102. The assembly 102 includes a reservoir 110, a permeable support 140, and a permeable membrane 130. The assembly 102 also includes an outlet 120 in fluidic communication with the reservoir 110. The assembly 102 can be arranged such that a fluid can flow through the permeable membrane 130, through the permeable support 140, into the reservoir 110, and out of the outlet 120. In some implementations, the assembly 102 can also include an impermeable layer 150 for directing fluid toward the reservoir 110 and reducing and/or preventing fluid from exiting the assembly 102 except via the outlet 120. In some implementations, the system 100 can include a discharge line 122. The discharge line 122 can be fluidically coupled to an external receptacle 160. The external receptacle 160 can be in fluidic communication with a vacuum source 170 via a vacuum line 124. The discharge line 122 and the vacuum line 124 can both include flexible tubing, such as, for example, flexible plastic tubing.

The permeable membrane 130 can be formed of a material that has permeable properties with respect to liquids such as urine. The permeable properties can be wicking, capillary action, diffusion, or other similar properties or processes, and are referred to herein as "permeable" and/or "wicking." The permeable membrane 130 can have a high absorptive rate and a high permeation rate such that urine can be rapidly absorbed by the permeable membrane 130 and/or transported through the permeable membrane 130. In some implementations, the permeable membrane 130 can be a ribbed knit fabric. In some implementations, the permeable membrane 130 can include and/or have the moisture-wicking characteristic of gauze, felt, terrycloth, thick tissue paper, and/or a paper towel. In some implementations, the permeable membrane 130 can be soft and/or minimally abrasive such that the permeable membrane 130 does not irritate the skin of the user. The permeable membrane 130 can be configured to wick fluid away from the urethral opening and/or the skin of the user such that the dampness of the skin of the user is lessened and infections are prevented. Additionally, the wicking properties of the permeable membrane 130 can help prevent urine from leaking or flowing beyond the assembly onto, for example, a bed. In some implementations, the permeable membrane 130 can be formed of fine denier polyester fibers coated with a thermoplastic water-based binder system. The tensile with the Webb direction can be, for example, about 45 lbs/inch$^2$ measured using an Instron test method. The weight per permeable membrane can be, for example, about 12 grams measured using the Mettle Gram Scale. The thickness per ten permeable membrane can be, for example, about 2.5", measured using the Gustin-Bacon/Measure-Matic.

The permeable support 140 can be positioned relative to the permeable membrane 130 such that the permeable support 140 maintains the permeable membrane 130 in a particular shape and allows for fluid, such as, for example, urine, to flow through the permeable membrane 130, through the permeable support 140, and into the reservoir 110. In some implementations, the permeable support 140 can be configured to maintain the permeable membrane 130 against or near a urethral opening of a user. For example, the permeable support 140 can include a portion having a curved shape in contact with the permeable membrane 130 such that the permeable membrane 130 is also curved, thus creating a comfortable and secure interface for engagement with a user's urethral opening and/or the area of the body near the urethral opening. In some implementations, the permeable support 140 can be made of a rigid plastic. In some implementations, the permeable support 140 can have any suitable shape and be formed of any suitable material. For example, the permeable support 140 can be flexible. Additionally, the permeable support 140 can be formed of aluminum, a composite of plastic and aluminum, some other metal and/or a composite of plastic and another metal. In some implementations, the permeable support 140 can be formed of a natural material, such as, for example, plant fibers (e.g., Greener Clean manufactured by 3M®). The natural material can include openings that allow fluid to flow through the natural material. In some embodiments, the permeable support 140 can be cylindrical and can define a lumen. In some embodiments, the permeable support 140 can be formed of perforated coated paper, such as tubular waxed paper.

The permeable support 140 can define one or more openings (e.g., an array of openings) to allow for fluid flow from the permeable membrane 130 to the reservoir 110. In some implementations, the permeable support 140 can be formed as a tube, a cylinder, or a curved cylinder with one or more openings. In some implementations, the permeable support 140 can include membrane supports (e.g., struts) extending across an opening such that the opening is divided into an array of distinct slot-shaped openings. The membrane supports can be used to support the permeable membrane 130. For example, the membrane supports can maintain the shape of the permeable membrane 130 against or near a user's urethral opening such that urine flowing from the urethral opening contacts and travels through the permeable membrane 130. In some implementations, the permeable support 140 can define several openings having a variety of shapes, such as a plurality of round openings. In some implementations, the permeable support 140 can be formed as a cylinder of spun plastic (e.g., non-woven permeable nylon and polyester webbing) such that the permeable support 140 can have many openings. For example, a rectangular portion of spun plastic can be folded or rolled into a cylinder shape for use in the assembly 102. In some implementations, the permeable support 140 can be formed of a porous material. For example, the permeable support 140 can be a porous glass tubular container defining frits. In other implementations, the permeable support 140 can define an opening in a sidewall of the permeable support 140 and the sidewall can be covered by a mesh screen defining many smaller openings.

The reservoir 110 can be any suitable shape and/or size capable of collecting fluid transported through the permeable support 140. In some implementations, the reservoir 110 can be sized such that the reservoir is capable of collecting and temporarily holding a large or small amount of urine until the urine can be removed from the reservoir via the outlet 120. For example, the reservoir 110 can be sized such that the reservoir 110 is configured to hold a small amount of urine as may be released due to incontinence. In some implementations, the reservoir 110 can be sized such that the reservoir 110 is configured to hold a large amount of urine as may be released during voiding of a full bladder. In some implementations, the reservoir 110 can be sized such that the reservoir is configured to collect and hold a small or large amount of urine while the urine is simultaneously removed via, for example, gravity and/or a pump, such as the vacuum source 170. Said another way, the reservoir 110 can function as a sump and be sized such that the reservoir 110 can form a portion of a passageway for urine from the permeable membrane 130, through the permeable support 140, through the reservoir 110, and out of the outlet 120. In a condition where the flow rate of urine into the assembly 102 via the permeable membrane 130 is greater than the flow rate of urine through the discharge line 122, a temporary backup of urine may occur in the reservoir 110. Thus, the reservoir 110 can be sized to contain a volume of fluid that may temporarily accumulate due to the difference in flow rates into and out of the assembly 102.

Although the outlet 120 is shown as extending from the side of the reservoir 110, in some implementations, the outlet 120 can extend from the bottom of the reservoir 110. Positioning the outlet 120 lower in the reservoir 110 such that less or no urine can pool at the bottom of the reservoir 110 can allow for urine to be removed from the reservoir 110 more quickly and/or completely. In other implementations, the outlet 120 can be positioned within the reservoir such that at least a portion of tubing associated with the outlet 120 extends from the top of the reservoir 110. For example, a portion of tubing associated with the outlet 120 can extend from the top of the reservoir 110 through at least a portion of the permeable support 140 (e.g., a central channel) and, optionally, through at least a portion of the permeable membrane 130. In such an implementation, the outlet 120 can be positioned a distance from the reservoir 110 such that fluid can flow from the reservoir, through the tubing associated with the outlet 120, and from the outlet 120. In such implementations, positioning the reservoir end of the tubing associated with the outlet 120 towards the bottom of the reservoir 110 such that less or no urine can pool at the bottom of the reservoir 110 can allow for urine to be removed from the reservoir 110 more quickly and/or completely. In some implementations, the tubing associated with the outlet 120 can be precurved at least in the portion extending through the permeable support 140.

In some implementations, the reservoir 110 and the permeable support 140 can be formed as separate components and coupled together during assembly. In some implementations, the permeable support 140 and the reservoir 110 can be formed as a cylindrical integral, unitary structure that is sealed at one end by a closed end of the reservoir 110 and at the other end by a closed end of the permeable support 140.

The external receptacle 160, via the discharge line 122, can collect fluid exiting the reservoir 110 through the outlet 120. The external receptacle 160 can be a sealed container. In some implementations, the external receptacle 160 can be disposable. In some implementations, the external receptacle 160 can be configured to be sterilized and reused.

In some implementations, gravity can cause fluid within the reservoir 110 to follow a flow path (i.e., the fluid flow path including the outlet 120 and the discharge line 122) from the reservoir 110 to the external receptacle 160. In some implementations, the vacuum source 170 can assist and/or provide the pressure differential needed to draw fluid voided from the urethral opening of a user into the permeable support 140, into the reservoir 110, and from the reservoir 110 into the external receptacle 160. The vacuum source 170 can be fluidically coupled to the external receptacle 160 via a vacuum line 124 such that gaseous fluid is drawn from the external receptacle 160 via the vacuum line 124. As a result of the decrease in pressure within the external receptacle 160 caused by the drawing of gaseous fluid out of the external receptacle 160, liquid and/or gaseous fluid can be drawn from the reservoir 110, through the outlet 120, through the discharge line 122, and into the external receptacle 160. In some implementations, the vacuum source 170 can apply sufficient suction to capture all or substantially all of the urine voided by a user in a variety of positions (e.g., when a female user is lying on her side).

The vacuum source 170 can have a sufficiently high vacuum strength and air volume transport rate such that rapid air and liquid aspiration is maintained over a portion of or the entire permeable membrane 130. In some implementations, the one or more openings of the permeable support 140 are distributed over an area that is slightly larger than the area of the permeable membrane 130 that is configured to be wetted by urine flow in operation. Thus, the partial vacuum created by the vacuum source 170 in combination with the one or more openings of the permeable support 140 and the permeable membrane 130 can draw the urine contacting the permeable membrane 130 into the assembly 102. In some implementations, however, the one or more openings of the permeable support 140 should not be distributed over too large of an area of the permeable support 140 because the partial vacuum strength may be reduced, thereby reducing the urine collection rate and the efficiency of the system 100.

In some implementations, the vacuum source 170 can be a pump that is readily available, inexpensive, relatively quiet, and/or configured to run continuously. For example, the vacuum source 170 can be an aquarium aerator pump. The vacuum line 124 can be attached to the intake port of the aquarium aerator pump (rather than the exhaust port of the aerator) such that gaseous fluid is drawn into the aquarium aerator pump from the external receptacle 160 via the vacuum line 124. In some implementations, the necessary static vacuum of the system 100 is about 3-10 feet of water (10%-30% of one atmosphere; 80-250 mm Hg) with a free-flow rate of about 10-100 cubic centimeters per second. In some implementations, the necessary static vacuum of the system 100 is higher or lower depending on the size of the user and the expected rate of urine flow from the user and/or through the system 100. In some implementations, the discharge line 122 can be about 0.25" in diameter and the vacuum source 170 can be configured to cause about 500 cubic centimeters of urine to flow through the discharge line 122 to the external receptacle 160 over the duration of a typical urination event for a user, which may typically range from 10 to 20 seconds but may be shorter or longer, e.g., 5 to 90 seconds. In some implementations, the vacuum source 170 can include a wall-mounted vacuum system, such as is found in hospitals. In some implementations, a wall-mounted vacuum system can be configured to apply a vacuum of, for example, about 20 mm Hg to about 40 mm Hg. In some implementations, the vacuum source 170 can be powered by electrical AC or DC power. For example, in mobile applications when the user is away from an AC power source, such as when the user is using the system 100 during transportation via a wheel chair or motor vehicle, the vacuum source 170 can be powered by DC power.

The impermeable layer 150 can be impermeable to fluid, such as, for example, urine. In some implementations, the impermeable layer 150 can have a fluid transportation function and can assist in directing fluid towards the reservoir 110 and/or through the outlet 120 of the reservoir 110. In some implementations, the impermeable layer 150 can be formed as an integral, unitary structure. In other implementations, the impermeable layer 150 can be a multi-piece structure. The impermeable layer 150 can be a pre-molded (e.g., injection or blow molded) component. Alternatively, the impermeable layer 150 can be formed of a material, such as elongate strips of an adhesive tape, wrapped around at least a portion of the reservoir, a portion of the permeable support 140, and/or a portion of the permeable membrane 130. In some implementations, the impermeable layer 150 can be formed of cardboard, pressed paper, and/or coated paper.

In some implementations, as shown in FIG. 1, the assembly 102 can optionally include a shape-defining or shape-retaining element 151. The shape-retaining element 151 can be attached to the impermeable layer 150 and can cause at least a portion of the assembly 102 to assume or maintain a curved shape. In some implementations, the shape-retaining element 151 can be disposed between the impermeable layer 150 and the permeable support 140 and/or the permeable membrane 130. In some implementations, the shape-retaining element 151 can be attached to an outer surface of the impermeable layer 150 or can be imbedded in the impermeable layer 150. In some embodiments the tubing associated with the outlet 120 can constitute the shape-retaining element 151, i.e. the tubing can be relatively rigid and having a curved shape that defines the desired curved shape for at least a portion of the assembly 102.

In some implementations, the permeable support 140 can optionally include a spine 148. The spine 148 can divide an inner volume of the permeable support 140 into two or more longitudinal chambers and can strengthen the permeable support 140 such that the permeable support 140 maintains an intended shape. The two chambers can be aligned with an inlet of the permeable support 140 (i.e., the one or more openings in the permeable support 140) such that fluid can flow through the inlet, through at least one of the two chambers, and into the reservoir 110. Although only one spine 148 is described, in some implementations, the permeable support 140 can include additional spines such that the permeable support 140 is divided into additional chambers.

In some implementations, the permeable support 140 can optionally include a tunnel 146. The tunnel 146 can be coupled to the outlet 120 of the assembly 102 in a configuration in which the outlet 120 is positioned on the top of the assembly 102. In some implementations, an external tube can be inserted through the tunnel 146 into contact with fluid in the reservoir 110 such that the fluid in the reservoir 110 can be removed from the assembly 102 via the external tube (e.g., using a vacuum source such as vacuum source 170). In some implementations, a length of tubing, such as the discharge line 122, can be fluidically coupled to an end of the tunnel 146 such that fluid can be drawn up the tunnel 146 from the reservoir 110 and out of the assembly 102.

In some implementations, the impermeable layer 150 can include an extension portion 156. The extension portion 156 can extend away from the permeable membrane 130 and/or the permeable support 140 such that the extension portion 156 can be gripped by a user or caregiver without contacting the permeable membrane 130. Thus, the extension portion 156 can be used to remove the permeable membrane 130 and the impermeable layer 150 from the permeable support 140. In some implementations, the extension portion 156 can be shaped as an elongated tab that extends along the length of the assembly 102 on one or more sides of the assembly 102. In some implementations, the extension portion 156 can be configured to prevent urine from traveling beyond the border between the permeable membrane 130 and the impermeable layer 150. For example, the extension portion 156 can be shaped and disposed relative to the permeable membrane 130 such that in a condition where the rate of urine flowing from the urethral opening exceeds the rate the permeable membrane 130 or a portion of the permeable membrane 130 can wick fluid and/or the rate that fluid can travel through the permeable membrane 130 and permeable support 140, the extension portion 156 can prevent urine from flowing onto an outer surface of the impermeable layer 150 beyond the extension portion 156 and can redirect urine along the permeable membrane 130 such that the urine is directed through the permeable membrane 130.

In some implementations, the impermeable layer 150 can include a stabilizer 154. The stabilizer 154 can be configured to stabilize the assembly 102 relative to a user's body. For example, in some situations of use, such as for incontinence, for disability that limits or impairs mobility, for restricted travel conditions (e.g., conditions experienced by pilots, drivers, and/or workers in hazardous areas), for monitoring purposes, or for clinical testing, it may aid the engagement between the permeable membrane 130 and the user's urethral opening and/or the area surrounding the urethral opening to include the stabilizer 154. The stabilizer 154 can be coupled to or integrally formed with the impermeable layer 150. In some implementations, a first end of the stabilizer 154 is coupled to the impermeable layer 150 and a second end of the stabilizer 154 is coupled to a user's body (e.g., via adhesive or tape) or an apparatus occupied by the user (e.g., a bed or wheelchair) to stabilize the position of the assembly 102 relative to a user's urethral opening and/or the area surrounding the urethral opening. The stabilizer 154 can be a thin, pliable strip of material. For example, in some implementations the stabilizer 154 can include tape, gauze, cotton, cloth, or plastic. The stabilizer 154 can be any suitable length and/or width. In some implementations, the stabilizer 154 can be as thin as a single thread.

In some implementations, the impermeable layer 150 can define one or more vacuum relief openings 158. Thus, in the event that a user's body envelopes the assembly 102, the one or more vacuum relief openings 158 can prevent suction from increasing against the skin of the user, which may be uncomfortable or painful. Said another way, the one or more vacuum relief openings 158 can be located between two ends of the impermeable layer 150 such that at least one additional airflow path exists in the assembly 102. The one or more vacuum relief openings 158 can be disposed at any suitable location on the impermeable layer 150. For example, in some implementations, the one or more vacuum relief openings 158 can be disposed near the outlet 120 of the apparatus 102. In some implementations, the one or more vacuum relief openings 158 can be disposed in a location that reduces the likelihood that the skin of the labia or the thigh of the user inadvertently covers the hole, such as a location near the outlet 120.

In some implementations, urine collected by any of the systems and/or assemblies described herein can be sampled for analysis using urine strips. Urine test strips can be used to test a variety of health measures. Urine test strips can be configured to change color in response to being wetted with urine to indicate a particular measurement (i.e., the colors can correspond to known measurement scales). In some implementations, a urine test strip 162 can be inserted into the discharge line 122 such that urine flowing from the outlet 120 to the external receptacle 160 contacts the urine test strip 162. The discharge line 122 can be transparent such that data on the urine test strip 162 can be read through a wall of the discharge line 122. In some implementations, the urine test strip 162 can be disposed within the external receptacle 160 such that urine flowing into the external receptacle 160 contacts the urine test strip 162. The external receptacle 160 can be at least partially transparent such that the urine test strip 162 can be read through a wall of the external receptacle 160.

Figure 14:
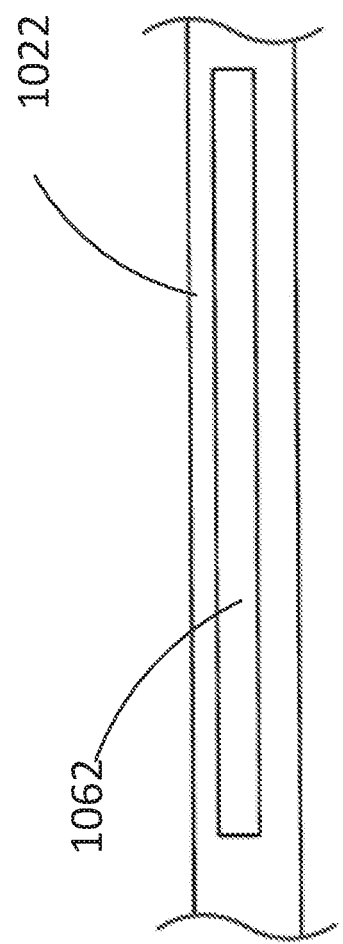
FIG. 14 is a schematic illustration of a urine test strip in a portion of tubing line, according to an embodiment.

As an example, FIG. 14 is a schematic illustration of a portion of tubing line 1022 and a urine test strip 1062 affixed to the inside of the portion of tubing line 1022. The portion of tubing line 1022 can be included in or form the entire discharge line (e.g., discharge line 122) from an outlet of an assembly (e.g., outlet 120) to an external receptacle (e.g., external receptacle 160). The urine test strip 1062 can be secured within the tubing line 1022 by friction or by using any suitable adhesive. In some implementations, the tubing line 1022 can be a short tube segment (e.g., less than six inches) that is configured to form a portion of or all of a discharge line (e.g., discharge line 122). For example, the tubing line 1022 can have a connector on each end (not shown) capable of connection with and removal from a line of tubing (e.g., discharge line 122), an outlet (e.g., outlet 120), and/or the external receptacle (e.g., external receptacle 160). After urine has passed through the tubing line 1022 and the data has been read from the urine test strip 1062, the tubing line 1022 and the urine test strip 1062 can be disposed of.

In some implementations, a camera, such as a camera built into a portable communication device (e.g., a smartphone, an iPhone, or the like) can be used to read the data on the urine test strip 162. The camera can capture an image of the test strip and the image can be processed using, for example, a smartphone application. The data read from the urine test strip can be sent to a clinician for analysis and/or sent to a cloud-based address for physician access.

In some implementations, the system 100 can include a scale 164. For example, the scale 164 can be disposed underneath the external receptacle 160 such that the scale is configured to measure the weight of fluid (e.g., urine) in the external receptacle 160. The data indicating the weight of the fluid that has been delivered to the external receptacle 160 via the discharge line 122 can be measured at different time intervals and processed to determine how much urine, for example, has been voided by a user of the system 100.

Although described as being intended for use by an adult female, in some implementations the system 100 can be used in adult, pediatric, male, female, and veterinary applications for animals of different species and sizes. In female applications, the assembly 102 can be placed between the legs or labia of the user and held snugly against the external urethra by the pressure of friction from the user's body, by the pressure of the legs or by such means as an undergarment, elastic strips, and/or adhesive tape. In male applications, the assembly 102 can be secured around the penis.

Figure 2:
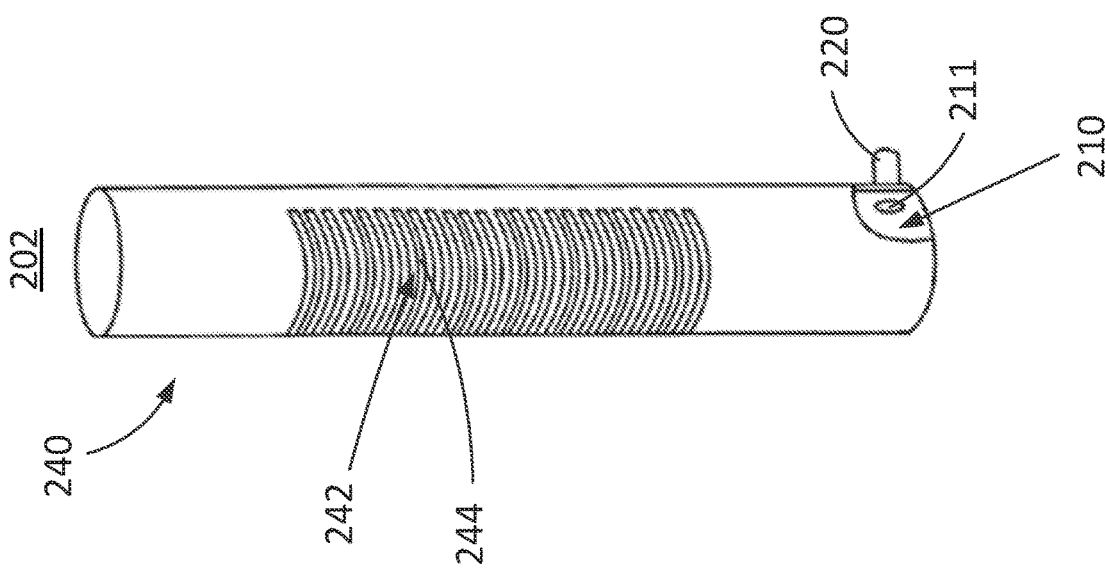
FIG. 2 is a perspective view of an assembly with a portion of the assembly shown in cut away, according to an embodiment.

FIG. 2 is a perspective view of an assembly 202 with a portion of the assembly 202 shown in cut away. The assembly 202 includes a permeable support 240 and a reservoir 210. As shown in FIG. 2, the permeable support 240 and the reservoir 210 can be formed as a unitary structure. For example, the permeable support 240 and the reservoir 210 in combination can form a cylindrical container with closed ends. The cylindrical container with closed ends can define an interior volume. The permeable support 240 can define an inlet 242 in a sidewall of the permeable support 240 such that fluid can flow through the inlet 242 into the interior volume. The reservoir 210 can define an opening 211 and can be coupled to an outlet 220 such that the outlet 220 is in fluid communication with the opening 211. Thus, fluid can flow from the interior volume, through the opening 211, and through the outlet 220.

The permeable support 240 can include one or more membrane supports 244. The membrane supports 244 can be formed as struts that extend across the inlet 242. Said another way, the membrane supports 244 can divide the inlet 242 into an array of distinct slot-shaped openings (or an array of slot-shaped openings can define the membrane supports). The membrane supports 244 can be used to support a permeable membrane (e.g., permeable membrane 230 shown in FIG. 3). For example, the membrane supports 244 can maintain the shape of the permeable membrane 230 against a user's urethral opening and/or the area surrounding a user's urethral opening such that urine flowing from the urethral opening contacts and travels through the permeable membrane 230. The membrane supports 244 can be formed in any suitable shape and/or thickness.

The permeable support 240 and the reservoir 210 can be formed of any suitable material. In some implementations, the permeable support 140 can be flexible. In some implementations, the permeable support 140 can be rigid. In some implementations, the permeable support 240 can be made of plastic, aluminum, a composite of plastic and aluminum, some other metal and/or a composite of plastic and another metal. Additionally, although not shown in FIG. 2, in some implementations the permeable support 240 can be curved.

The assembly 202 can include a permeable membrane 230. FIG. 3 is a perspective view of the assembly 202 with the permeable membrane 230 disposed on an outer surface of the permeable support 240. In some implementations, the permeable membrane 230 can also be disposed on a portion of or on the entire outer surface of the reservoir 210. The permeable membrane 230 can be at least partially supported by the membrane supports 244 (shown in FIG. 2) such that the membrane supports 244 maintain the permeable membrane 230 against or near a urethral opening of a user.

The permeable membrane 230 can be formed of a material that is urine permeable and has wicking properties. The permeable membrane 230 can have a high absorptive rate and a high permeation rate such that urine can be rapidly wicked by the permeable membrane 230 and/or transported through the permeable membrane 230. In some implementations, the permeable membrane 230 can be a ribbed knit fabric. In some implementations, the permeable membrane 230 can include and/or have the moisture-wicking characteristic of gauze, felt, terrycloth, thick tissue paper, and/or a paper towel. In some implementations, the permeable membrane 230 can be soft and/or minimally abrasive such that the permeable membrane 230 does not irritate the skin of the user. The permeable membrane 230 can be configured to wick fluid away from the urethral opening and/or the skin of the user such that the dampness of the skin of the user is lessened and infections are prevented. Additionally, the wicking properties of the permeable membrane 230 can help prevent urine from leaking or flowing beyond the assembly onto, for example, a bed. In some implementations, the permeable membrane 130 can be formed of fine denier polyester fibers coated with a thermoplastic water-based binder system. The tensile with the Webb direction can be, for example, about 45 lbs/inch$^2$ measured using an Instron test method. The weight per permeable membrane can be, for example, about 12 grams measured using the Mettle Gram Scale. The thickness per ten permeable membrane can be, for example, about 2.5", measured using the Gustin-Bacon/Measure-Matic.

In some implementations, the permeable membrane 230 can be formed as a sock or sleeve that can be slid over the permeable support 240. In some implementations, the permeable membrane 230 can be formed as a sheet that can be wrapped partially or completely around the permeable support 240. The permeable membrane 230 can be secured in place with one or more securing elements 252. In some implementations, the securing elements 252 can be impermeable and form a portion of or all of an impermeable layer (similar to impermeable layer 150 with reference to assembly 100 of FIG. 1). In some implementations, the securing elements 252 can include elastic bands (e.g., rubber bands), water-resistant adhesive tape, spring clips, hook and loop fasteners, zippers, snaps, and/or any other suitable securing element. In other implementations, the permeable membrane 230 can be secured in place via friction between the permeable membrane 230 and the permeable support 240.

FIG. 4 is a schematic illustration the assembly 202 as part of a system 200. The system 200 includes an external receptacle 260 and a vacuum source 270. The external receptacle 260 can be the same or similar in structure and/or function as the external receptacle 160 described above with reference to the system 100. The vacuum source 270 can be the same or similar in structure and/or function as the vacuum source 170 described above with reference to the system 100. The assembly 202 can be fluidically coupled to the external receptacle 260 via a discharge line 122. The external receptacle 260 can be fluidically coupled to the vacuum source 270 via a vacuum line 224.

In use, the system 200 can be positioned such that the assembly 202 is abutting and/or near the urethral opening of the user. In particular, the assembly 202 can be positioned such that the inlet 242 and membrane supports 244 are facing the urethral opening such that urine exiting the urethral opening can travel through the permeable membrane 230, through the inlet 242, through the interior volume defined by the permeable support 240 and the reservoir 210, and through the outlet 220. The assembly 202 can be arranged relative to the urethral opening of the user such that gravity causes or assists urine entering the permeable support 240 in traveling to the reservoir 210. Similarly as described above with reference to system 100, the vacuum source 270 can assist and/or provide the pressure differential needed to draw fluid voided from the urethral opening into the inner volume of the assembly 202, and then from the reservoir 210 into the external receptacle 260. The vacuum source 270 can have a sufficiently high vacuum strength and air volume transport rate such that rapid air and liquid aspiration is maintained over a portion of or the entire permeable membrane 230. Additionally, the inlet 242 can be sized and shaped such that the inlet 242 is larger than the area of the permeable membrane 230 that is configured to be wetted by urine flow in operation. Thus, the partial vacuum created by the vacuum source 270 in combination with the inlet 242 and the permeable membrane 230 can draw the urine contacting the permeable membrane 230 into the assembly 202. In some implementations, however, the inlet 242 should not be distributed over too large of an area of the permeable support 240 because the partial vacuum strength may be reduced, thereby reducing the urine collection rate and the efficiency of the system 200. The vacuum source 270 can be fluidically coupled to the external receptacle 260 via a vacuum line 224 such that gaseous fluid is drawn from the external receptacle 260 via the vacuum line 224. As a result of the decrease in pressure within the external receptacle 260 caused by the drawing of gaseous fluid out of the external receptacle 260, liquid and/or gaseous fluid can be drawn from the reservoir 210, through the outlet 220, through the discharge line 222, and into the external receptacle 260.

FIG. 5 is a schematic illustration of a system 300. The system 300 includes an assembly 302. The assembly 302 can be the same or similar in structure and/or function to the assembly 102 or the assembly 202 described above. The system 300 can include an external receptacle 360 and a vacuum source 370. The external receptacle 360 can be the same or similar in structure and/or function as the external receptacle 160 and/or the external receptacle 260 described above. The vacuum source 370 can be the same or similar in structure and/or function as the vacuum source 170 and/or the vacuum source 270 described above.

As shown in FIG. 5, the system 300 can include a chassis 372. The vacuum source 370 can be mounted on the chassis 372. A discharge pipe 374 and a vacuum intake pipe 376 can be mounted on or disposed within the chassis 372. The discharge pipe 374 can be fluidically coupled to the assembly 302 via a discharge line 322. The vacuum intake pipe 376 can be fluidically coupled to a vacuum line extending away from the chassis 372. The chassis 372 can be mounted on and/or coupled to the external receptacle 360. For example, in some implementations, the chassis can include helical threads configured to engage with helical threads on the external receptacle 360 such that the chassis 372 can engage with the external receptacle 360.

In use, the system 300 can be positioned such that the assembly 302 is abutting and/or near the urethral opening of the user. In particular, the assembly 302 can be positioned such that one or more openings in the permeable support (not shown) of the assembly 302 face the urethral opening such that urine exiting the urethral opening can travel through a permeable membrane of the permeable support, through the one or more openings, through an interior volume defined by the permeable support and a reservoir of the assembly 302, and through an outlet of the assembly 302 into the discharge line 322. The assembly 302 can be arranged relative to the urethral opening of the user such that gravity causes urine entering the permeable support to travel to the reservoir. Similarly as described above with reference to system 100 and/or system 200, the vacuum source 370 can assist and/or provide the pressure differential needed to draw fluid (e.g., urine) voided from the urethral opening into the inner volume of the assembly 302, and then from the reservoir, through the discharge line 322, and into the external receptacle 360. The vacuum source 370 can have a sufficiently high vacuum strength and air volume transport rate such that rapid air and liquid aspiration is maintained over a portion of or the entire permeable membrane. The vacuum source 370 can be fluidically coupled to the external receptacle 360 via the vacuum intake pipe 376 such that gaseous fluid is drawn from the external receptacle 360 via the vacuum intake pipe 376. The gaseous fluid can then be released from the system 300 via a vacuum line 324. As a result of the decrease in pressure within the external receptacle 360 caused by the drawing of gaseous fluid out of the external receptacle 360, liquid and/or gaseous fluid can be drawn from the assembly 302, through the discharge line 322, and into the external receptacle 360.

In some implementations, rather than the permeable support and the reservoir being combined as a unitary or integral structure and shaped as a cylinder of constant diameter (e.g., permeable support 240 and reservoir 210 of FIG. 2), a permeable support and a reservoir can be formed as a unitary structure having any suitable shape, as shown in FIGS. 6A-6C, which are schematic illustrations of various assembly shapes. For example, as shown in FIG. 6A, an assembly 402 includes a permeable support 440 and a reservoir 410. The permeable support 440 and the reservoir 410 are formed as a unitary structure having a curved shape. The permeable support 440 defines an inlet 442 and includes a number of membrane supports 444. The membrane supports 444 extend across the inlet 442. In other words, the membrane supports 444 divide the inlet 442 into a number of discrete inlet portions.

As shown in FIG. 6B, an assembly 502 includes a permeable support 540 and a reservoir 510. The permeable support 540 and the reservoir 510 are formed as a unitary structure having a straight shape with a larger diameter end portion. Thus, the reservoir 510 can have a larger diameter than the permeable support 540. The permeable support 540 defines an inlet 542 and includes a number of membrane supports 544. The membrane supports 544 extend across the inlet 542. In other words, the membrane supports 544 divide the inlet 542 into a number of discrete inlet portions.

As shown in FIG. 6C, an assembly 602 includes a permeable support 640 and a reservoir 610. The permeable support 640 and the reservoir 610 are formed as a unitary structure having concave sides. The permeable support 640 defines an inlet 642 and includes a number of membrane supports 644. The membrane supports 644 extend across the inlet 642. In other words, the membrane supports 644 divide the inlet 642 into a number of discrete inlet portions.

FIG. 7 is a perspective view of an assembly 702 with a portion of the assembly 702 shown in cut away. The assembly 702 can be similar in structure and/or function to the assembly 202 described above with respect to FIG. 2. For example, the assembly 702 includes a permeable support 740 and a reservoir 710. The permeable support 740 and the reservoir 710 are formed as an integral, unitary cylindrical container with closed ends. The cylindrical container with closed ends defines an interior volume. The permeable support 740 can define an inlet 742 in a sidewall of the permeable support 740 such that fluid can flow through the inlet 742 into the interior volume. The permeable support 740 can include one or more membrane supports 744. The membrane supports 744 can be the same or similar in structure and function to the membrane supports 244 described above with reference to the permeable support 240.

Rather than including an outlet extending from a side of the reservoir 710, the outlet 720 of the reservoir 710 can be formed as an elongated tube positioned within the reservoir 710 and extending through a portion of the reservoir 710, through the permeable support 740, and out a top end of the permeable support 740. Thus, fluid can flow (e.g., via suction applied to the outlet 720) from the interior volume, through the outlet 720, and out the top of the apparatus 702.

FIG. 8 is a perspective view of an assembly 802. The assembly 802 can be similar in structure and/or function to the assembly 702 described above with respect to FIG. 7. For example, the assembly 802 includes a permeable support 840 and a reservoir 810. The permeable support 840 and the reservoir 810 are formed as an integral, unitary curved cylindrical container with closed ends. The cylindrical container with closed ends defines an interior volume. The permeable support 840 can define a number of inlets 842 in a sidewall 844 of the permeable support 840 such that fluid can flow through the number of inlets 842 into the interior volume. The sidewall 844 can support a permeable membrane, such as permeable membrane 130 described above with reference to FIG. 1. In particular, the portions of the sidewall 844 defining and separating the number of inlets 842 can be the same or similar in structure and function to the membrane supports 244 described above with reference to the permeable support 240. The assembly 802 can include an outlet 820 similar to the outlet 720 describe above with reference to the assembly 702. For example, the outlet 820 can be formed as an elongated tube positioned within the reservoir 810 and extending through a portion of the reservoir 810, through the permeable support 840, and out a top end of the permeable support 840. Thus, fluid can flow (e.g., via suction applied to the outlet 820) from a urethral opening of a user, through the number of inlets 842 into the interior volume, to the reservoir 810, through the outlet 820, and out the top of the apparatus 802.

In some implementations, the assembly 802 can include a permeable membrane (not shown) that includes a spray-on fabric, such as the spray-on fabric developed by Fabrican, Ltd. of London, England. The spray-on fabric can be applied to the exterior of the permeable support 840 and/or the reservoir 810. The spray-on fabric can include a liquid suspension and can be applied via, for example, a spray gun or an aerosol can. The spray-on fabric can be formed by the cross-linking of fibers which adhere to the exterior of the permeable support 840 such that the spray-on fabric forms an instant non-woven fabric when applied to the exterior of the permeable support 840 and/or the reservoir 810.

In some implementations, the assembly 802 can include a permeable membrane (not shown) similar in structure and function to any of the permeable membranes described above (such as, for example, permeable membrane 230) can be secured to the permeable support 840 and/or the reservoir 810. In some implementations, such as is shown in FIG. 9, the assembly 802 can include a permeable membrane 830 covering a portion or all of the permeable support 840 and/or the reservoir 810. The assembly 802 can also include an impermeable layer 850. The permeable support 840 and the impermeable layer 850 can form, in combination, a sheath-like structure shaped and sized to be secured around at least a portion of the permeable support 840 and at least a portion of the reservoir 810. The impermeable layer 850 can be disposed relative to the permeable support 840, reservoir 810, and permeable membrane 830 such that the permeable membrane 830 is configured for interfacing with a urethral opening and/or the area surrounding the urethral opening of a user and at least a portion of the number of inlets 842 are not covered by the impermeable layer 850 such that urine from the urethral opening can flow through the permeable membrane 830, through the number of inlets 842, and into the inner volume of the assembly 802. The impermeable layer 850 can be disposed such that the impermeable layer 850 can direct fluid toward the reservoir 810 and reduce and/or prevent fluid from exiting the assembly 802 except via the outlet 820.

The impermeable layer 850 can include one or more extension portions 856. The one or more extension portions 856 can extend away from the permeable membrane 830 and/or the permeable support 840 such that the one or more extension portions 856 can be gripped by a user or caregiver without contacting the permeable membrane 830. Thus, the one or more extension portions 856 can be used to remove the permeable membrane 830 and the impermeable layer 850 from the permeable support 840. In some implementations, the one or more extension portions 856 can be shaped as an elongated tab that extends along the length of the assembly 802 on one or more sides of the assembly 802. Although not shown, in some implementations, the permeable membrane 830 and/or the impermeable layer 850 can include a handle (not shown). The handle can be shaped as a hoop and disposed on one end of the permeable membrane 830 and/or the impermeable layer 850 to assist in positioning and removing the permeable membrane 830 and/or the impermeable layer 850 from the permeable support 840 and/or the reservoir 810.

In some implementations, the permeable membrane 830 can be formed as a sheath with a closed end such that the permeable membrane 830 can be pulled over the permeable support 840 and the reservoir 810 like a sock. For example, the permeable membrane 830 can be heat sealed on one end. In such implementations, the impermeable layer 850 can be secured to a portion of the side and/or bottom of the permeable membrane 830. In other implementations, the permeable membrane 830 can be formed as a sheath with two open ends that can be pulled over the permeable support 840 and the reservoir 810. In such implementations, the end of the permeable membrane 830 near the reservoir 810 can be left uncovered, and the impermeable layer 850 can be secured to a portion of the side and/or the bottom of the permeable membrane 830. In some implementations, the permeable membrane 830 can be a piece of material smaller than the external surface area of the permeable support 840. The permeable membrane 830 can be heat sealed to the impermeable layer 850 such that the combination of the permeable membrane 830 and the impermeable layer 850 form a sheath that can be secured to permeable support 840 and/or the reservoir 810 via, for example, pulling over the permeable support 840 and/or the reservoir 810 like a sock.

Figure 10:
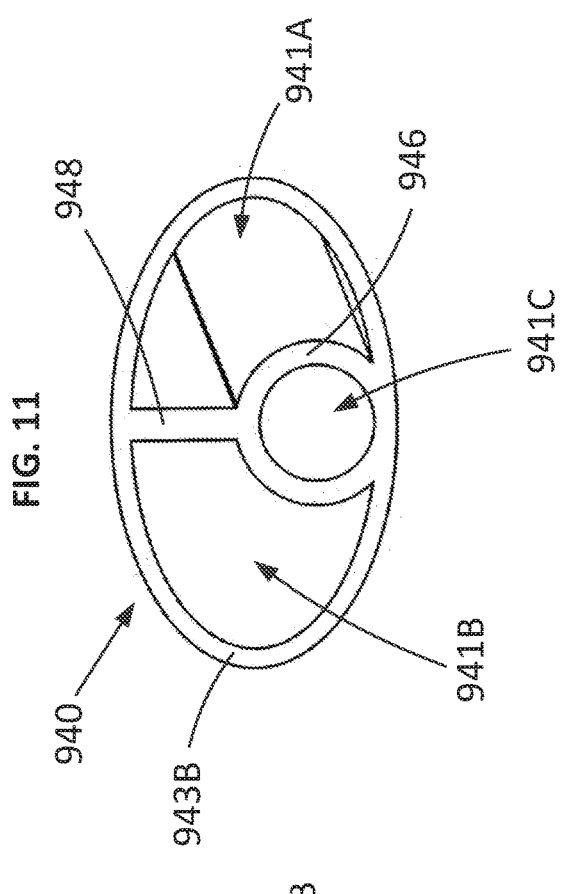
FIG. 10 is a perspective view of a first end of a permeable support, according to an embodiment.
Figure 11:
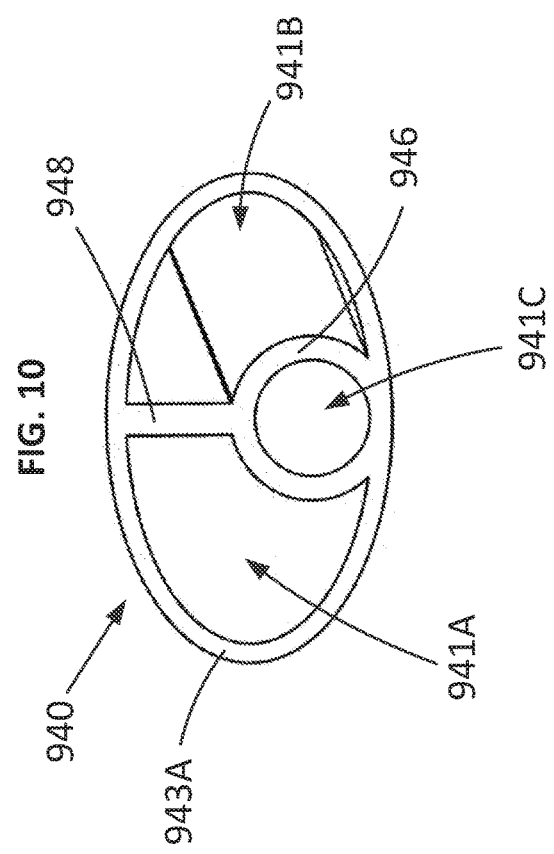
FIG. 11 is a perspective view of a second end of a permeable support, according to an embodiment.

In some implementations, the assemblies described herein can include internal structures to direct fluid flow and/or provide structural support. Additionally, in some implementations, the assemblies described herein can include a first end cap and a second end cap. For example, the assemblies described herein can include the features shown and described with respect to FIGS. 10-13. FIGS. 10 and 11 are a perspective view of a first end 943A and perspective view of a second end 943B, respectively, of a permeable support 940. The permeable support 940 can include a tunnel 946 and a spine 948. The tunnel can define a first chamber 941C. The spine 948 can divide an inner volume of the permeable support 940 into a second channel 941A and a third channel 941B. The first chamber 941C, the second channel 941A, and the third channel 941B can each run the length of the permeable support 940 and run parallel to one another. The spine 948 can be used to strengthen the permeable support 940 such that the permeable support 940 maintains an intended shape. The permeable support 940 can include one or more openings (not shown) in a sidewall of the permeable support 940. The one or more openings can be aligned with the second channel 941A and the third channel 941B such that fluid can flow through the one or more openings into the second channel 941A and the third channel 941B. Although only one spine 948 is shown, in some implementations, the permeable support 940 can include additional spines such that the permeable support 940 is divided into additional channels. In some implementations, the permeable support 940 can be formed without a spine such that the permeable support 940 only defines one channel in addition to the third channel 941C defined by the tunnel 946.

Figure 12:
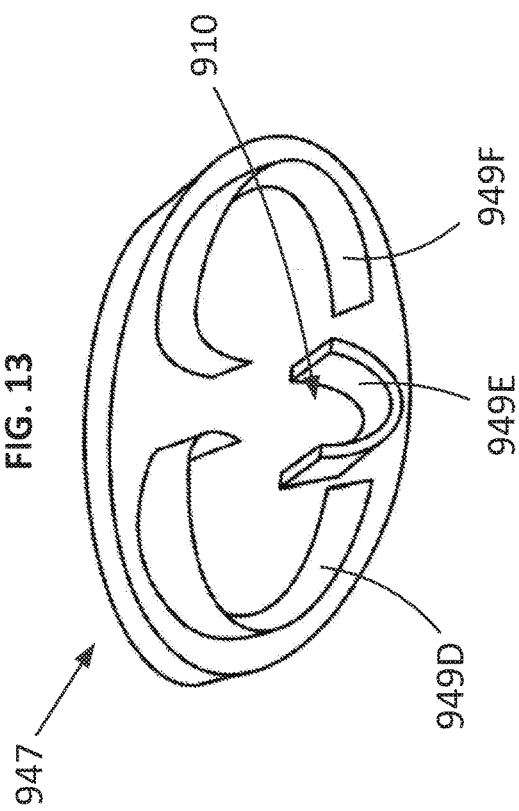
FIG. 12 is a perspective view of a first end cap, according to an embodiment.

FIG. 12 is a perspective view of a first end cap 945 configured to be coupled to the first end 943A of the permeable support 940. The first end cap 945 includes a first flange 949A, a second flange 949B, and a third flange 949C. The third flange 949C defines an opening 941D through the first end cap 945. The first flange 949A, the second flange 949B, and the third flange 949C can be shaped and sized such that the first flange 949A, the second flange 949B, and the third flange 949C can be coupled within the third chamber 941B, the second chamber 941A, and the first chamber 941C, respectively. In some implementations, the first flange 949A, the second flange 949B, and the third flange 949C can be shaped and sized such that the first flange 949A, the second flange 949B, and the third flange 949C are configured to engage with the third chamber 941B, the second chamber 941A, and the first chamber 941C, respectively.

Figure 13:
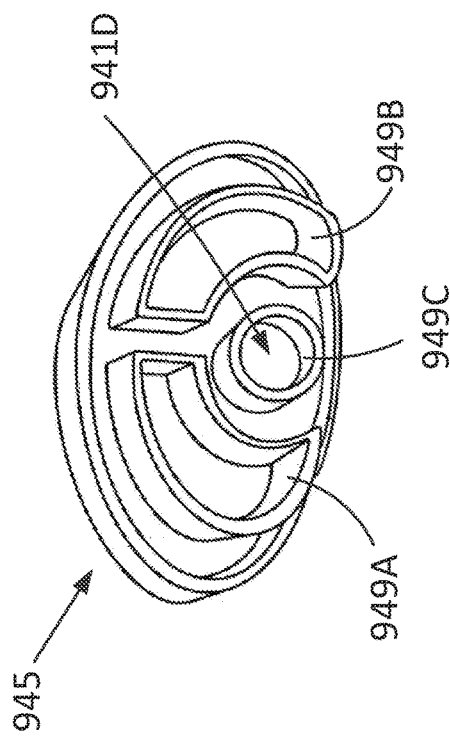
FIG. 13 is a perspective view of a second end cap, according to an embodiment.

FIG. 13 is a perspective view of a second end cap 947 configured to be coupled to the second end 943B of the permeable support 940. The second end cap 947 includes a first flange 949D, a second flange 949E, and a third flange 949F. The first flange 949D, the second flange 949E, and the third flange 949F can be shaped and sized such that the first flange 949D, the second flange 949E, and the third flange 949F can be coupled within the second chamber 941A, the first chamber 941C, and the second chamber 941B, respectively. In some implementations, the second end cap 947 can be shaped and sized such that the second end cap 947 can sealingly engage with the first chamber 941C, the second chamber 941A, and the third chamber 941B to prevent fluid leakage.

In an assembled configuration in which the first end cap 945 is coupled to the first end 943A of the permeable support 940 and the second end cap 947 is coupled to the second end 943B of the permeable support 940, the second end cap 947 and/or the permeable support 940 can define a reservoir 910 for collection of fluid (e.g., urine). The third flange 949C of the first end cap 945 can define an outlet for fluid collected within the reservoir 910. In some implementations, an external tube can be inserted through the first end cap 945 via the opening 941D defined by the third flange 949C and through the third channel 941C defined by the tunnel 946 until an end of the external tube reaches fluid in the reservoir defined by the second end cap 947 and/or the permeable support 940. The external tube can then be used to remove the fluid via suction. In some implementations, an external tube can be coupled to the first end cap 945, rather than extended through the first end cap 945 and into the permeable support 940. In such embodiments, suction can be applied via the external tube such that fluid (e.g., urine) in the reservoir 910 can be transported via suction through the first channel 941C and out of the opening 941D. Although not shown, in some implementations, the second flange 949C of the first end cap 945 can extend from both sides of the first end cap 945 such that the second flange 949C can form a male fitting for an external tube such that the external tube can be coupled to the second flange 949C.

In some implementations, the tunnel 946 can be formed such that a gap exists between the end of the tunnel 946 and the face of the second end cap 947 such that the tunnel 946 does not prevent fluid from flowing from the second channel 941A and/or the third channel 941B into the first channel 941C. In some implementations, the tunnel 946 is formed such that the gap between the tunnel 946 and the face of the second cap 947 is small such that a large amount of fluid does not accumulate in the reservoir 910 before reaching a height capable of being suctioned via the tunnel 946.

In some implementations, the first end cap 945 and/or the second end cap 947 can be rigid. The first end cap 945 and/or the second end cap 947 can be, for example, injection molded and formed of plastic, such as ABS or nylon. In some implementations, the first end cap 945 and/or the second end cap 947 can be flexible. In some implementations, the first end cap 945 and/or the second end cap 947 can be made of any suitable material using any suitable process.

In some implementations, the permeable support 940 can be formed of a soft material, such as, for example, polyurethane, polyethylene, or synthetic rubber. The permeable support 940 can be formed via an extrusion process. In some implementations, the material used to form the permeable support 940 can be coiled during the extrusion process such that the permeable support 940 has a curved shape to improve the fit of the permeable support 940 and/or a permeable membrane coupled to the permeable support 940 with a user's urethral opening and/or the region of a user's body surround the urethral opening. In some implementations, the permeable support 940 can be formed via injection molding. In some implementations, the permeable support 940 can be rigid or flexible, and can be formed of any suitable material or combination of materials.

Figure 15:
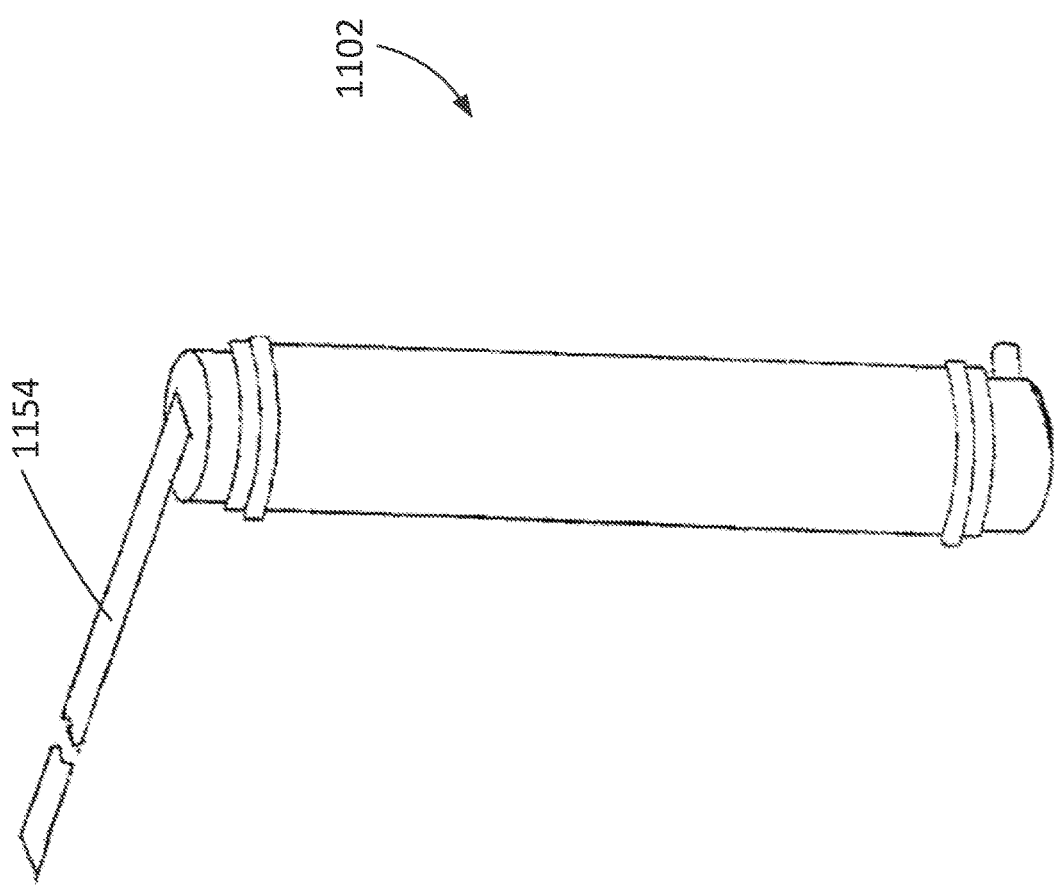
FIG. 15 is a perspective view of an assembly, according to an embodiment.

In some implementations, a stabilizer can be used to maintain any of the assemblies described herein in a particular position relative to a user's body. For example, FIG. 15 is a perspective view of an assembly 1102. The assembly 1102 can be the same or similar in structure and function to the assembly 202 described above with reference to FIG. 3. As shown in FIG. 15, a stabilizer 1154 is coupled to the assembly 1102 such that the stabilizer 1154 can maintain the assembly 1102 in a certain position relative to a user's body. For example, in some situations of use, such as incontinence, disability that limits or impairs mobility, restricted travel conditions (e.g., conditions experienced by pilots, drivers, and/or workers in hazardous areas), monitoring purposes, or for clinical testing, the stabilizer 1154 can aid in maintaining the engagement between the assembly 1102 and the user's urethral opening and/or the area surrounding the urethral opening. In some implementations, the stabilizer 1154 can be coupled to or integrally formed with an impermeable layer of the assembly 1102. In some implementations, a first end of the stabilizer 1154 can be coupled to an impermeable layer of the assembly 1102 and a second end of the stabilizer 1154 can be coupled to a user's body (e.g., via adhesive or tape) or to an apparatus occupied by the user (e.g., a bed or wheelchair) to stabilize the position of the assembly 1102 relative to a user's urethral opening and/or the area surrounding the urethral opening. The stabilizer 1154 can be a thin, pliable strip of material. For example, in some implementations the stabilizer 1154 can include tape, gauze, cotton, cloth, or plastic. The stabilizer 1154 can be any suitable length and/or width. In some implementations, the stabilizer 1154 can be as thin as a single thread. The stabilizer 1154 can be attached to the user's body or an apparatus occupied by the user via any suitable attachment mechanism, such as via skin-safe adhesive, tape, a hook, tying the stabilizer 1154 into a knot, or any other suitable attachment mechanism.

In some implementations, the permeable membrane can include a web of flexible porous material. For example, as shown in FIG. 16, a permeable support 1240 can be formed of a web of flexible porous material and shaped such that the permeable support 1240 defines a channel 1240B. The flexible porous material can be, for example, spun plastic fibers. The spun plastic fibers can be, for example, spun polyester fibers such as is used in a typical scouring pad. The permeable support 1240 can have a tubular shape. The permeable support 1240 can be shaped such that the permeable support 1240 is cylindrical or non-cylindrical. As shown in FIG. 17, which is a cross-section of the permeable support 1240 shown in FIG. 16 taken along the line 17-17, the channel 1240B can be shaped and configured to receive an outlet tube 1220.

As shown in FIG. 18, a permeable membrane 1230 can be coupled to the permeable support 1240. The permeable membrane 1230 can be the same or similar in structure and/or function to any of the permeable membranes described herein. The permeable support 1240 can have a first closed end 1243A and a second closed end 1243B. The second closed end 1243B and the bottom of the permeable support 1240 can collectively form a reservoir 1210 to collect fluid that enters the channel 1240B via the permeable membrane 1230 and the permeable support 1240. The outlet tube 1220 can be inserted into the channel 1240B such that fluid that travels into the permeable support 1240 can be removed from the permeable support 1240 via the channel 1240B and the outlet tube 1220 (via, for example, a vacuum source).

In some implementations, a web of flexible porous material can be in the form of a flexible sheet rolled or folded into a tubular shape. For example, as shown in FIG. 19, a permeable support 1340 can include a flexible sheet formed of a web of flexible porous material and rolled or folded such that the permeable support 1340 defines a channel 1340B. The flexible porous material can be, for example, spun plastic fibers. The spun plastic fibers can be, for example, spun polyester fibers such as is used in a typical scouring pad. The permeable support 1340 can be made to have a tubular shape by rolling a first end of the flexible sheet towards a second end of the flexible sheet such that the first end and the second end meet along an intersection plane identified by 1340A. The permeable support 1340 can then be secured in this shape using securing elements 1352. The securing elements 1352 can include any suitable securing element, such as, for example, adhesive or glue. In some implementations, rather than using one or more separate securing elements 1352, the permeable support 1340 can be secured in a rolled or folded configuration via compression from a permeable membrane (e.g., the permeable membrane 1330 described below). The permeable support 1340 can be shaped such that the permeable support 1340 is cylindrical or non-cylindrical. As shown in FIG. 20, which is a cross-section of the permeable support 1340 shown in FIG. 19 taken along the line 20-20, the channel 1340B can be shaped and configured to receive an outlet tube 1320.

As shown in FIG. 21, a permeable membrane 1330 can be coupled to the permeable support 1340. The permeable membrane 1330 can be the same or similar in structure and/or function to any of the permeable membranes described herein. For example, the permeable membrane 1330 can include a wicking material wrapped around the permeable support 1340. In some implementations, the permeable membrane 1330 can include a wicking material attached or sprayed onto the web of flexible porous material prior to folding the web into the tubular shape. The permeable support 1340 can have a first closed end 1343A and a second closed end 1343B. The second closed end 1343B and the bottom of the permeable support 1340 can collectively form a reservoir 1310 to collect fluid that enters the channel 1340B via the permeable membrane 1330 and the permeable support 1340. The outlet tube 1320 can be inserted into the channel 1340B such that fluid that travels into the permeable support 1340 can be removed from the permeable support 1340 via the channel 1340B and the outlet tube 1320 (via, for example, a vacuum source).

FIGS. 22-26 are various views of an assembly 1402 shown in a variety of configurations. As shown in FIGS. 22-24, which are a front view, back view, and side view of an assembly 1402, respectively, in some implementations, the permeable support 1440 can be shaped as a flexible sheet. The flexible sheet can be formed of a porous flexible web of spun plastic fibers, such as, for example, spun polyester fibers such as is used in a typical scouring pad. In some implementations, polyester fibers are used due to their ability to remain odor free. In some implementations, the flexible sheet can be formed of any suitable type of fibers. An outlet tube 1420 can be attached to the permeable support 1440 via any suitable attachment mechanism. For example, the outlet tube 1420 can be attached to the permeable support 1440 via securement elements 1452, such as, for example, adhesive tape.

The assembly 1402 can include an impermeable layer 1450. As shown in FIG. 25, which is a side view of the assembly 1402 including the impermeable layer 1450, the impermeable layer 1450 can be coupled to the permeable support 1440 such that fluid traveling through the permeable support 1440 can be directed toward an end of the outlet tube 1420. The impermeable layer 1450 can, in combination with the permeable support 1440, define a reservoir 1410 for collection of fluid that has entered the assembly 1402 via the permeable support 1440 and traveled to the bottom of the assembly 1402. For example, the bottom end of the impermeable layer 1450 and/or the bottom end of the permeable support 1440 can be a closed end such that fluid does not exit the assembly 1402 except via the outlet tube 1420 (via, for example, a vacuum source).

The assembly 1402 can also include a permeable membrane 1430. As shown in FIG. 26, which is a front view of the assembly 1402, the permeable membrane 1430 can be disposed on the outer surface of the permeable support 1440 or on the outer surface of the permeable support 1440 and the backing 1450. The permeable membrane 1430 can be the same or similar to any of the permeable membranes described herein.

Figure 27:
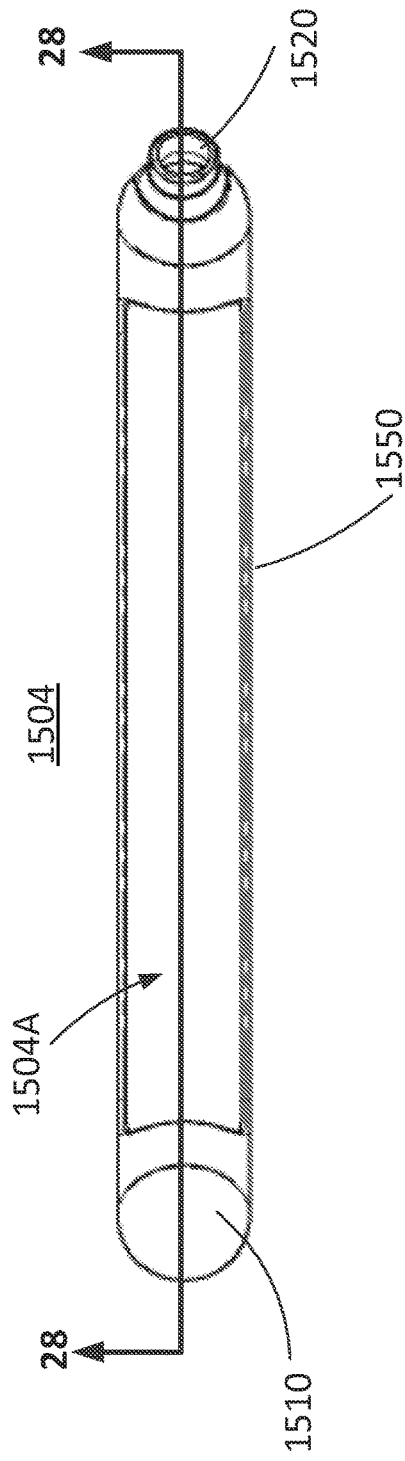
FIG. 27 is a top view of an impermeable casing, according to an embodiment.
Figure 28:
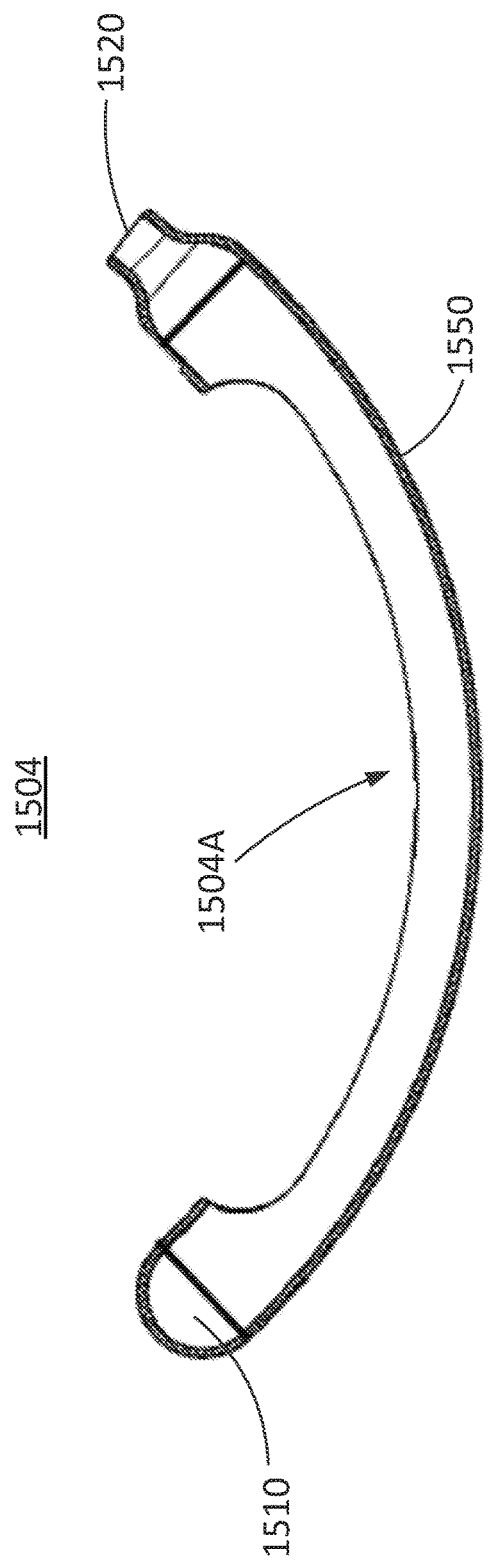
FIG. 28 is a cross-sectional side view of the impermeable casing of FIG. 27 taken along line 28-28.

In some implementations, the reservoir, the impermeable layer, and/or a portion of the outlet can be formed as an integral, one piece structure. For example, FIGS. 27 and 28 are a top view and a cross-sectional side view, respectively, of an impermeable casing 1504. The impermeable casing 1504 includes an impermeable layer 1550, an outlet 1520, and a reservoir 1510. The outlet 1520 and the reservoir 1510 are coupled together by the impermeable layer 1550. The impermeable layer 1550 defines an elongated opening 1504A. The outlet 1520 can be configured to receive tubing such that fluid can be removed from an interior of the impermeable casing 1504 via the tubing. The impermeable casing 1504 can be formed of a flexible and compliant, impermeable material, such as, for example, silicone and/or another polymer. Additionally, the impermeable casing 1504 can be curved such that, in a configuration in which the impermeable casing 1504 includes a permeable membrane and/or a permeable support, the impermeable casing 1504 can expose the permeable membrane for a comfortable and secure interface for engagement with a user's urethral opening.

Figure 31:
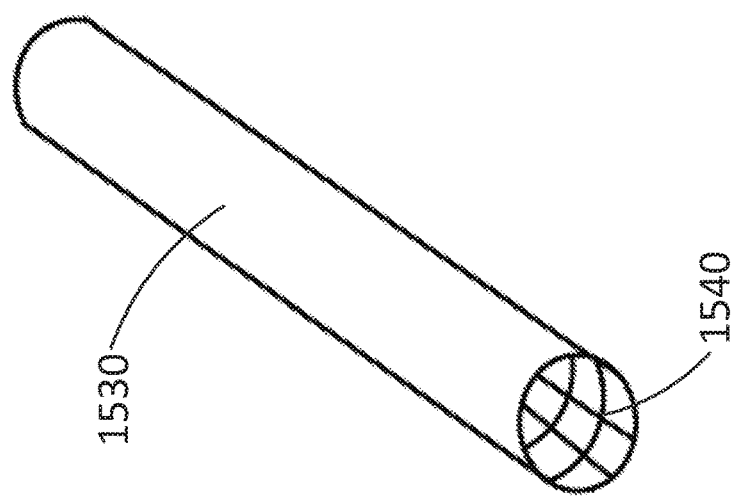
FIG. 31 is a perspective view of the permeable support of FIG. 29 with a permeable membrane.
Figure 30:
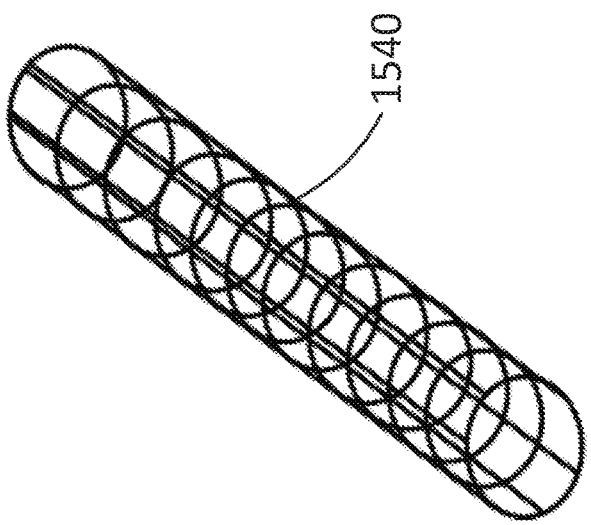
FIG. 30 is a perspective view of the permeable support of FIG. 29 in a second configuration.
Figure 29:
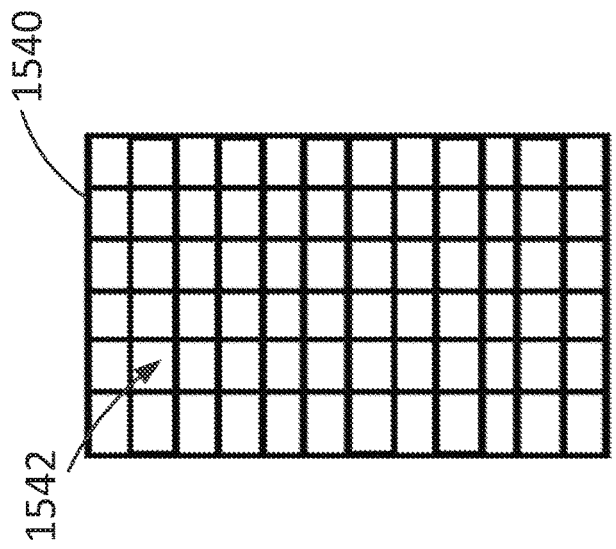
FIG. 29 is a top view of a permeable support in a first configuration, according to an embodiment.

In some implementations, the impermeable casing 1504 can be configured to contain a permeable membrane disposed over a permeable support. For example, FIG. 29 is a top view of a permeable support 1540. The permeable support 1540 can define a number of inlets 1542. The inlets 1542 can be symmetrical or non-symmetrical across the permeable support 1540. In some implementations, the permeable support 1540 can be formed of a porous spun plastic or plastic netting material. The permeable support 1540 can be flexible and compliant. In some implementations, the permeable support 1540 can be formed of flexible polypropylene, nylon, polyester, another plastic, a natural material, and/or any other suitable material. As shown in FIG. 30, the permeable support 1540 can be folded or rolled into a tubular shape. As shown in FIG. 31, the permeable support 1540 can be covered with a permeable membrane 1530. For example, the permeable support 1540 can form a flexible framework over which the permeable membrane 1530 can fit snugly.

The permeable support 1540 in combination with the permeable membrane 1530 can be disposed within the interior of the impermeable casing 1504 such that the permeable support 1540 can maintain the permeable membrane 1530 against or near a source of moisture (e.g., a urethral opening) through the elongated opening 1504A. The permeable membrane 1530 and the permeable support 1540 can be positioned within the impermeable casing 1504 using any suitable method. For example, in some implementations, the permeable membrane 1530 can be pulled over or wrapped around the permeable support 1540. The combination of the permeable membrane 1530 and the permeable support 1540 can then be inserted through the elongated opening 1504A of the impermeable casing 1504 and the impermeable casing 1504 can be stretched and/or otherwise maneuvered such that the impermeable casing 1504 surrounds the permeable membrane 1530 except in the area of the elongated opening 1504A.

In some implementations, the permeable membrane 1530 (e.g., a tubular gauze) can first be disposed over a hollow plastic pipe (not shown). The pipe covered with the permeable membrane 1530 can be inserted through the opening 1520 of the impermeable casing 1504 such that the permeable membrane 1530 is positioned within the impermeable casing 1504. The permeable support 1540 can then be formed into a configuration such that the permeable support 1540 can function as a hollow framework for the permeable membrane 1530 (e.g., a tubular or cylindrical shape as shown in FIG. 30). The permeable support 1540 can then be inserted through the pipe and/or the opening 1520 such that the permeable support 1540 is coextensive and arranged within the permeable membrane 1530. The pipe can then be removed from the permeable membrane 1530 and the permeable support 1540 via the opening 1520 while the permeable membrane 1530 and the permeable support 1540 are grasped such that the permeable membrane 1530 and the permeable support 1540 remain within the impermeable casing 1504.

In some implementations, the permeable membrane 1530 (e.g., a tubular gauze) can first be disposed over a hollow plastic pipe (not shown). The permeable support 1540 can then be formed into a configuration such that the permeable support 1540 can function as a hollow framework for the permeable membrane 1530 (e.g., a tubular or cylindrical shape as shown in FIG. 30). The permeable support 1540 can then be inserted through the pipe such that the permeable support 1540 is coextensive and arranged within the permeable membrane 1530. The pipe can then be removed from the permeable membrane 1530 and the permeable support 1540 while the permeable membrane 1530 and the permeable support 1540 are grasped such that the permeable membrane 1530 and the permeable support 1540 remain within the impermeable casing 1504. If the permeable membrane 1530 is longer than necessary, such as if the permeable membrane 1530 is longer than the permeable support 1540, the permeable membrane 1530 can be cut (e.g., with scissors) to the desired length. The permeable membrane 1530 in combination with the permeable support 1540 can then be inserted into the impermeable casing 1504 via the elongated opening 1504A.

In some implementations, the permeable membrane 1530 can be attached to the permeable support 1540 via an adhesive or adhesive tape. In some implementations, the permeable membrane 1530 can be attached to the permeable support 1540 via compression from the impermeable casing 1504. For example, the permeable membrane 1530 can be wrapped around the permeable support 1540 and inserted into the impermeable casing 1504 such that the impermeable casing 1504 applies compression to the permeable membrane 1530 and the permeable support 1540 such that the permeable membrane 1530 and the permeable support 1540 each maintain their shape and attachment to each other. In some implementations, the permeable membrane 1530 can be secured to the permeable support 1540 by compression as a result of the permeable membrane 1530 having elastic properties. For example, the permeable membrane 1530 can include tubular compression gauze that can be applied to the permeable support 1540 as a sleeve.

Figure 32:
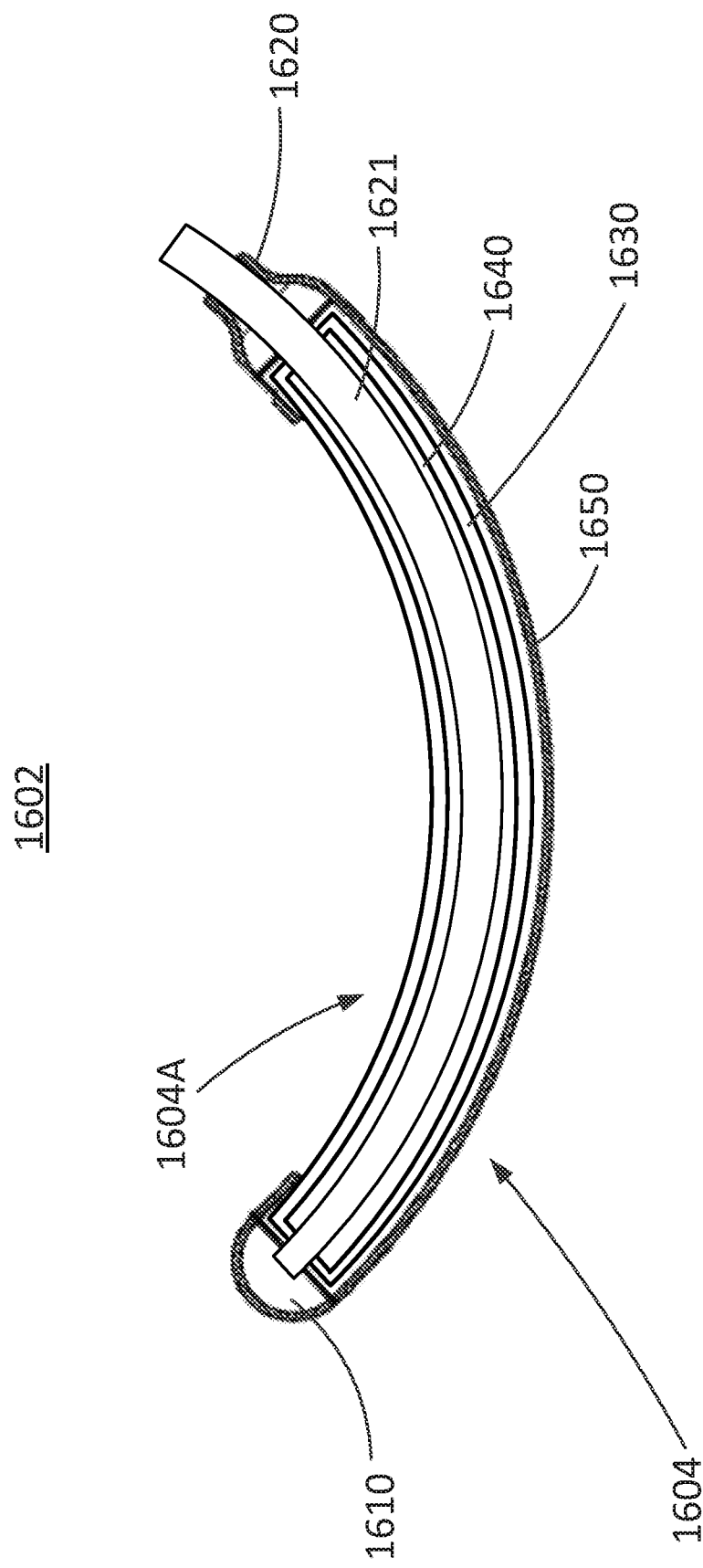
FIG. 32 is a cross-sectional side view of an assembly, according to an embodiment.

FIG. 32 is a cross-sectional illustration of an assembly 1602. The assembly 1602 includes an impermeable casing 1604. The impermeable casing 1604 can be the same or similar in structure and/or function to the impermeable casing 1504 described above with respect to FIGS. 27 and 28. For example, the impermeable casing 1604 can include a reservoir 1610, an impermeable backing 1650, and an outlet 1620. Additionally, the assembly 1602 can include a permeable membrane 1630 and a permeable support 1640. The permeable membrane 1630 and the permeable support 1640 can be the same or similar in structure and function to and of the permeable membranes and permeable supports, respectively, described herein. For example, the permeable membrane 1630 can be a ribbed knit fabric sleeve and the permeable support 1640 can be formed of spun plastic (e.g., non-woven permeable webbing) shaped as a tube. Thus, the assembly 1602 can be pliable and/or flexible such that the assembly 1602 can conform to differently shaped and/or sized users to ensure effective and secure placement of the assembly 1602. The assembly 1602 can include a tube 1621 associated with the outlet 1620 such that fluid in the reservoir 1610 can be removed through the tube 1621 and out of the outlet 1620 via, for example, a vacuum source (not shown).

Figure 33:
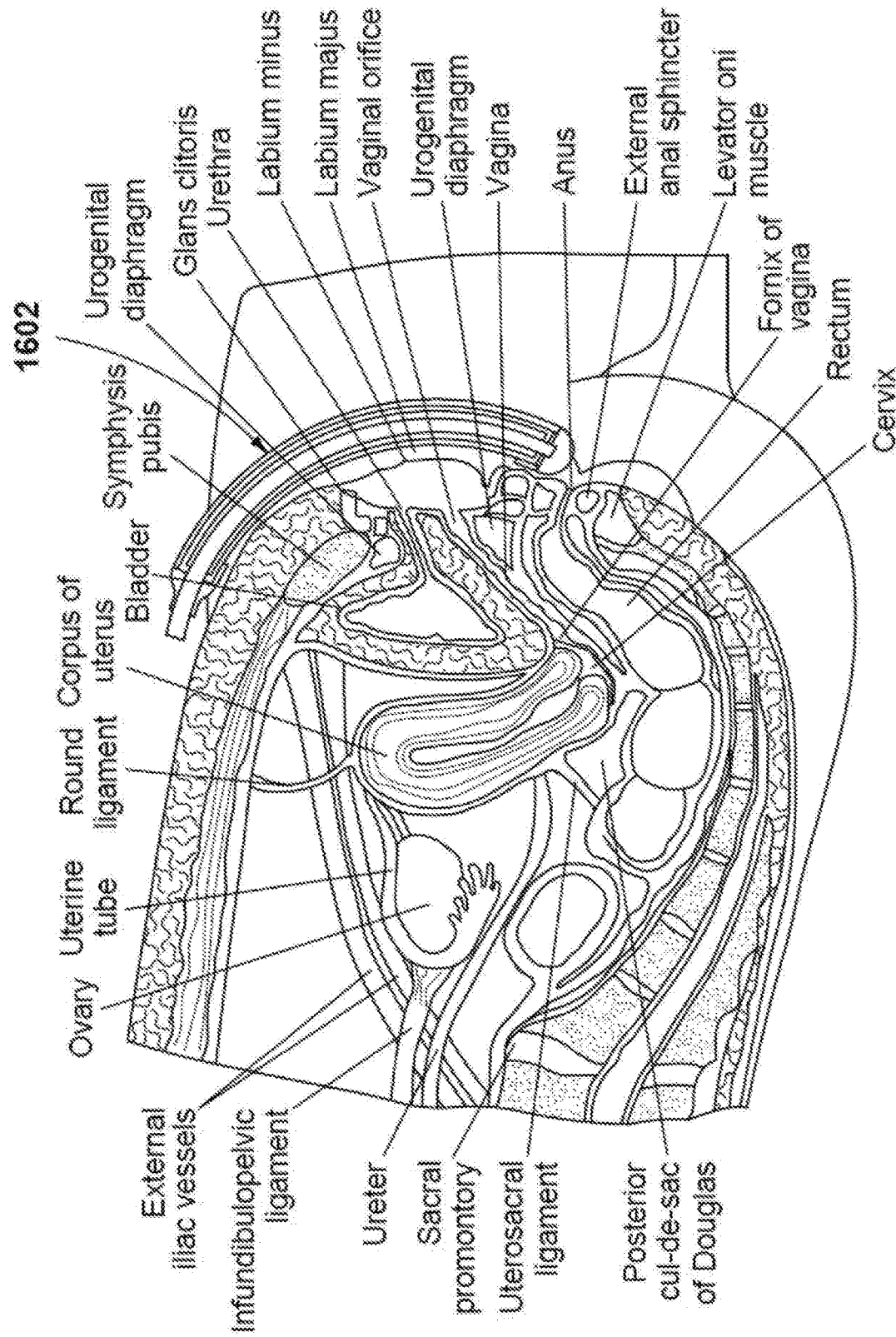
FIG. 33 is a cross-sectional side view of the assembly of FIG. 32 engaged with a female body.

FIG. 33 is a cross-sectional side view of the assembly 1602 engaged with a female body. As shown in FIG. 33, the assembly 1602 can be arranged near the urethra such that the elongated opening 1604A of the assembly 1602 is facing the urethral opening. Additionally, the assembly 1602 can be placed between the labia of the user and held snugly against or near the urethra by the pressure of friction from the user's body. Additionally, as shown in FIG. 33, the assembly 1602 can be curved such that the assembly 1602 provides a comfortable and secure interface for engagement with a user's urethral opening and the surrounding area of the user's body, with the elongated opening on the inside of the curve. Thus, upon the voiding of urine from the user's body, the urine can flow into the assembly 1602 via the elongated opening 1604A, the permeable membrane 1630, and an inlet of the permeable support 1640. The urine can then flow to the reservoir 1610 of the assembly 1602 due to gravity and/or suction provided by a vacuum source via the tube 1621. The suction provided by the vacuum source can then draw the urine from the reservoir 1610, through the tube 1621, and out of the assembly 1602.

The assembly 1602 can have any suitable dimension such that the assembly 1602 can be configured to engage with the urethral opening and/or the area surrounding the urethral opening of users of different sizes and/or anatomical structures. For example, in some embodiments, the impermeable casing 1604 can range from about 7 inches to about 8 inches in length (i.e. from a tip of the reservoir 1610 to the opening in the outlet 1620). In some embodiments, such as for larger patients, the impermeable casing 1604 can range from about 9 inches to about 10 inches in length. In some embodiments, such as for smaller adult patients or children, the impermeable casing 1604 can range from about 3 inches to about 5 inches in length. In some embodiments, the impermeable casing 1604 can range from about 3 inches to about 10 inches in length. The elongated opening 1604A can range from about 5 inches to about 6 inches in length. In some embodiments, the diameter of the impermeable casing 1604 can be about 1 inch. In some embodiments, the diameter of the impermeable casing 1604 can range from about 0.5 inches to about 1.5 inches in diameter. The elongated opening 1604A can have a width of about 1 inch and a depth of about 0.5 inches relative to the height (i.e. diameter) of the impermeable casing 1604. The permeable support 1640 can have a diameter of about 0.875 inches. The outlet 1620 can be about 0.25 inches long and about 0.5 inches wide. The opening of the outlet 1620 can have a diameter of about 0.375 inches. Additionally, the tube 1621 can have a diameter of about 0.375 inches.

Additionally, the assembly 1602 can include any suitable curve such that the assembly 1602 can engage with a user's urethral opening and/or area surrounding the urethral opening. For example, in some embodiments, the assembly 1602 and/or the impermeable casing 1604 can have an angle of curvature of about 40°. In some embodiments, the assembly 1602 and/or the impermeable casing 1604 can have an angle of curvature of about 60°. In some embodiments, the assembly 1602 and/or the impermeable casing 1604 can have a radius of curvature ranging from about 6 inches to about 10 inches.

In some embodiments, the permeable membrane 1630 and/or the permeable support 1640 can be disposed fully within the impermeable casing 1604 such that the permeable membrane 1630 and/or the permeable support 1640 does not extend through the elongated opening 1604A. In some embodiments, the permeable membrane 1630 and/or the permeable support 1640 can be disposed within the impermeable casing 1604 such that a portion of the permeable membrane 1630 and/or a portion of the permeable support 1640 extends through the elongated opening 1604A.

Figure 34:
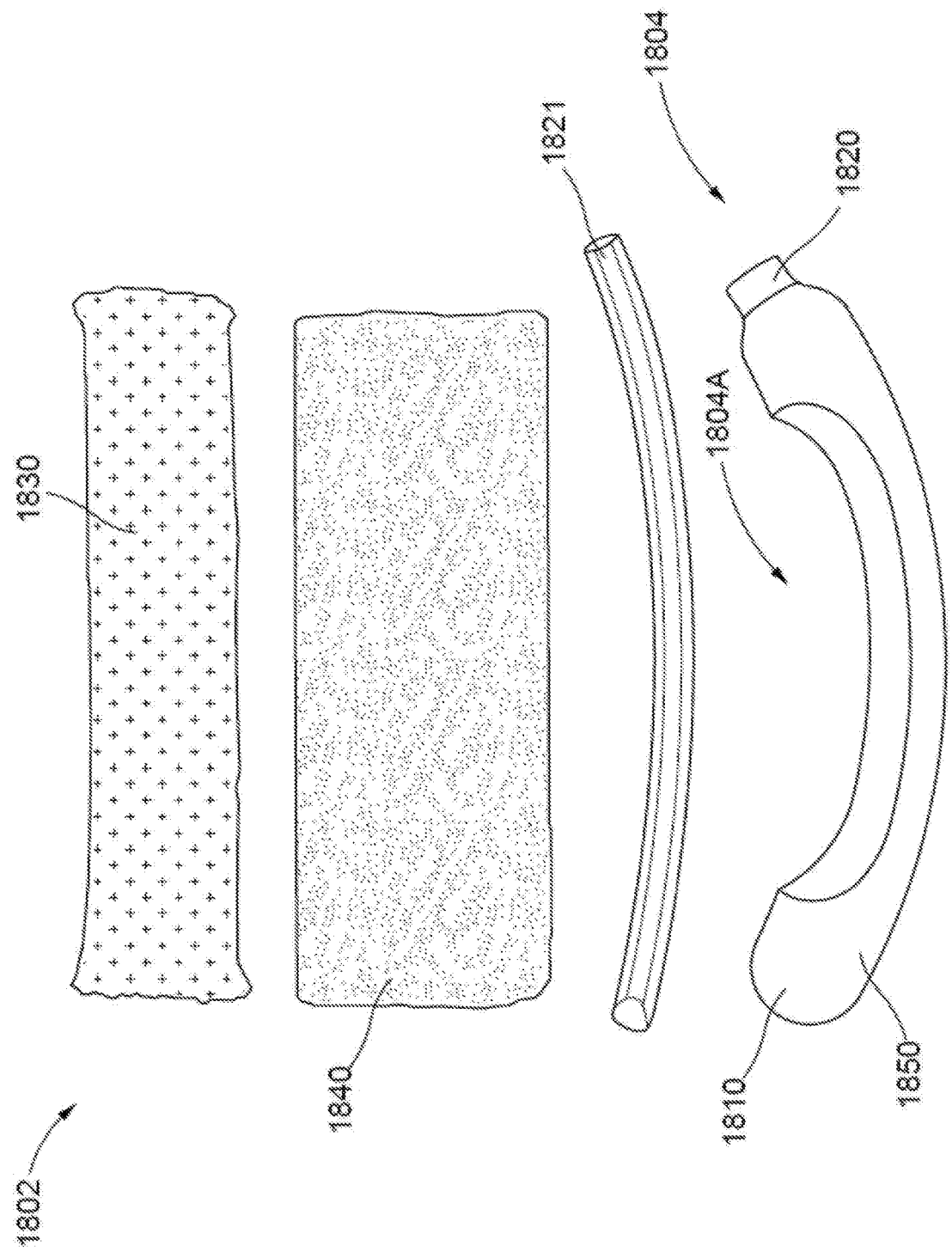
FIG. 34 is an exploded view of an assembly, according to an embodiment.

FIG. 34 is an exploded view of the components of an assembly 1802. The assembly 1802 can be the same or similar in structure and/or function to the assembly 1602 described above. For example, the assembly 1802 includes an impermeable casing 1804. The impermeable casing 1804 can be the same or similar in structure and/or function to the impermeable casing 1604 and/or the impermeable casing 1504. The impermeable casing 1804 can include a reservoir 1810, an impermeable backing 1850, and an outlet 1820. Additionally, the assembly 1802 can include a permeable membrane 1830 and a permeable support 1840. The permeable membrane 1830 and the permeable support 1840 can be the same or similar in structure and function to and of the permeable membranes and permeable supports, respectively, described herein. For example, the permeable membrane 1830 can be a ribbed knit fabric sleeve and the permeable support 1840 can be formed of a flexible sheet of spun plastic (e.g., non-woven permeable webbing) that can be folded or rolled such that the permeable support 1840 is shaped as a tube. Thus, the assembly 1802 can be pliable and/or flexible such that the assembly 1802 can conform to differently shaped and/or sized users to ensure effective and secure placement of the assembly 1802. The assembly 1802 can include a tube 1821 associated with the outlet 1820 such that fluid in the reservoir 1810 can be removed through the tube 1821 and out of the outlet 1820 via, for example, a vacuum source (not shown).

Figure 35:
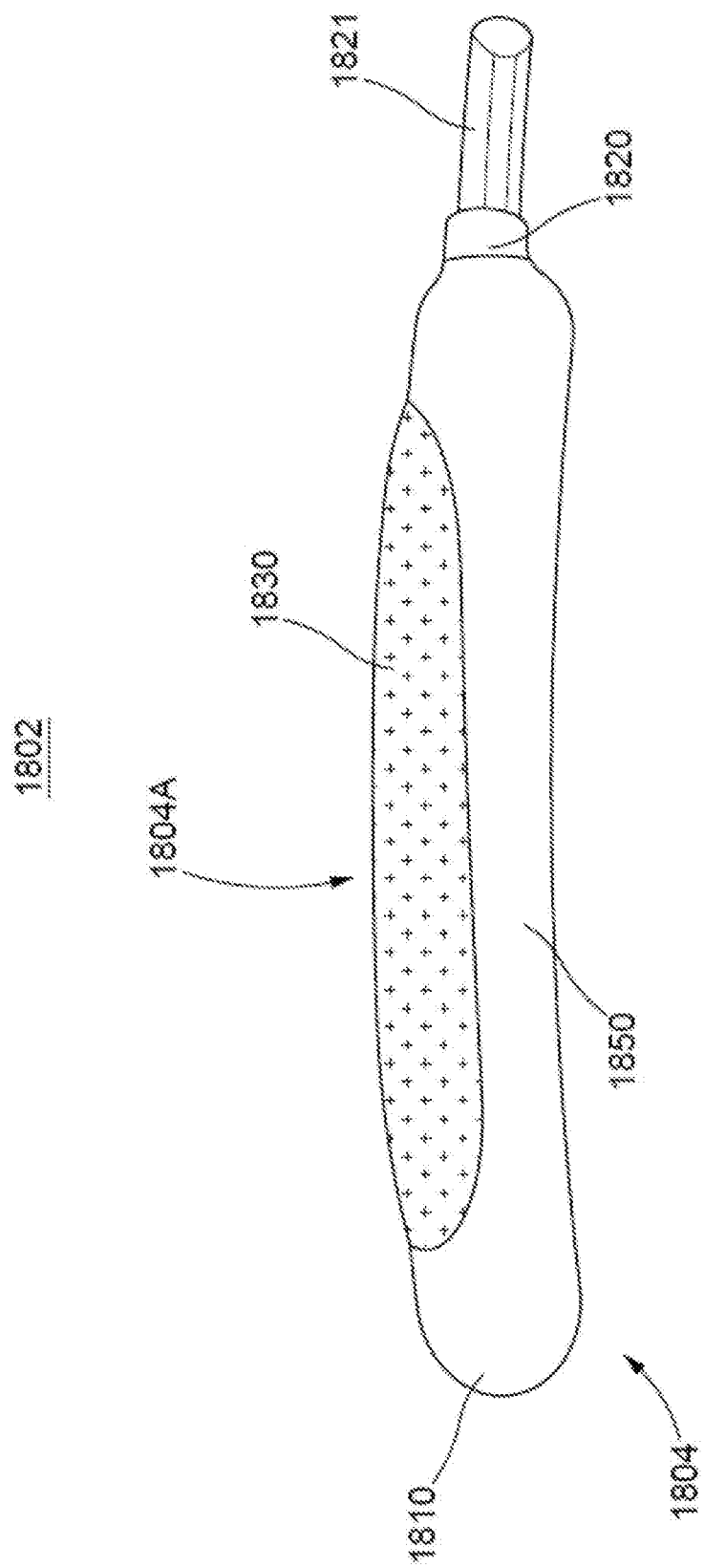
FIG. 35 is a side view of the assembly of FIG. 34 in an assembled configuration.

As shown in FIG. 35, which is a side view of the assembly 1802 in an assembly configuration, the permeable support 1840 can be folded or rolled such that its shape is changed from a sheet to a tube. The permeable membrane 1830 can be pulled over the permeable support 1840. The combination of the permeable membrane 1830 and the permeable support 1840 can then be inserted through the elongated opening 1804A of the impermeable casing 1804 and the impermeable casing 1804 can be stretched and/or otherwise maneuvered such that the impermeable casing 1804 surrounds the permeable membrane 1830 except in the area of the elongated opening 1804A. The tubing 1821 can be inserted through the outlet 1820 such that it is disposed within a channel defined by the permeable support 1840 with one end in the reservoir 1810. In some implementations, the tubing 1821 can be inserted into a channel defined by the permeable support 1840 prior to inserting the permeable support 1840 and the permeable membrane 1830 through the elongated opening 1804A. The tubing 1821 can be threaded through the elongated opening 1804A and through the opening 1820, and the reservoir 1810 of the impermeable backing 1804 can be pulled around the opposite end of the tubing 1821, the permeable support 1840, and the permeable membrane 1830.

Figure 40:
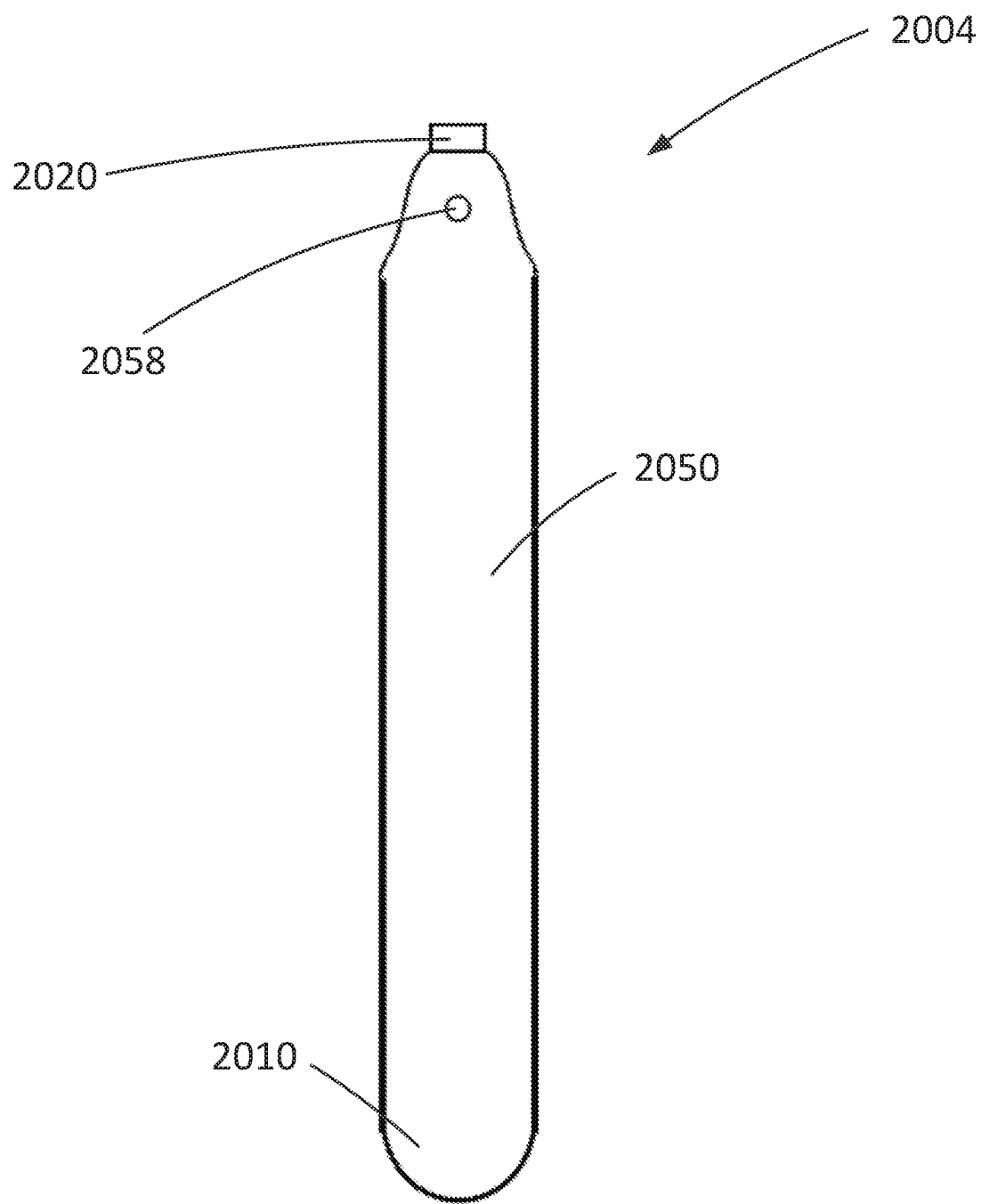
FIG. 40 is a back view of an impermeable casing including a vacuum relief opening, according to an embodiment.

In some implementations, an impermeable layer can define one or more vacuum relief openings. For example, FIG. 40 is a back view of an impermeable casing 2004. The impermeable casing 2004 can be the same or similar to the impermeable casing 1804 shown in and described with reference to FIGS. 34 and 35. The impermeable casing 2004 can include a reservoir 2010, an impermeable backing 2050, and an outlet 2020. The impermeable casing can also include a vacuum relief opening 2058. Thus, in the event that a user's body envelopes an assembly including the impermeable layer 2050, such as an assembly the same or similar to assembly 1802, the one or more vacuum relief openings 2058 can prevent suction from increasing against the skin of the user, which may be uncomfortable or painful. For example, the impermeable casing 2004 can define an elongated opening (not shown) the same or similar to the elongated opening 1804A described above. The vacuum relief opening 2058 can be located between two ends of the impermeable casing 2004 such that at least one additional airflow path exists in the assembly in the event that the user's body obstructs a portion of or the entire elongated opening. Although shown as being located near the outlet 2020, the vacuum relief opening 2058 can be disposed at any suitable location on the impermeable layer 2050. In some implementations, the one or more vacuum relief openings 2058 can be disposed in a location that reduces the likelihood that the skin of the labia or the thigh of the user inadvertently covers the hole, such as a location near the outlet 2020. Additionally, the impermeable casing 2004 can include any suitable number of vacuum relief openings 2058.

Figure 36:
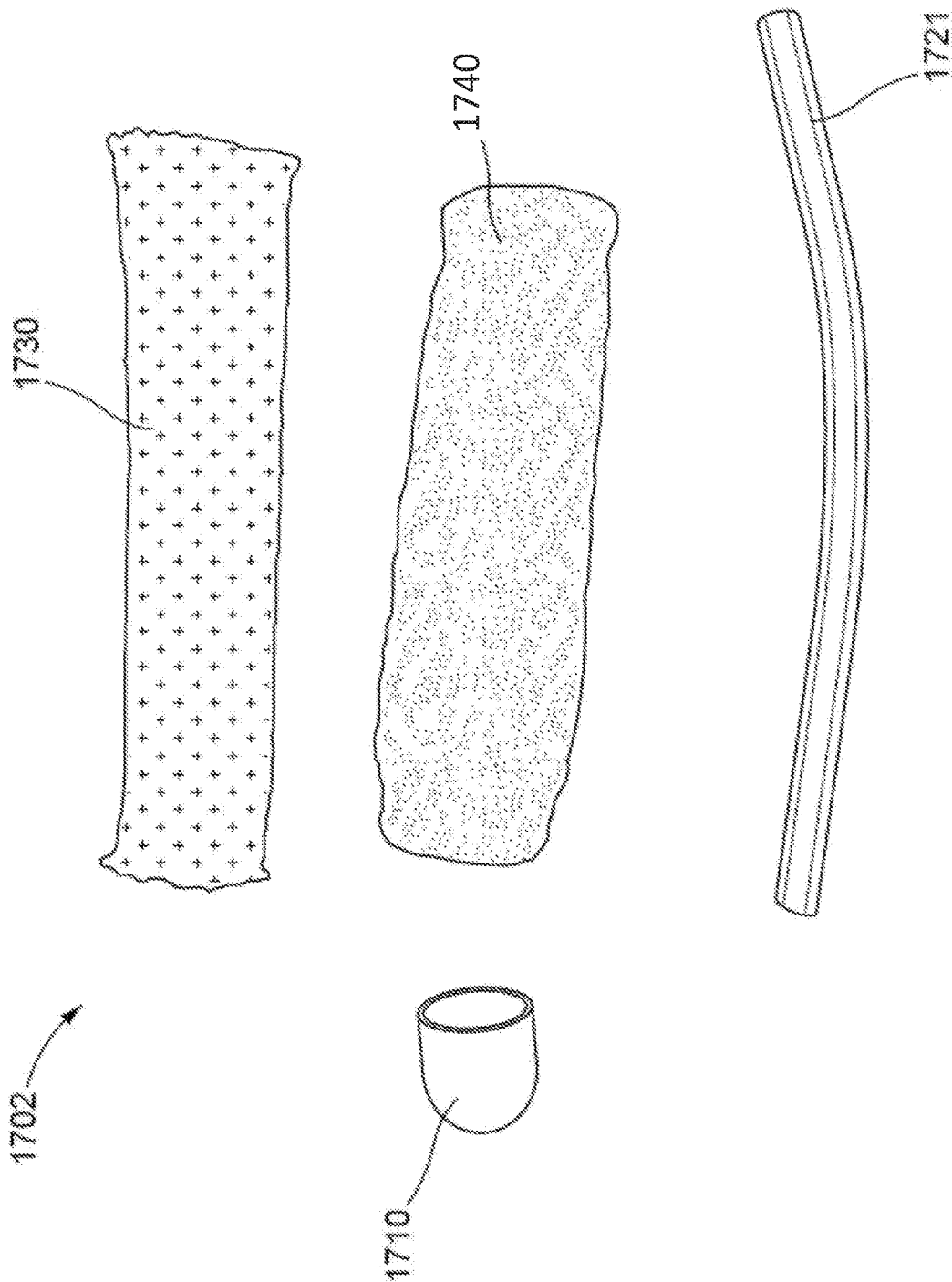
FIG. 36 is an exploded view of a portion of an assembly, according to an embodiment.

In some implementations, rather than including an impermeable casing, an assembly can include an impermeable backing that includes adhesive tape. For example, FIG. 36 is an exploded view of an assembly 1702. The assembly 1702 includes a reservoir 1710, a permeable support 1740, a permeable membrane 1730, and a tube 1721. The assembly 1702 can be similar in structure and/or function to the assembly 1602 described above with reference to FIGS. 32 and 33. For example, the permeable membrane 1730 and the permeable support 1740 can be the same or similar to any of the permeable membranes and permeable supports described herein. For example, the permeable support 1740 can be a flexible sheet of spun plastic (e.g., non-woven permeable webbing). Thus, the assembly 1702 can be pliable and/or flexible such that the assembly 1702 can conform to differently shaped and/or sized users to ensure effective and secure placement of the assembly 1702. In some implementations, the permeable membrane 1730 can be a ribbed knit fabric sleeve. Additionally, the tube 1721 can be associated with an outlet (e.g., the outlet 1720 in FIG. 38) for drawing fluid out of the reservoir 1710 and into an external receptacle (such as external receptacle 160 shown and described with respect to FIG. 1). The reservoir 1710 can include a flexible cap and can be configured to be attached to the permeable membrane 1730 and/or the permeable support via an impermeable backing (e.g., the impermeable backing 1750 in FIG. 28).

Figure 37:
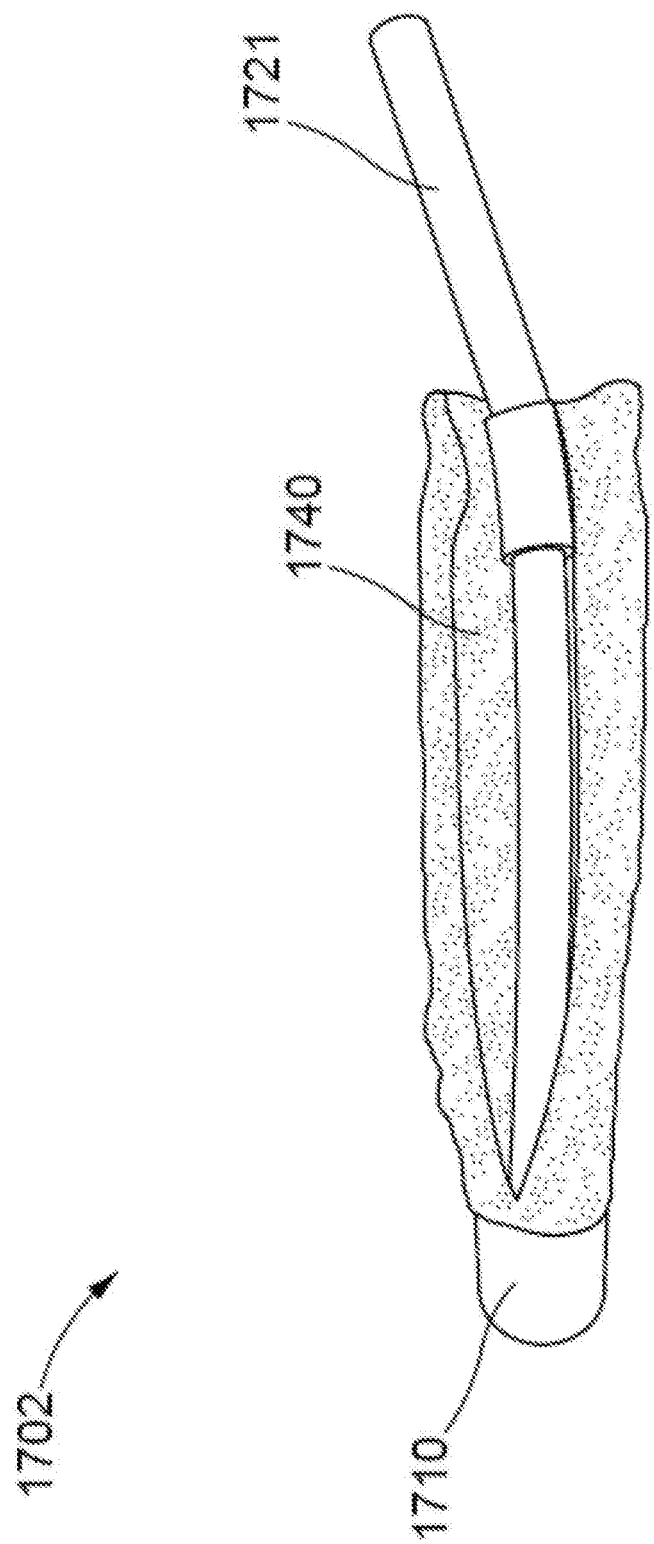
FIG. 37 is a top view of a partially assembled configuration of the assembly of FIG. 36.

As shown in FIG. 37, which is a side view of a partially assembled assembly 1702, the permeable support 1840 can be folded or rolled such that its shape is changed from a sheet to a tube. The permeable support 1840 can then be inserted into the reservoir 1710 (e.g., a flexible cap). The tube 1721 can be inserted through a channel formed by the permeable support 1840 and into the reservoir 1710.

Figure 38:
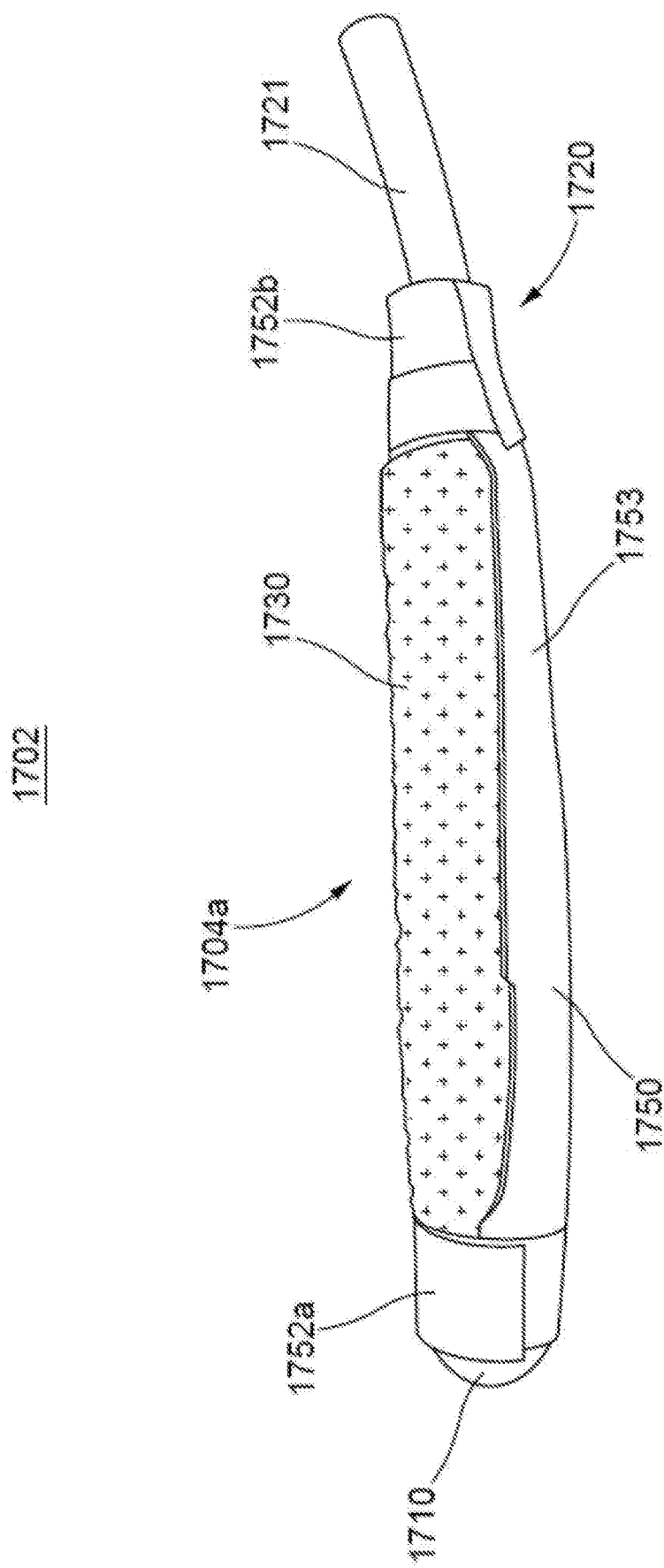
FIG. 38 is a side view of the assembly of FIG. 36 in an assembled configuration.

As shown in FIG. 38, the assembly 1702 can include an impermeable backing 1750 that includes adhesive tape. The impermeable backing 1750 can include two securing portions 1752A and 1752B connected by a backing portion 1753. The securing portions 1752A and 1752B in combination with the backing portion 1753 can define an elongated opening 1704A through which a fluid (e.g., urine) can travel into the assembly 1702. Additionally, the securing portion 1752A can be used to secure the reservoir 1710 to the backing portion 1753, the permeable membrane 1730, and/or the permeable support 1740 (shown in FIGS. 36 and 37). In some implementations, the securing portion 1752B in combination with the tube 1721 can form a portion of or all of the outlet 1720. Thus, the impermeable backing 1750 can direct fluid flow through the assembly 1702 such that fluid that enters the permeable membrane 1730 and the permeable support 1740 via the elongated opening 1704A does not exit the assembly 1702 except via the tube 1721. In use, the fluid can flow due to gravity and/or suction toward the reservoir 1710 and be contained by the reservoir 1710 and the impermeable backing 1750. The tube 1721 can then be used to draw the fluid out of the assembly 1702 (via, for example, a vacuum source). Additionally, the impermeable backing 1750 can assist in limiting the area of the permeable membrane 1730 experiencing suction from a vacuum source such that the pressure differential is stronger and fluid can be drawn through the permeable membrane 1730 efficiently.

FIG. 39 is a flowchart illustrating a method of using an assembly to collect urine from a user, according to an embodiment. The method 1900 optionally includes, at 1902, fluidically coupling the discharge end of the tube of the urine collecting apparatus to a fluid receptacle. Method 1900 optionally further includes, at 1904, fluidically coupling the discharge end of the tube of the urine collecting apparatus to a source of vacuum. Method 1900 further includes, at 1906, disposing in operative relationship with the urethral opening of a female user (e.g. human or animal) the urine collecting apparatus. The urine collecting apparatus can be the same or similar in structure and/or function to any of the urine collecting apparatus described herein, such as, for example, the assembly 102 in FIG. 1. For example, the urine collecting apparatus can include a fluid impermeable casing, a fluid permeable support, a fluid permeable membrane, and a tube. The fluid impermeable casing can have a fluid reservoir at a first end and a fluid outlet at a second end. A longitudinally extending fluid impermeable layer can be coupled to the fluid reservoir and the fluid outlet and can define a longitudinally elongated opening between the fluid reservoir and the fluid outlet. The fluid permeable support can be disposed within the casing with a portion extending across the elongated opening. The fluid permeable membrane can be disposed on the support and can cover at least the portion of the support that extends across the elongated opening, so that the membrane is supported on the support and disposed across the elongated opening. The tube can have a first end disposed in the reservoir and a second fluid discharge end. The tube can extend behind at least the portion of the support and the portion of the membrane disposed across the elongated opening and can extend through the fluid outlet to the second fluid discharge end. The operative relationship can include the opening being adjacent to the urethral opening of the female user.

The method 1900 also includes, at 1908, allowing urine discharged from the urethral opening to be received through the opening of the fluid impermeable layer, the membrane, the support, and into the reservoir.

The method 1900 also includes, at 1910, allowing the received urine to be withdrawn from the reservoir via the tube and out of the fluid discharge end of the tube.

The method 1900 optionally includes, at 1912, removing the urine collecting apparatus from the operative relationship with the urethral opening of the user.

Finally, the method 1900 optionally includes, at 1914, disposing a second urine collecting apparatus in operative relationship with the urethral opening of the user.

In some embodiments, the support and casing can be cylindrical and can have a curved shape with the elongated opening disposed on the inside of the curve. The disposing can include disposing the urine collecting apparatus with the elongated opening adjacent the urethral opening of the user and oriented with the reservoir proximal to the user's anus and the outlet disposed above the urethral opening.

Figure 41:
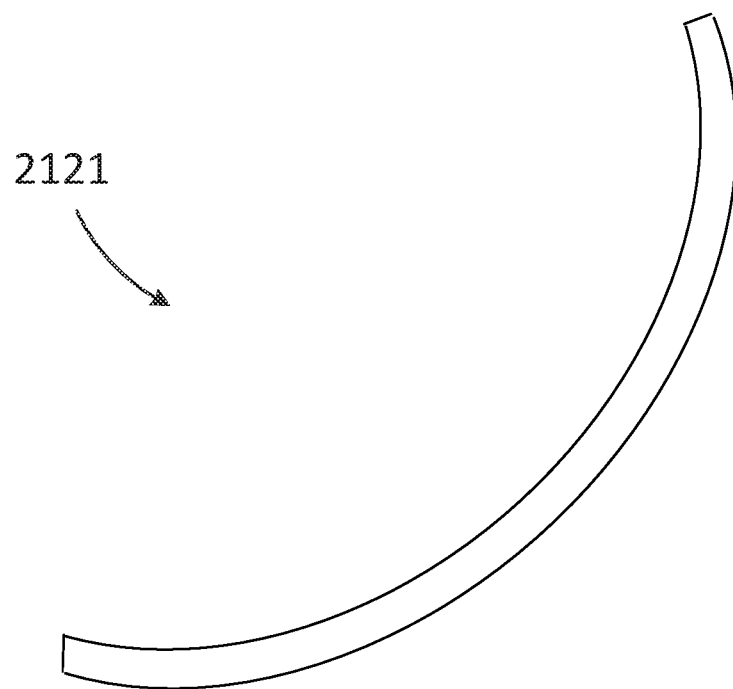
FIG. 41 is a schematic illustration of a tube with a precurved shape, according to an embodiment.

In some embodiments, an assembly (such as, for example, the assembly 1602 shown in FIG. 32) can have a curved shape that is defined or maintained at least in part by a shape-retaining member. In some embodiments, the shape-retaining member can be implemented as a tube with an intake end positioned within a reservoir such that the tube extends from the reservoir and through at least a portion of a permeable support, similar to, for example, the tube 1621 shown with respect to FIGS. 32 and 33, that has a precurved shape such that at least a portion of an assembly including the tube will also have a similar or corresponding precurved shape. For example, as shown in FIG. 41, a tube 2121 is precurved. The tube 2121 can be the same or similar in structure and/or function to any of the tubes described herein, such as the tube 1621, the tube 1721, and/or the tube 1821. The tube 2121 can be precurved to any suitable curved shape (e.g., any suitable angle of curvature) such that, for example, an assembly including the tube 2121 can engage with a user's urethral opening and/or an area surrounding the urethral opening.

In some implementations, the tube 2121 can be initially formed such that it has an uncurved (i.e., straight) overall shape. The tube 2121 can then be curved via, for example, heat setting. Said another way, the tube 2121 can be formed of a stiff or rigid material, such as a stiff plastic, in a straight shape. The tube 2121 can be heated such that the tube 2121 is softened, and then the tube 2121 can be bent to a predefined curved shape. After being curved, the tube 2121 can be cooled such that the tube 2121 hardens.

In some implementations, the tube 2121 can be precurved by initially forming the tube 2121 such that the tube 2121 has a straight shape and then bending the tube 2121 beyond the elastic limit of the tube 2121 such that the tube 2121 has a preset curve. For example, the tube 2121 can be formed of a material such as metal that will retain a curved shape after being bent to the curved shape.

Figure 42:
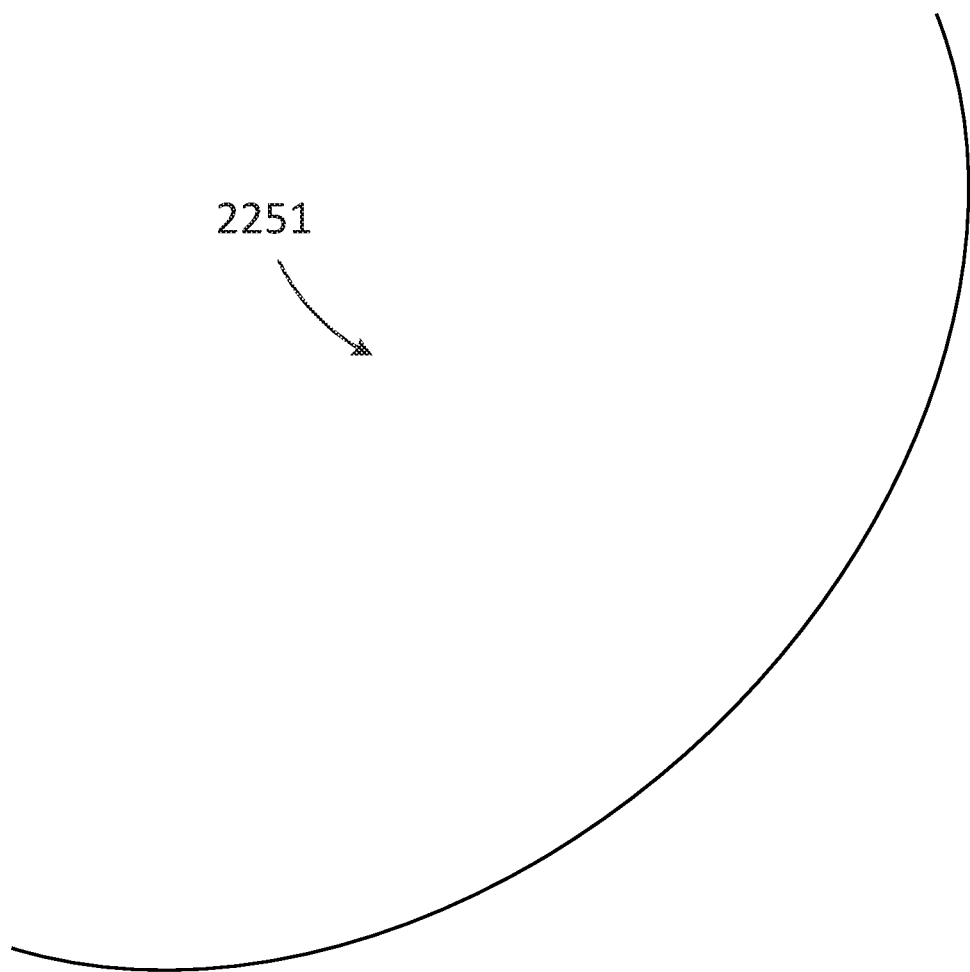
FIG. 42 is a schematic illustration of a shape-retaining element, according to an embodiment.

In some embodiments, an assembly (such as, for example, the assembly 1602 shown in FIG. 32) can have a curved shape that is defined or maintained at least in part by a shape-retaining member that is separate from the tube that has an intake end in the reservoir. Thus, the assembly can have both a tube and a separate shape-retaining element for maintaining the assembly or a portion of the assembly in a precurved shape. For example, as shown in FIG. 42, a shape-retaining element 2251 can have a precurved shape. The shape-retaining element 2251 can be formed of, for example, a strip of semi-rigid material. The shape-retaining element 2251 can be attached to any suitable portion of the assembly. For example, in some implementations, the shape-retaining element 2251 can be attached to an inner surface of an impermeable layer, such as impermeable layer 1650. In some implementations, the shape-retaining element 2251 can be disposed between an impermeable layer (e.g., the impermeable layer 1650) and a permeable support (e.g., the permeable support 1640) and/or a permeable membrane (e.g., the permeable membrane 1630). In some implementations, the shape-retaining element 2251 can be attached to an outer surface of an impermeable layer (e.g., the impermeable layer 1650) or can be imbedded in an impermeable layer (e.g., the impermeable layer 1650).

Figure 43:
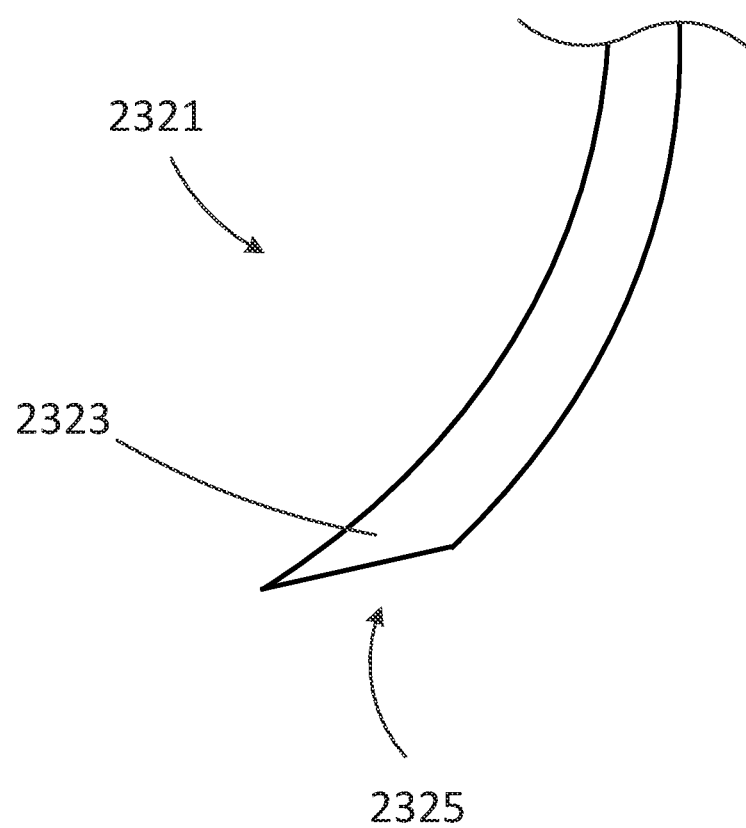
FIG. 43 is a schematic illustration of a tube with a beveled intake end, according to an embodiment.

In some embodiments, a tube with an intake end positioned within a reservoir such that the tube extends from the reservoir and through at least a portion of a permeable support, similar to, for example, the tube 1621 shown with respect to FIGS. 32 and 33, can have a beveled intake end (i.e. a beveled reservoir end). As shown in FIG. 43, a tube 2321 includes a beveled intake end 2323. The tube 2321 can be the similar in structure and/or function to any of the tubes described herein, such as, for example, the tube 1621, the tube 1721, the tube 1821 and/or the tube 2121. The beveled intake end 2323 can prevent blockage of the tube 2321 in operation. For example, the beveled intake end 2323 can increase the size of an intake opening 2325 of the tube 2321 such that the intake opening 2325 is less likely to be blocked by an obstruction. Additionally, the beveled intake end 2323 can prevent the tube 2323 from becoming obstructed at the intake end by the material forming the reservoir. For example, in assemblies in which the reservoir is formed by a flexible and/or pliable material as part of a casing, such as the reservoir 1810 of casing 1804 in FIG. 35, the suction resulting from the vacuum through the tube 1821 and/or force applied to the outside of the reservoir may cause the material of the reservoir 1810 to move toward the intake end of the tube 1821 and obstruct and/or seal the intake end of the tube 1821, preventing the flow of fluid through the intake end of the tube 1821. A beveled intake end of the tube 2321 can prevent this obstruction from occurring due to the angled tip. Even if a portion of a reservoir (e.g., 1810) flexes into contact with the distal end of the tube 2321, the intake opening 2325 can remain at least partially or completely unobstructed.

Figure 44A:
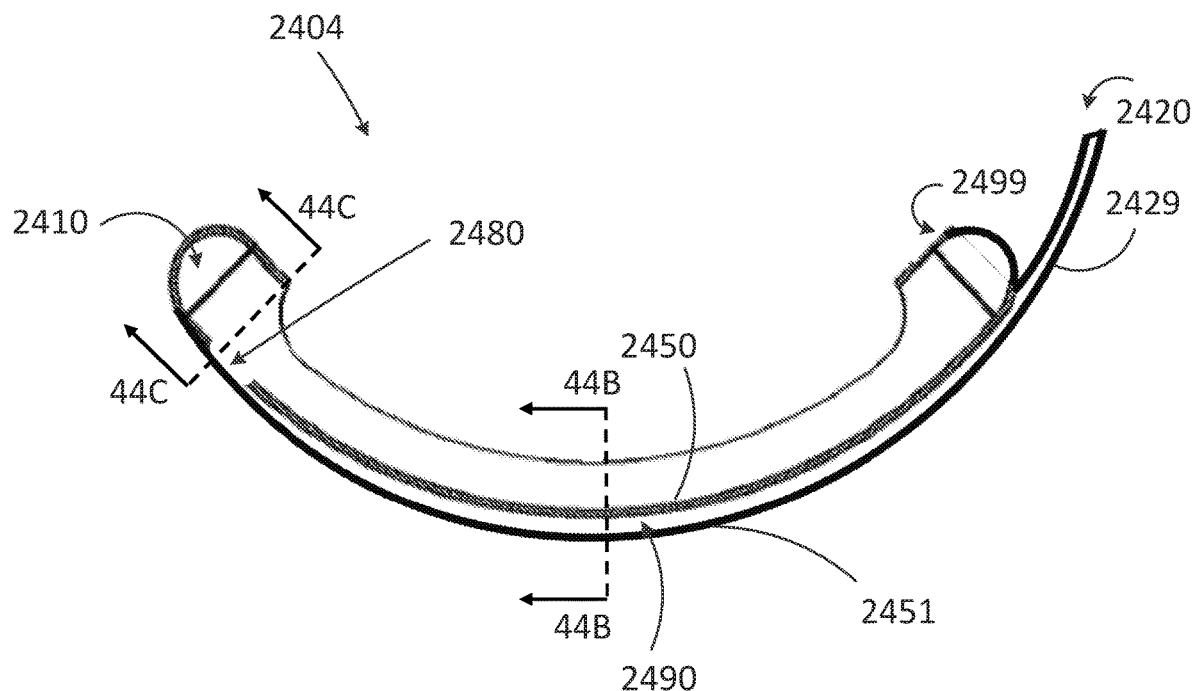
FIG. 44A is a schematic illustration of an impermeable casing with a precurved shape including a channel and an opening to remove urine collected from a user, according to an embodiment.
Figure 44B:
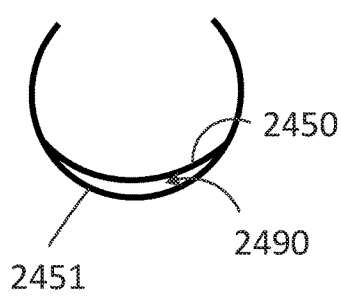
FIG. 44B is a schematic illustration of a cross-sectional view of the casing in FIG. 44A, taken along the line 44B-44B.
Figure 44C:
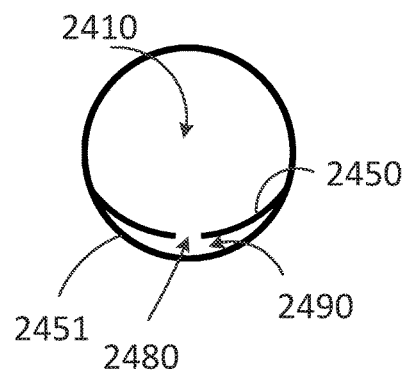
FIG. 44C is a schematic illustration of a cross-sectional view of the casing in FIG. 44A, taken along the line 44C-44C.
Figure 44D:
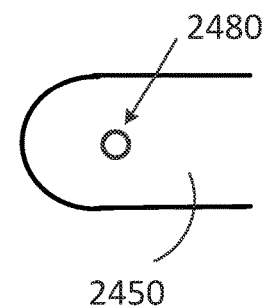
FIG. 44D is a schematic illustration of a cross-sectional bottom view of the impermeable backing in the casing shown in FIG. 44A showing an opening from a reservoir.

In some embodiments, an assembly can include a casing that includes a channel defined in a sidewall of the casing, instead of the tube extending within the casing, as disclosed in many of the previous embodiments. For example, FIG. 44A is a cross-sectional side view of a casing 2404. The casing 2404 can be similar in structure and/or function to any of the casings described herein, such as, for example, the casing 1604 shown in FIG. 32. For example, casing 2404 can include a reservoir 2410 and an impermeable backing 2450. The casing 2404 can include a closed end 2499 opposite the reservoir 2410. In some embodiments, as shown in FIG. 44A, the casing 2404 can include an impermeable external wall 2451, such that the impermeable backing 2450 and the external wall 2451 collectively define a channel 2490. For example, FIG. 44B, which is a schematic illustration of a cross-section of the casing 2404 taken along the line 44B-44B in FIG. 44A, shows the channel 2490 defined between the external wall 2451 and the impermeable backing 2450. The impermeable backing 2450 can define an opening 2480 such that the channel 2490 can be in fluidic communication with the reservoir 2410 via the opening 2480. For example, FIG. 44C, which is a schematic illustration of a cross-section of the casing 2404 taken along the line 44C-44C in FIG. 44A, shows the opening 2480 defined in the impermeable backing 2450 such that fluid can flow from the reservoir 2410, through the opening 2480, and into the channel 2490. Although FIGS. 44A-44D show the opening 2480 disposed at the point of line 44C-44C (i.e., near or in the reservoir 2410), in some embodiments one or more openings similar in structure and/or function to opening 2480 can be disposed at one or more other positions along the impermeable backing 2450 that are suitable for forming a fluidic connection between the channel 2490 and the reservoir 2410. FIG. 44D, which is a schematic illustration of a bottom view of the impermeable backing 2450 (i.e., without the external wall 2451 attached), similarly shows the opening 2480 defined in the impermeable backing 2450 near the reservoir 2410.

The channel 2490 can extend along the length of the casing 2404, as shown, from the opening 2480 to an outlet 2420 such that fluid in the reservoir 2410 can be removed via the opening 2480 through the channel 2490 via, for example, a vacuum source (not shown) coupled to the outlet 2420. Although shown as having a crescent shape, the channel 2490 can be formed in any suitable shape. For example, the channel 2490 can be tubular. In some implementations, as shown in FIG. 44A, a tube 2429 can be coupled to or integrally formed with the casing 2404 such that the tube 2429 defines an additional length of the channel 2490 and thus the outlet 2420 is disposed at a distance from the impermeable backing 2450. In some implementations, the outlet 2420 may be disposed proximal to the closed end 2499 of the casing. In some implementations, the tube 2429 and the other components of the casing 2404 can be formed as an integral, one-piece structure, as shown in FIG. 44A. In some implementations, the external wall 2451 at least partially defining the channel 2490 and/or the tube 2429 can be separately formed and attached to the impermeable backing 2450 and/or the closed end of the casing 2499 via, for example, adhesive or tape.

The casing 2404 can be made from material similar in structure and/or function to any of the casings described herein, such as, for example, the casing 1504 shown in FIG. 27, the casing 1604 in FIG. 32 and/or the casing 1804 shown in FIG. 35, such that the assembly can withstand the pressure differential needed to draw fluid voided from the urethral opening of a user into a permeable support (not shown) housed within the casing 2404 and into the reservoir 2410 without collapsing. The casing 2404, the channel 2490 and/or the tube 2429 may include spines or other suitable structures to reinforce their structural integrity. The casing 2404, and in particular the impermeable backing 2450 and the external wall 2451 defining the channel 2470, can be made of a material and formed so as to be able to withstand the pressure differential needed to remove collected fluid from the reservoir 2410 through the channel 2490 via the opening 2480, through the outlet 2420, and into an external receptacle (not shown). Thus, the impermeable backing 2450 and the external wall 2451 can be made of a material sufficiently strong or rigid such that the channel 2490 can remain open and unobstructed when coupled to a vacuum source.

Figure 45:
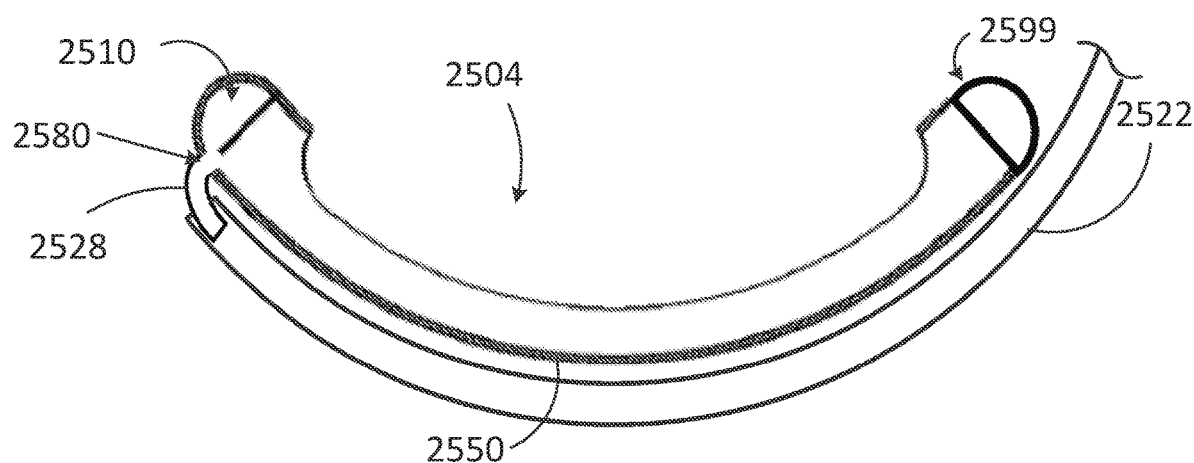
FIG. 45 is a schematic illustration of a casing with a tube and an opening from the reservoir of an assembly, according to an embodiment.

In some embodiments, rather than the channel being collectively defined by an external wall and an impermeable backing, the assembly can include an external tube defining a channel. For example, FIG. 45 is a cross-sectional illustration of an assembly 2500. The assembly 2500 can include a casing 2504. The casing 2504 can be similar in structure and/or function to any of the casings described herein, such as, for example, the casing 2404 shown in FIG. 44A. For example, casing 2504 can include a reservoir 2510 and an impermeable backing 2550. The casing 2504 can include a closed end 2599 opposite the reservoir 2510. The impermeable backing 2550 and/or the reservoir 2510 can define an opening 2580. The assembly 2500 can include an outlet tube 2528 defining a lumen. The outlet tube 2528 can be disposed on the casing 2504 such that the outlet tube 2528 extends from the opening 2580 and the lumen of the outlet tube 2528 is in fluid communication with the opening 2580 and the reservoir 2510. The outlet tube 2528 may be made of flexible or rigid material. The casing 2504 and the outlet tube 2528 can be formed together as an integral piece or formed separately and connected using any suitable coupling mechanism such as, for example, tube fittings, adhesive, and/or tape. Although in the embodiment shown in FIG. 45 the opening 2580 is disposed in the reservoir 2510, in other embodiments one or more openings similar in structure and/or function to the opening 2580 can be disposed at other position(s) along the impermeable backing, and an outlet tube such as the outlet tube 2528 can be coupled to each of the one or more openings.

In some implementations, the assembly 2500 can include an external tube 2522 defining a channel. The outlet tube 2528 can be coupled to the external tube 2522 such that the channel of the external tube 2522 is in fluidic communication with the lumen of the outlet tube 2528 (and, thus, the reservoir 2510). The outlet tube 2528 can have any suitable length for fluidically coupling the reservoir 2510 with the external tube 2522. The outlet tube 2528 can be secured to the external tube 2522 using any suitable coupling mechanism such as, for example, a leak-proof tube connecting apparatus, adhesive, and/or tape. In some implementations, the external tube 2522 can be fluidically coupled to a vacuum source (not shown) such that fluid can be evacuated from the reservoir 2510 via suction created by the vacuum source. The outlet tube 2528 (and the casing 2504 if formed integrally with tube 2528) can be made from material similar in structure and/or function to any of the casings described herein, such as, for example, the casing 2404 shown in FIG. 44A, such that the assembly can withstand the pressure differential needed to draw urine voided from the urethral opening of a user into a permeable support (not shown) housed within the casing 2504, into the reservoir 2510, through the outlet tube 2528 via the opening 2580, and through the external tube 2522 connected to an external receptacle (not shown).

Figure 46:
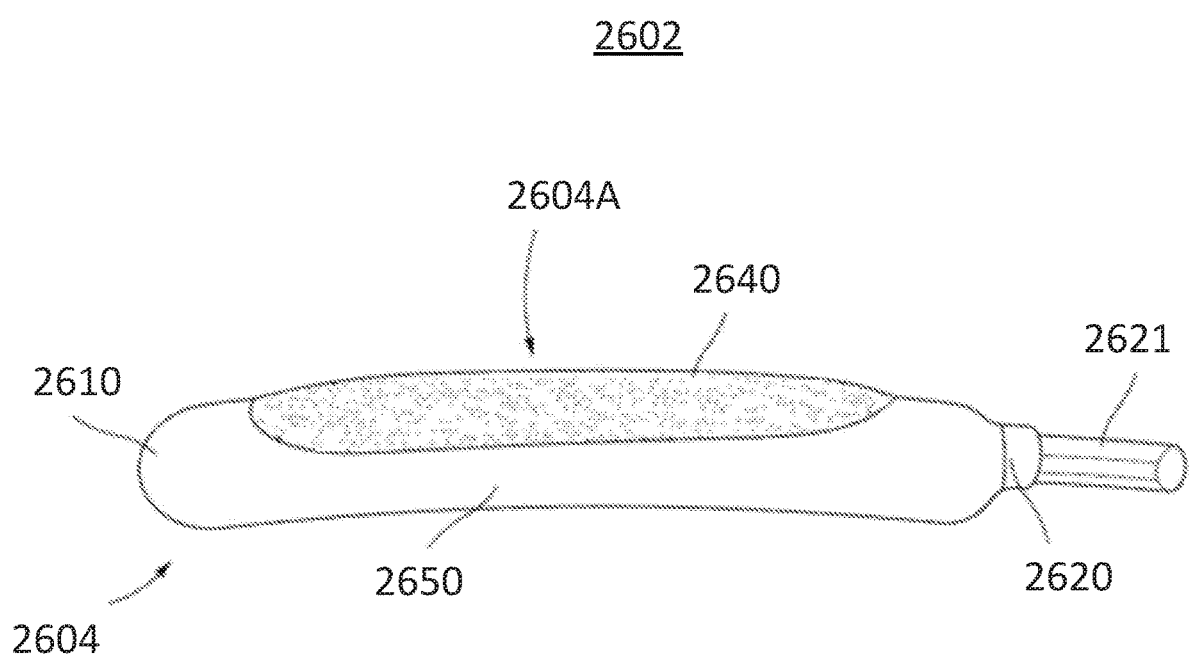
FIGS. 46 and 47 are a schematic side view and exploded view of an assembly with a casing and a porous support material, according to an embodiment.
Figure 47:
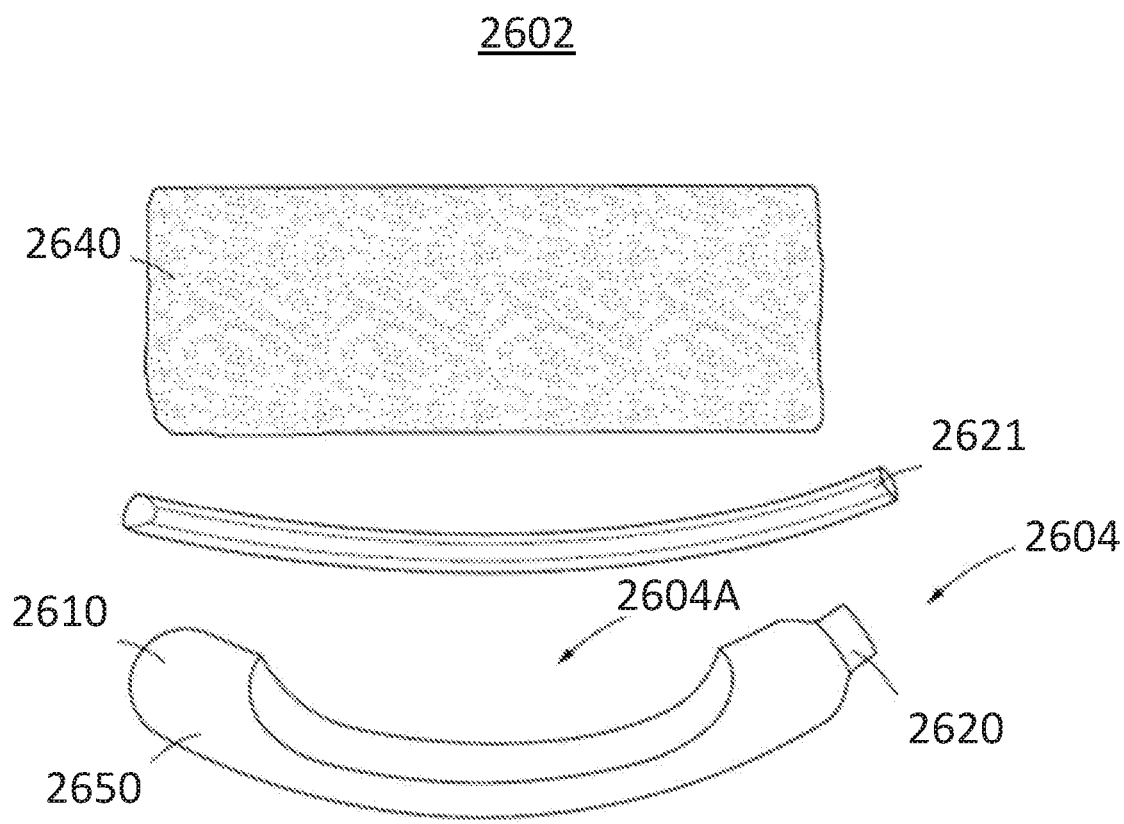

In some embodiments, rather than including a permeable membrane disposed on a permeable support, the permeable support can be formed of a material that provides the functions of both the permeable membrane and the permeable support. For example, FIGS. 46 and 47 are a side view and an exploded view, respectively, of an assembly 2602, according to an embodiment. The assembly 2602 includes a permeable support 2640, a tube 2621, and a casing 2604. The permeable support 2640 can be formed of a material that includes the at least some of the features and/or provides at least some of the functions of both the permeable membrane and permeable support of embodiments described above. The assembly 2602 can otherwise be the same or similar in structure and/or function to the any of the embodiments described above. For example, the impermeable casing 2604 can be the same or similar in structure and/or function to the impermeable casings 1504, 1604, 1804, 2004, 2404, and/or 2504. The impermeable casing 2604 can include a reservoir 2610, an impermeable backing 2650, and an outlet 2620. Additionally, the impermeable casing 2604 can define an elongated opening 2604A.

As noted above, the permeable support 2640 can be the same or similar in function to the permeable membranes and/or the permeable supports, respectively, described in the previous embodiments. The permeable support 2640, however, can be formed of a single material that meets the functional requirements and/or includes the functional benefits of the materials of both the permeable membranes and the permeable supports of the previous embodiments. Specifically, the permeable support 2640 is formed can have sufficient structural integrity to serve as a permeable support for the casing 2604, sufficient porosity and/or permeability to allow urine to pass freely through the permeable support 2640, and/or sufficient loft and resiliency to extend to or out of the elongated opening 2604A. The permeable support 2640 can also be sufficiently pliable and/or flexible such that the assembly 2602 can conform to differently shaped and/or sized users to ensure effective and secure placement of the assembly 2602.

In addition, the material of which the permeable support 2640 is formed can have an exterior surface that provides the same functions as the permeable membranes of the previous embodiments. Thus, the permeable support 2640 can be urine permeable and can have wicking properties. Specifically, the permeable support 2640 can have a high absorptive rate and a high permeation rate such that urine can be rapidly absorbed and/or transported therethrough. The permeable support 2640 can be soft and/or minimally abrasive such that it does not irritate the skin of the user. Additionally, the permeable support 2640 can wick fluid away from the urethral opening and/or the skin of the user such that the dampness of the skin of the user is lessened and infections are prevented. The permeable support 2640 can also be sufficiently permeable and/or have sufficient wicking ability to help prevent urine from leaking or flowing beyond the assembly onto, for example, a bed.

Figure 48:
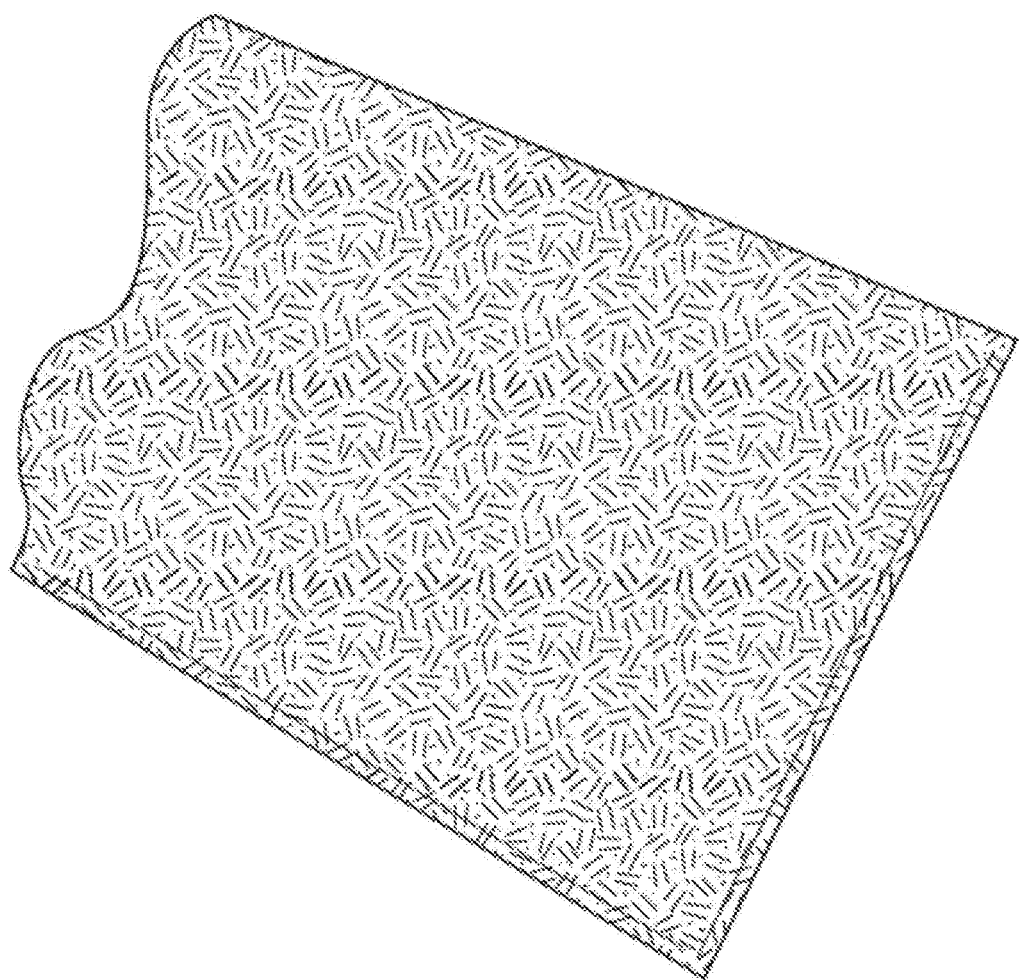
FIG. 48 is an illustration of a top view of a sheet of material used as the permeable support of the embodiment of FIGS. 46 and 47.

The material of which the permeable support 2640 is formed can be in the form of a flexible sheet rolled or folded into a tubular form, for example, as shown in FIG. 47 and in the illustration in FIG. 48. Alternatively, the permeable support 2640 can be formed as a cylinder such that the permeable support 2640 has the desired shape without rolling or folding. The permeable support 2640 can be made from, for example, polyester, recycled polyester fleece, and/or nylon knit mesh. The permeable support 2640 can be secured within a hollow casing (for example, the casing 2604 shown in FIGS. 46 and 47) by inserting the permeable support 2640 into the casing via an elongated opening of the casing (e.g., elongated opening 2604A of the casing 2604). In some implementations, the permeable support 2640 may be affixed to a casing such as the casing 2604 by using any suitable means, such as, for example, using adhesive, glue, and/or tape.

In use, once inserted and positioned against the impermeable backing 2650, the assembly 2602 may be positioned relative to a user such that the surface of the permeable support 2640 contacts the urethral opening of the user. Urine can be drawn through the permeable support 2640 such that the urine collects in the reservoir 2610. The urine can then be drawn from the reservoir 2610 via the tube 2621 and through the outlet 2620 using, for example, an external vacuum source (not shown). The material of which permeable support 2640 is formed may be compressible. The material can also have sponge-like properties such that the material can maintain shape when wet, thereby maintaining contact with the user during a urination event via a slight protrusion of the permeable support 2640 outside the casing 2604 via the elongated opening 2604A. While the permeable support 2640 is shown with casing 2604 in FIGS. 46 and 47 for illustration purposes, the permeable support 2640 can be used in conjunction with any of the assemblies or casings shown or described herein, such as, for example, the assembly 802 of FIG. 9, the assembly of FIG. 18, the casing 1504 of FIG. 27, the casing 1604 of FIG. 32, the casing 1804 of FIGS. 34-35, the assembly 1702 of FIGS. 37-38, the casing 2004 of FIG. 40, the casing 2404 of FIG. 44A, and/or the casing 2504 in FIG. 45.

Figure 49A:
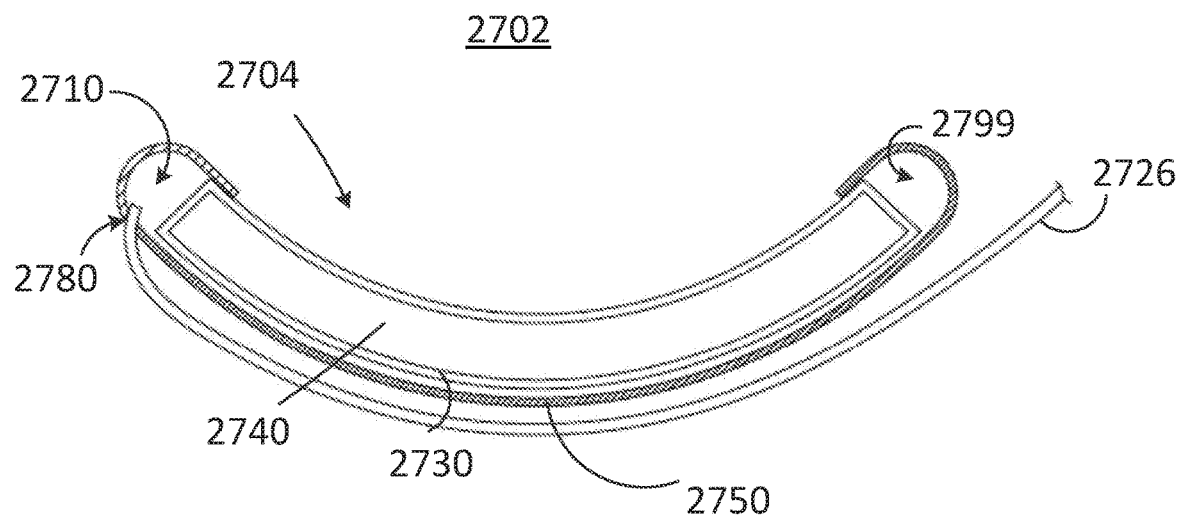
FIG. 49A is a schematic illustration of a cross-sectional view of an assembly, according to an embodiment.

In some embodiments, rather than including an outlet tube as shown and described with respect to assembly 2500 in FIG. 45, an assembly can include an outlet tube inserted partially into the reservoir and extending away from the assembly. For example, FIG. 49A is a lengthwise cross-sectional view of an assembly 2702. The assembly 2702 can include a casing 2704, a permeable support 2740, and a permeable membrane 2730. The assembly 2702 can be similar in structure and/or function to any of the assemblies described herein, such as, for example, the assembly 102 shown and described with respect to FIG. 1, the assembly 1802 shown and described with respect to FIG. 35, and/or the assembly 2602 shown and described with respect to FIG. 46. Specifically, the casing 2704 can be similar in structure and/or function to any of the casings described herein, such as, for example, the casing 1504 shown and described with respect to FIGS. 27 and 28, the casing 1804 shown and described with respect to FIG. 34, the casing 2004 shown and described with respect to FIG. 40, the casing 2404 shown and described with respect to FIG. 44A and/or the casing 2504 shown and described with respect to FIG. 45. The casing 2704 can include, for example, an impermeable backing 2750, a reservoir 2710, a closed end 2799 opposite the reservoir 2710, and an opening 2780 defined by the impermeable backing 2750 and/or the reservoir 2710. The casing 2704 can be made with or without a precurved form. For example, in some implementations, the casing 2704 can be precurved such that the casing 2704 is concave or convex. Although shown as including a separate permeable membrane 2730 and permeable support 2740, in some embodiments the assembly 2702 can include a permeable support 2740 made of a material such that the permeable support 2740 can include some or all of the functions of any of the permeable membranes described herein. In such embodiments, the assembly 2702 can include only a permeable support and not a separate permeable membrane disposed on the permeable support.

Figure 49B:
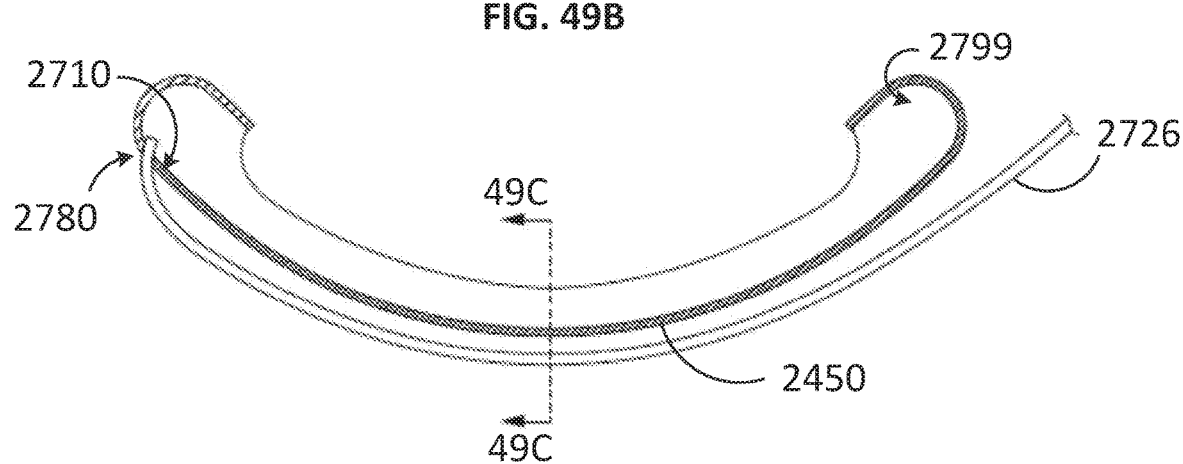
FIG. 49B is a schematic illustration of a cross-sectional view of an impermeable casing of the assembly of FIG. 49A.
Figure 49C:
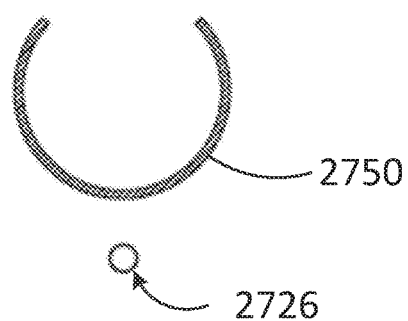
FIG. 49C is a schematic illustration of a cross-sectional view of the impermeable casing of FIG. 49B taken along line 49C-49C.

The assembly 2702 can include an outlet tube 2726 that can be inserted into the casing 2704 through the opening 2780 such that the inserted open end of the tube 2726 can be disposed within the reservoir 2710. In such an arrangement, a lumen of the tube 2726 can be in fluidic communication with the reservoir. An exemplary casing 2704 with a mounted outlet tube 2726 is shown in cross-sectional view in FIG. 49B. The outlet tube 2726 can be made of flexible or rigid material. As shown in FIG. 49B and in the cross-sectional view taken along line 49C-49C shown in FIG. 49C, the outlet tube 2726 can extend along the outside of and away from the casing 2704. The outlet tube 2726 can have any suitable length such that the outlet tube 2726 is suitable for the extraction of fluid from the reservoir 2710. The outlet tube 2726 can be secured to the casing 2704 through any leak-proof coupling mechanism, for example by using pressure insertion through the opening 2780, or by using the stiction properties of the tube 2726 and the casing 2704. In some implementations, the outlet tube 2726 can be secured to the casing 2704 due to the reservoir end of the outlet tube 2726 having a larger diameter than the opening 2880A. In some implementations, the outlet tube 2726 can be secured to the casing 2704 via, for example, a leak-proof fastening mechanism such as, for example, adhesive and/or tape. In some implementations, the outlet tube 2726 can be directly coupled to an external receptacle (e.g., the external receptacle 160) such that urine collected in the reservoir can be transported to the external receptacle via the outlet tube 2726. In some implementations, the outlet tube 2726 can be coupled to an external receptacle via another tube (not shown) coupled to the outlet tube 2726. In some implementations, a vacuum source can be used to assist in drawing fluid from the reservoir 2710 via the outlet tube 2726.

Figure 50A:
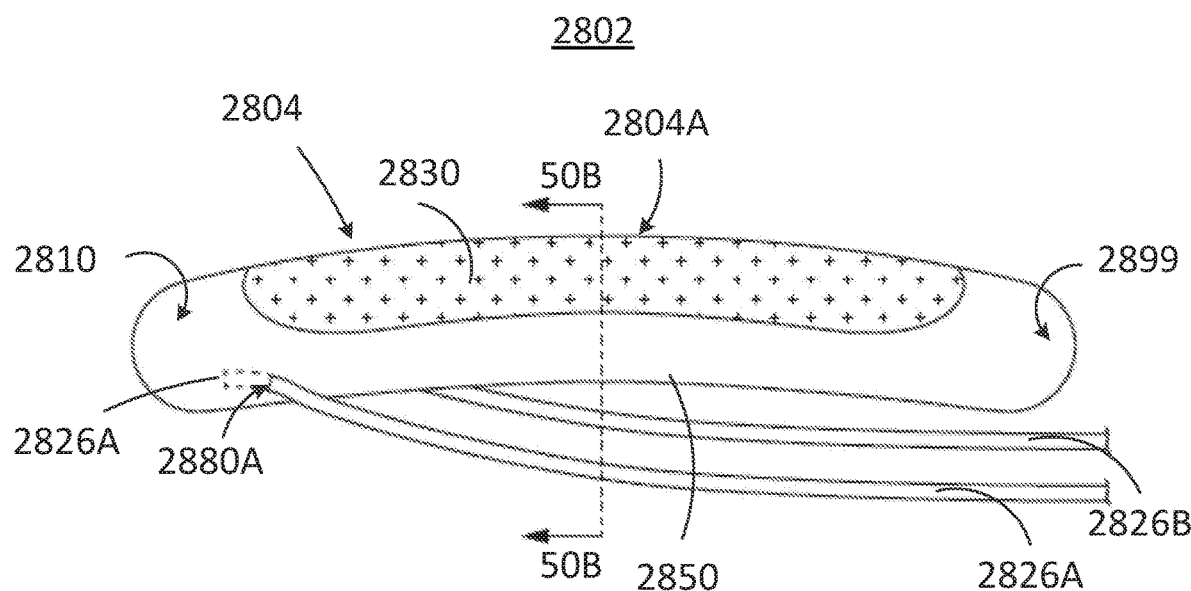
FIG. 50A is a schematic illustration of an assembly with more than one outlet tube, according to one embodiment.
Figure 51:
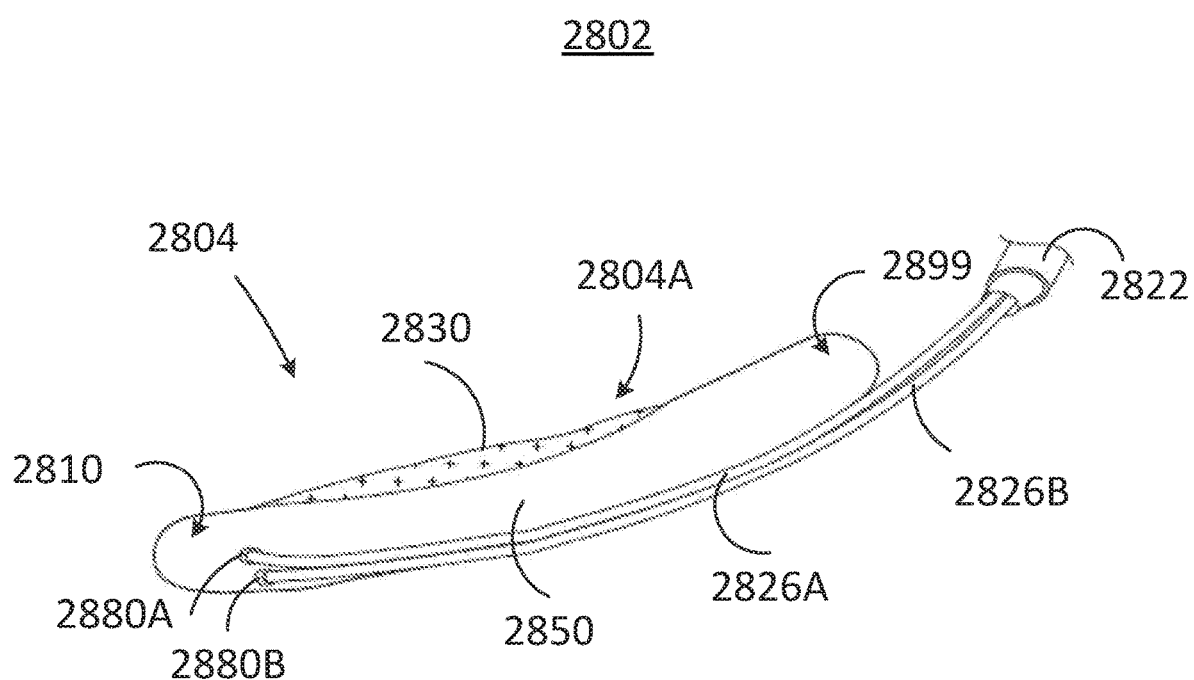
FIG. 51 is a shallow angled perspective view of the assembly of FIG. 50A.

Although FIG. 49A shows the opening 2780 disposed in or near the reservoir 2710, in other embodiments one or more openings similar in structure and/or function to the opening 2780 can be disposed at one or more other positions along the length of the impermeable backing 2750 as well as laterally along the width of the impermeable backing 2750 such that a tube such as the outlet tube 2726 can be inserted and secured in each of the one or more openings of the casing 2704. For example, as shown in FIG. 50A, the assembly 2802 includes a first tube 2826A and a second tube 2826B. The assembly 2802 can be similar in structure and/or function to any of the assemblies described herein. For example, the assembly 2802 can include a casing 2804 defining an elongated opening 2804A, an impermeable backing 2850, a reservoir 2810, and a closed end 2899 opposite the reservoir end. FIG. 51 shows a shallow angled perspective view of the assembly 2802 with the first tube 2826A and the second tube 2826B coupled to the casing 2804. As shown in FIGS. 50A and 51, the casing 2804 can define a first opening 2880A and a second opening 2880B (shown in FIG. 51) defined in the impermeable backing 2850 through which the first tube 2826A and the second tube 2826B, respectively, can be inserted. For example, as shown in phantom in FIG. 50A, the reservoir end of the tube 2826A can be inserted through the opening 2880A into the reservoir 2810. The portion of each of the first tube 2826A and the second tube 2826B disposed within the casing can be of any suitable length that allows proper extraction of fluid collected in the reservoir without any obstruction to the open tips of the first tube 2826A and the second tube 2826B. The open tips of the first tube 2826A and the second tube 2826B can be disposed within the reservoir 2810 such that fluid can flow from the reservoir 2810 during use without obstruction or interference by the casing 2804 with the assistance of, for example, vacuum suction or gravity.

In some implementations, the two openings 2880A and 2880B can be disposed at any suitable location along the length and width of the casing 2804 such that there may be sufficient spatial separation between the reservoir ends of the first tube 2826A and the second tube 2826B for maximal and effective extraction of urine collected in the reservoir 2810 during use of the assembly 2802. Additionally, the two openings 2880A and 2880B may be positioned such that proper coupling between the first tube 2826A, the second tube 2826B, and the casing can be ensured.

Figure 50B:
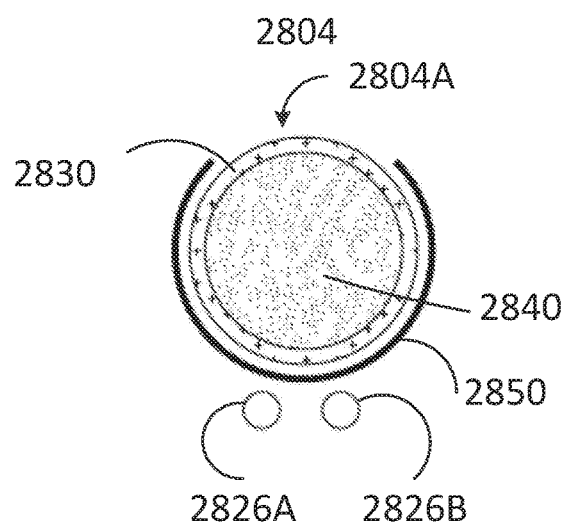
FIG. 50B is a cross-sectional view of the assembly of FIG. 50A, taken along the line 50B-50B.

The assembly 2802 can be fashioned such that the outlet tubes 2826A and 2826B extend along the outside of the casing 2804 as shown in FIG. 50B, which is a cross-sectional view taken along the line 50B-50B in FIG. 50A. The assembly 2802 can include a permeable support 2840 and a permeable membrane 2830, and can be positioned such that a portion of the permeable membrane 2830 extends through the elongated opening 2804A and against or near the urethral opening of the user. In some implementations, the tubes 2826A and 2826B can be directly coupled to an external receptacle (e.g., the external receptacle 160) such that urine collected in the reservoir can be transported to the external receptacle via the tubes 2826A and 2826B. In some implementations, the tubes 2826A and 2826B can be coupled to an external receptacle via an external tube 2822 (shown in FIG. 51) coupled to the tubes 2826A and 2826B. The tubes 2826A and 2826B can be connected to the external tube 2822 using any coupling mechanism that allows leak-proof connection, such as, for example, tube fittings, adhesive, or tape. In some implementations, a vacuum source can be used to assist in drawing fluid from the reservoir 2810 via the tubes 2826A and 2826B. The positioning, structure and material of the tubes 2826A and 2826B, external tube 2822, and the casing 2804 can be such that the assembly 2802 allows for free flow of fluid from a urethral opening of a user, through the permeable membrane 2830, through the permeable support 2840, into the reservoir 2810, through the openings 2880A and 2880B, and through the tubes 2826A and 2826 without obstruction of the open reservoir ends of the tubes 2826A and 2826B. Additionally, the assembly 2802 can withstand the pressure differential due to the application of vacuum suction to draw out the fluid (e.g., urine) collected in the reservoir 2810. The assembly 2802 can also simultaneously be sufficiently pliable and/or flexible to conform to the size and shape of different users to ensure effective transfer of voided urine.

Although the assembly 2802 is shown to include a permeable support 2840 (indicated by the dot pattern) and a permeable membrane 2830 (indicated by a cross pattern) in FIG. 50B, in other embodiments the assembly may include a permeable support 2840 made of material such that it serves the functions of both the permeable support and the permeable membrane. Such a permeable support 2840 can be similar in structure and/or function to permeable support 2640 in assembly 2602. For example, the permeable support 2840 can have an exterior surface with wicking properties, a high absorptive rate, and/or a high permeation rate such that urine can be rapidly absorbed and/or transported therethrough. Further, the permeable support 2840 can be soft and/or minimally abrasive such that the exterior surface of the permeable support 2840 does not irritate the skin of the user. The permeable support 2840 can also be made of a material that can wick fluid away from the urethral opening and/or the skin of the user such that the dampness of the skin of the user is lessened and infections are prevented.

While various embodiments of the system, methods and devices have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having any combination or sub-combination of any features and/or components from any of the embodiments described herein. In addition, the specific configurations of the various components can also be varied. For example, the size and specific shape of the various components can be different than the embodiments shown, while still providing the functions as described herein.

The invention claimed is:

1. A fluid collection apparatus, comprising:
 a fluid reservoir;
 a fluid outlet;
 at least one opening between the fluid reservoir and the fluid outlet;
 a tube having a first end in fluid communication with the fluid reservoir and extending through the fluid outlet to a second, fluid discharge end;
 a fluid permeable support distinct from and at least proximate to the fluid reservoir, the fluid permeable support at least partially defining a channel sized and shaped to receive the tube, the channel distinct from the fluid reservoir; and
 a fluid permeable membrane that extends over at least a portion of the fluid permeable support, a portion of the fluid permeable membrane extending across the at least one opening;
 wherein the tube extends behind at least a portion of the fluid permeable support and at least a portion of the fluid permeable membrane.

2. The fluid collection apparatus of claim 1, wherein the fluid permeable support includes a spun plastic.

3. The fluid collection apparatus of claim 1, further comprising an impermeable layer that at least partially defines at least one of the fluid reservoir, the fluid outlet, or the at least one opening.

4. The fluid collection apparatus of claim 3, wherein the impermeable layer is an integral, unitary structure.

5. The fluid collection apparatus of claim 3, wherein the impermeable layer is a multi-piece structure.

6. The fluid collection apparatus of claim 5, wherein the impermeable layer includes an adhesive tape.

7. The fluid collection apparatus of claim 5, wherein the impermeable layer includes a flexible cap and a backing portion that is distinct from the flexible cap, the flexible cap at least partially defining fluid reservoir.

8. The fluid collection apparatus of claim 7, wherein the impermeable layer further includes one or more securing portions that at least connect the flexible cap to the backing portion.

9. The fluid collection apparatus of claim 3, wherein the impermeable layer forms at least a portion of a fluid impermeable casing.

10. The fluid collection apparatus of claim 3, wherein the impermeable layer forms an impermeable backing.

11. The fluid collection apparatus of claim 3, wherein the impermeable layer at least partially defines the fluid reservoir.

12. The fluid collection apparatus of claim 11, wherein the fluid reservoir is substantially unoccupied.

13. The fluid collection apparatus of claim 3, wherein the impermeable layer at least partially defines the fluid outlet.

14. The fluid collection apparatus of claim 3, wherein the impermeable layer at least partially defines the at least one opening.

15. A fluid collection system, comprising:
 the fluid collection apparatus of claim 1; and
 a vacuum source fluidly coupled to the tube and configured to apply a vacuum to the tube sufficient to remove fluid from the fluid collection apparatus.

16. A fluid collection apparatus, comprising:
 an impermeable layer at least partially defining a fluid reservoir, a fluid outlet, and at least one opening between the fluid reservoir and the fluid outlet;
 a fluid permeable support disposed at least partially within the impermeable layer, the fluid permeable support distinct from and at least proximate to the fluid reservoir, the fluid permeable support at least partially defining a channel that is distinct from the fluid reservoir; and
 a tube having a first end in fluid communication with the fluid reservoir and extending through the channel and extending through the fluid outlet to a second, fluid discharge end.

17. The fluid collection apparatus of claim 16, wherein the impermeable layer is an integral, unitary structure.

18. The fluid collection apparatus of claim 16, wherein the impermeable layer is a multi-piece structure.

19. The fluid collection apparatus of claim 16, wherein the impermeable layer includes a flexible cap and a backing portion that is distinct from the flexible cap, the flexible cap at least partially defining the fluid reservoir.

20. The fluid collection apparatus of claim 16, further comprising a fluid permeable membrane that extends over at least a portion of the fluid permeable support, a portion of the fluid permeable membrane extending across the at least one opening.

21. A fluid collection apparatus, comprising:
    a fluid reservoir;
    a fluid outlet;
    at least one opening between the fluid reservoir and the fluid outlet;
    an impermeable backing at least defining at least a portion of the at least one opening;
    a tube having a first end in fluid communication with the fluid reservoir and extending through the fluid outlet to a second, fluid discharge end;
    a fluid permeable support distinct from and at least proximate to the fluid reservoir, the fluid permeable support at least partially defining a channel sized and shaped to receive the tube, the channel distinct from the fluid reservoir; and
    a fluid permeable membrane that extends over at least a portion of the fluid permeable support, a portion of the fluid permeable membrane extending across the opening;
    wherein the tube extends behind at least a portion of the fluid permeable support and at least a portion of the fluid permeable membrane.

* * * * *